US012629065B1

(12) United States Patent
Park et al.

(10) Patent No.: US 12,629,065 B1
(45) Date of Patent: May 19, 2026

(54) IMPLANTABLE CONTINUOUS GLUCOSE MONITOR DEVICE

(71) Applicant: UXN Co., Ltd., Uiwang-si (KR)

(72) Inventors: Sejin Park, Suwon-si (KR); Sun Kil Kang, Seongnam-si (KR)

(73) Assignee: UXN Co., Ltd., Suwon-si (KR)

( * ) Notice: Subject to any disclaimer, the term of this patent is extended or adjusted under 35 U.S.C. 154(b) by 0 days.

(21) Appl. No.: 19/190,577

(22) Filed: Apr. 25, 2025

Related U.S. Application Data

(60) Provisional application No. 63/781,860, filed on Apr. 1, 2025.

(51) Int. Cl.
*A61B 5/145* (2006.01)
*A61B 5/00* (2006.01)
*A61B 5/1486* (2006.01)

(52) U.S. Cl.
CPC ........ *A61B 5/14865* (2013.01); *A61B 5/0031* (2013.01); *A61B 5/1451* (2013.01); *A61B 5/14532* (2013.01)

(58) Field of Classification Search
CPC . A61B 5/14865; A61B 5/0031; A61B 5/1451; A61B 5/14532
See application file for complete search history.

(56) References Cited

U.S. PATENT DOCUMENTS

| | | | | |
|---|---|---|---|---|
| 10,040,948 | B1* | 8/2018 | Boo ..................... | A61B 5/1473 |
| 11,571,148 | B1* | 2/2023 | Puttananjegowda .. | C12Q 1/002 |

| | | | | |
|---|---|---|---|---|
| 2006/0008667 | A1* | 1/2006 | Kim ................... | G01N 27/3271 |
| | | | | 205/67 |
| 2009/0192745 | A1 | 7/2009 | Kamath et al. | |
| 2013/0245981 | A1 | 9/2013 | Estes et al. | |
| 2013/0331676 | A1* | 12/2013 | Morgan ............... | A61B 5/0538 |
| | | | | 600/365 |
| 2016/0235347 | A1* | 8/2016 | Baig .................. | A61B 5/14532 |
| 2019/0150812 | A1 | 5/2019 | Park et al. | |
| 2019/0154618 | A1 | 5/2019 | Boo et al. | |
| 2019/0175083 | A1* | 6/2019 | Cohen ................. | A61B 5/6821 |

(Continued)

FOREIGN PATENT DOCUMENTS

| | | |
|---|---|---|
| CN | 110632146 A | 12/2019 |

OTHER PUBLICATIONS

U.S. Appl. No. 19/190,573—Non-Final Office Action mailed on Jul. 1, 2025, 16 pages.

(Continued)

*Primary Examiner* — Eric J Messersmith
(74) *Attorney, Agent, or Firm* — K&L Gates LLP

(57) ABSTRACT

A continuous glucose monitor (CGM) sensor includes a glucose oxidation electrode and a counter electrode, and does not include a glucose-specific enzyme. The glucose oxidation electrode includes a nanoporous layer comprising metal nanoparticles. The CGM sensor generates an electrical signal indicative glucose oxidation in a liquid containing glucose, which has a correlation with an effective surface area of the metal nanoparticles in the nanoporous layer. When the CGM sensor is implanted in a subject's body, an AC voltage is applied between the glucose oxidation electrode and the counter electrode, and impedance is obtained. A glucose level for the subject is determined using the impedance without use of information or data related to glucose sensitivity of a sensor or sensors over use or time.

20 Claims, 56 Drawing Sheets

(56)       References Cited

U.S. PATENT DOCUMENTS

| | | | |
|---|---|---|---|
| 2020/0029869 A1* | 1/2020 | Cho | A61B 5/14514 |
| 2020/0037875 A1 | 2/2020 | Simpson et al. | |
| 2022/0313124 A1 | 10/2022 | Garcia et al. | |
| 2022/0357318 A1 | 11/2022 | Aghvanyan et al. | |
| 2023/0079720 A1* | 3/2023 | Goode | A61B 5/14865 |
| | | | 600/347 |
| 2023/0113717 A1* | 4/2023 | Poudineh | A61B 5/1451 |
| | | | 600/361 |
| 2023/0240570 A1* | 8/2023 | Böhm | A61B 5/14735 |
| | | | 73/1.02 |
| 2023/0341350 A1* | 10/2023 | Rauf | C25D 5/56 |
| 2024/0041366 A1 | 2/2024 | DeHennis et al. | |
| 2024/0215915 A1* | 7/2024 | Ahn | A61B 5/14532 |
| 2024/0358282 A1 | 10/2024 | Rais et al. | |
| 2025/0120616 A1* | 4/2025 | Cheng | B01L 3/502715 |

OTHER PUBLICATIONS

U.S. Appl. No. 19/190,569—Non-Final Office Action mailed on Jul. 29, 2025, 17 pages.

U.S. Appl. No. 19/190,573—Final Office Action mailed on Nov. 4, 2025, 19 pages.

* cited by examiner

System Diagram

IMPLANTABLE CONTINUOUS GLUCOSE MONITOR DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

The present disclosure relates to glucose sensing technologies, more specifically to measuring glucose sensor sensitivity and renewing glucose sensor sensitivity.

SUMMARY

Glucose Measurement

One aspect of the disclosure provides a method for glucose measurement. The method may comprise: providing a continuous glucose monitor (CGM) device comprising a nanoporous layer and configured to generate an electrical signal indicative of glucose oxidation occurring in the nanoporous layer while the nanoporous layer is in contact with liquid containing glucose, wherein the nanoporous layer may comprise metal nanoparticles; causing to insert at least part of the CGM device into a subject's body such that the nanoporous layer is in contact with interstitial fluid of the subject, wherein sensitivity of the nanoporous layer for glucose oxidation may deteriorate over time while the CGM device is maintained in the subject's body; maintaining the at least part of the CGM device in the subject's body over time during which materials from the interstitial fluid contact or cover some surfaces of the metal nanoparticles; while the CGM device is maintained in the subject's body, applying a cleaning voltage input to the nanoporous layer such that at least part of the materials contacting or covering surfaces of the metal nanoparticles are removed therefrom; and measuring the electrical signal indicative of glucose oxidation for determining a glucose level for the subject, wherein measuring the electrical signal is repeated while the CGM device is maintained in the subject's body.

Electrical Signal

In any of the foregoing methods, measuring the electrical signal may comprise applying a DC voltage to the nanoporous layer for an electric current indicative of glucose oxidation occurring in the nanoporous layer. The cleaning voltage input may comprise a non-DC voltage waveform to the nanoporous layer that causes to form an oxide layer on surfaces of at least part of the metal nanoparticles such that the oxide layer is interposed between the at least part of the metal nanoparticles and at least part of the materials. The non-DC voltage waveform may further cause to dissolve the oxide layer such that the at least part of the materials releases from at least part of the metal nanoparticles.

Electrical Signal and Effective Surface Area

In any of the foregoing methods, the electrical signal indicative of glucose oxidation may have a correlation with an effective surface area of the metal nanoparticles in the nanoporous layer such that, at a given glucose concentration in the liquid, the larger the effective surface area is, the greater the electrical signal indicative of glucose oxidation is generated. Applying the cleaning voltage input may increase the effective surface area of the metal nanoparticles in the nanoporous layer. Measuring the electrical signal may be performed after applying the cleaning voltage. Applying the cleaning voltage input substantially immediately increases the effective surface area of the metal nanoparticles and accordingly improves the sensitivity of the nanoporous layer for glucose oxidation. Measuring the electrical signal may be repeated continuously or intermittently.

Applying Cleaning Voltage Input

In any of the foregoing methods, applying the cleaning voltage input may comprise applying a non-DC voltage input which causes to renew or refresh at least part of surfaces of at least part of the metal nanoparticles, which improves sensitivity of the nanoporous layer for glucose oxidation. The sensitivity of the nanoporous layer may be substantially immediately improved upon completion of applying the non-DC voltage input. Applying the non-DC voltage input may comprise applying pulses having both a positive voltage and a negative voltage to the nanoporous layer. Applying the pulses may cause to form an oxide layer on surfaces of at least part of the metal nanoparticles in the nanoporous layer and subsequently remove at least part of the oxide layer formed, which removes at least part of the materials contacting or covering surfaces of the metal nanoparticles. Applying the non-DC voltage input may comprise applying an oxidation potential to the nanoporous layer to form an oxide layer on surfaces of at least part of the metal nanoparticles in the nanoporous layer, which removes at least part of the materials contacting or covering surfaces of the metal nanoparticles; and subsequently applying a reduction potential the nanoporous layer to dissolve at least part of the oxide layer formed by applying the oxidation potential.

Determining Sensitivity of Nanoporous Layer

In any of the foregoing methods, the CGM device may be configured to generate the cleaning voltage input as a first non-DC voltage and further configured to generate a second non-DC voltage that is different from the first non-DC voltage in terms of amplitude and waveform. Any of the foregoing methods may further comprise determining sensitivity of the nanoporous layer for glucose oxidation based on the impedance. Determining the sensitivity may comprise: applying the second non-DC voltage input to the nanoporous layer while the CGM device is maintained in the subject's body; and measuring an impedance of the nanoporous layer in response to the second non-DC voltage input. The sensitivity of the nanoporous layer for glucose oxidation may be determined using the impedance. The glucose level for the subject is determined at least based on the measured electrical signal and the determined sensitivity. Applying the cleaning voltage input may improve sensitivity of the nanoporous layer for glucose oxidation as at least part of the materials are removed from surfaces of the metal nanoparticles, wherein determining the sensitivity may be performed after improving the sensitivity with applying the cleaning voltage input. Applying the cleaning voltage input may be repeated multiple times to improve sensitivity of the nanoporous layer for glucose oxidation, wherein determining the sensitivity is performed subsequent to every time the cleaning voltage input is applied. Applying the cleaning voltage input may be repeated multiple times, and measuring the electrical signal may be repeated continuously or intermittently. Every time the cleaning voltage input is applied to improve the sensitivity, the sensitivity may be determined subsequent to applying the cleaning voltage input and prior to measuring the electrical signal.

CGM Device

In any of the foregoing methods, the CGM device may comprise at least one electrical circuit configured to generate at least one DC voltage and at least one non-DC voltage input for applying to the nanoporous layer. The CGM device may be in a single body, wherein causing to insert comprises causing to implant the single body of the CGM device in its entirety such that no portion of the single body stays outside the subject's body. The CGM device may further comprise at least one battery, at least one wireless communication circuit, and a housing that encloses the at least one battery and at least one wireless communication circuit and defines the single body.

Length of Implantation CGM Device

In any of the foregoing methods, the CGM device inserted into the subject's body may be maintained in the subject's body for a period of at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, at least 25 months, at least 26 months, at least 27 months, at least 28 months, at least 29 months, at least 30 months, at least 31 months, at least 32 months, at least 33 moths, at least 34 months, at least 35 months, or at least 36 months, etc. In any of the foregoing methods, the CGM device inserted into the subject's body may be maintained in the subject's body for at least 3 months. The cleaning voltage input may be applied multiple times during the period to improve sensitivity of the nanoporous layer for glucose oxidation. The single body of the CGM device may be removed from the subject's body after the period. Another CGM device may be implanted in the subject's body subsequent to removing the single body.

Continuous Glucose Monitor (CGM) Device

One aspect of the disclosure provides a continuous glucose monitor (CGM) device, which may comprise: electrodes comprising a first electrode and a second electrode, wherein the first electrode comprises a nanoporous layer comprising metal nanoparticles; at least one battery; circuitry comprising at least one DC voltage input circuit and at least one non-DC voltage input circuit; the at least one DC voltage input circuit operably connected to the at least one battery and configured to apply a DC voltage input between the first electrode and second electrode; the at least one non-DC voltage circuit operably connected to the at least one battery and configured to apply at least one non-DC voltage input between the first electrode and second electrode; and at least one wireless communication circuit configured for wirelessly sending data to an external device. The CGM device may be configured to be inserted into a subject's body such that the first electrode and the second electrode are in contact with interstitial fluid of the subject.

Non-DC Voltage Circuit

In the foregoing CGM device, the at least one non-DC voltage circuit may comprise a first non-DC voltage circuit configured to apply a first non-DC voltage input between the first electrode and second electrode; and a second non-DC voltage circuit configured to apply a second non-DC voltage input that differs from the first non-DC voltage in terms of both amplitude and waveform. The at least one non-DC voltage circuit may comprise an AC voltage circuit configured to apply an AC voltage input between the first electrode and second electrode; and a pulse voltage circuit configured to generate at least one pulse voltage input between the first electrode and second electrode. The at least one non-DC voltage circuit may comprise an AC voltage circuit configured to apply an AC voltage input between the first electrode and second electrode. The CGM device may further comprise at least one circuit configured to determine an impedance of the nanoporous layer in response to the AC voltage applied between the first electrode and second electrode. The at least one non-DC voltage circuit may comprise an AC voltage circuit configured to apply an AC voltage input between the first electrode and second electrode. The CGM device may further comprise at least one circuit configured to perform electrochemical impedance spectrometry in response to the AC voltage applied between the first electrode and second electrode.

Wireless Charging Circuit

Any of the foregoing CGM devices may further comprise at least one wireless charging circuit configured to wirelessly receive power for charging the at least one battery.

Housing

Any of the foregoing CGM devices may be further comprise a housing to enclose the electrodes, the at least one battery, the circuitry, the at least one wireless communication circuit to form a single body configured to be implanted in its entirety into the subject's body such that no portion of the single body stays outside the subject's body. The housing may comprise a liquid-tight compartment configured to inhibit the interstitial fluid from flowing thereinto and a liquid-contacting compartment configured to let the interstitial fluid flow thereinto. The liquid-tight compartment may enclose the at least one battery, the circuitry, and the at least one wireless communication circuit. The liquid-contacting compartment may enclose at least a portion of the first electrode and at least a portion of the second electrode such that the first electrode and the second electrode are in contact with the interstitial fluid.

Electrical Signal

Any of the foregoing CGM devices may be configured to measure an electrical signal indicative of glucose oxidation occurring in the nanoporous layer while the first electrode and the second electrode are in contact with interstitial fluid of the subject, configured to apply a cleaning voltage input between the first and second electrodes to improve sensitivity of the nanoporous layer for glucose oxidation while the first electrode and the second electrode are in contact with interstitial fluid of the subject, and further configured to measure an impedance of the nanoporous layer for determining sensitivity of the nanoporous layer for glucose oxidation while the first electrode and the second electrode are in contact with the interstitial fluid of the subject.

DC Voltage

Any of the foregoing CGM devices may be configured to apply the DC voltage input between the first electrode and the second electrodes for measuring an electrical signal indicative of glucose oxidation occurring in the nanoporous layer while the first electrode and the second electrode are in contact with the interstitial fluid of the subject.

Non-DC Voltage

Any of the foregoing CGM devices may be configured to apply the non-DC voltage between the first and second electrodes to renew surfaces of at least part of the metal nanoparticles to improve sensitivity of the nanoporous layer for glucose oxidation while the first electrode and the second electrode are in contact with the interstitial fluid of the subject. In any of the foregoing CGM devices, the non-DC voltage may be designed to cause at least part of materials in contact with surfaces of the metal nanoparticles to be removed therefrom. Any of the foregoing CGM devices may be configured to apply the non-DC voltage between the first electrode and the second electrode for measuring an impedance of the nanoporous layer while the first electrode and the second electrode are in contact with the interstitial fluid of the subject. Any of the foregoing CGM devices may be configured to apply the non-DC voltage between the first electrode and second electrode for determining real time sensitivity of the nanoporous layer while the first electrode and the second electrode are in contact with the interstitial fluid of the subject. The non-DC voltage may be an AC voltage with an amplitude and a frequency designed to receive an impedance response of the nanoporous layer thereto. Any of the foregoing CGM devices may be configured to apply the non-DC voltage between the first electrode and the second electrode for measuring an impedance indicative of solid-liquid interface information of the nanoporous layer which is for use in determining real time sensitivity of the nanoporous layer for glucose oxidation while the first electrode and the second electrode are in contact with the interstitial fluid of the subject.

Method of Using CGM Device

One aspect of the disclosure provides a method of using any of the CGM devices provided herein, the method comprising: causing to insert at least part of the CGM device into a subject's body such that the first electrode and the second electrode are nanoporous layer is in contact with interstitial fluid of the subject, maintaining the at least part of the CGM device in the subject's body over time during which glucose sensitivity of the nanoporous layer for glucose sensitivity changes; and determining the glucose sensitivity of the nanoporous layer while the first electrode and the second electrode are in contact with interstitial fluid of the subject. Determining the glucose sensitivity may comprise applying an AC voltage input to the nanoporous layer while the CGM device is maintained in the subject's body; and measuring an impedance of the nanoporous layer in response to the AC voltage input, wherein the glucose sensitivity of the nanoporous layer is determined using the impedance.

Another Method of Using CGM Device

Another aspect of the disclosure provides a method of using any of the CGM devices provided herein, the method comprising: causing to insert at least part of the CGM device into a subject's body such that the first electrode and the second electrode are in contact with interstitial fluid of the subject, maintaining the at least part of the CGM device in the subject's body over time during which materials from the interstitial fluid contact or cover some surfaces of the metal nanoparticles; and applying a non-DC voltage input between the first electrode and the second electrode such that at least part of the materials contacting or covering surfaces of the metal nanoparticles are removed therefrom.

Yet Another Method of Using CGM Device

Yet another aspect of the disclosure provides a method of using any of the CGM devices provided herein, the method comprising: causing to insert at least part of the CGM device into a subject's body such that the first electrode and the second electrode are in contact with interstitial fluid of the subject, maintaining the at least part of the CGM device in the subject's body over time during which materials from the interstitial fluid contact or cover some surfaces of the metal nanoparticles, which causes glucose sensitivity of the nanoporous layer to deteriorate; and while the first electrode and the second electrode are in contact with interstitial fluid of the subject, applying a non-DC voltage input between the first electrode and the second electrode such that at least part of the materials contacting or covering surfaces of the metal nanoparticles are removed therefrom; and while the first electrode and the second electrode are in contact with interstitial fluid of the subject, applying an AC voltage input between the first electrode and the second electrode to determine an impedance of the nanoporous layer. Applying the non-DC voltage input may improve the glucose sensitivity substantially immediately, wherein the impedance of the nanoporous layer indicates or determines the glucose sensitivity of the nanoporous layer at the time of applying the AC voltage, wherein the method further comprises measuring an electrical signal indicative of glucose oxidation for determining a glucose level of the subject subsequent to determining the glucose sensitivity.

Glucose Measurement

One aspect of the disclosure provides a method for glucose measurement. The method may comprise: providing a continuous glucose monitor (CGM) device comprising a first electrode and a second electrode, wherein the first electrode comprises a nanoporous layer comprising metal nanoparticles; causing to insert at least part of the CGM device into a subject's body such that the first and second electrodes are in contact with interstitial fluid of the subject; maintaining the at least part of the CGM device in the subject's body over time during which glucose sensitivity of the nanoporous layer for glucose sensitivity changes; measuring an electric current generated from glucose oxidation occurring in the nanoporous layer while the CGM device is maintained in the subject's body; determining the glucose sensitivity for the nanoporous layer for glucose oxidation while the CGM device is maintained in the subject's body; computing a glucose level for the subject using the measured electrical signal and the determined glucose sensitivity for the nanoporous layer.

Glucose Sensitivity

In any of the foregoing methods, determining the glucose sensitivity may comprise: applying a non-DC voltage input to the nanoporous layer while the CGM device is maintained in the subject's body; and measuring an impedance of the nanoporous layer in response to the non-DC voltage input. The glucose sensitivity for the nanoporous layer may be determined using the impedance. The impedance may comprise a capacitive reactance, wherein the glucose sensitivity for the nanoporous layer is determined using the capacitive reactance and predetermined characteristic information for the nanoporous layer. The predetermined characteristic information comprises a correlation between the capacitive reactance and the glucose sensitivity for the nanoporous layer. The correlation may be determined for multiple CGM devices each comprising a first electrode that has the same or substantially the same characteristics as the first electrode of the CGM device used in the method. The correlation may be determined for multiple CGM devices each comprising a first electrode which is manufactured according to the same or substantially the same specification as the first electrode of the CGM device used in the method. The correlation may be determined for multiple CGM devices each comprising a first electrode which is manufactured in the same batch as the first electrode of the CGM device used in the method. The effective surface area of the metal nanoparticles decreases and sensitivity of the nanoporous layer for glucose oxidation deteriorates over time while the CGM device is maintained in the subject's body as materials from the interstitial fluid contact or cover some surfaces of the metal nanoparticles.

Correlation

In any of the foregoing methods, the correlation may be determined for multiple CGM devices each comprising a first electrode that has the same or substantially the same characteristics as the first electrode of the CGM device used in the method. In any of the foregoing methods, the correlation may be determined for multiple CGM devices each comprising a first electrode which is manufactured according to the same or substantially the same specification as the first electrode of the CGM device used in the method. In any of the foregoing methods, the correlation may be determined for multiple CGM devices each comprising a first electrode which is manufactured in the same batch as the first electrode of the CGM device used in the method. In any of the foregoing methods, the correlation may be determined for multiple CGM devices each comprising a nanoporous layer which is manufactured in the same batch as the nanoporous layer of the CGM device used in the method. In any of the foregoing methods, the correlation may be determined for multiple CGM devices each comprising a nanoporous layer which is prepared according to the same or substantially the same specification as the nanoporous layer of the CGM device used in the method. In any of the foregoing methods, the correlation may be determined for multiple CGM devices each comprising a nanoporous layer which is prepared using the same or substantially the same material as the nanoporous layer of the CGM device used in the method. In any of the foregoing methods, the correlation may be determined for multiple CGM devices each comprising a nanoporous layer which is prepared using a nanoparticle material manufactured according to the same or substantially the same specification as a nanoparticle material used to prepare the nanoporous layer of the CGM device used in the method. In any of the foregoing methods, the correlation may be determined for multiple CGM devices each comprising a nanoporous layer which is prepared using a nanoparticle material manufactured according to the same or substantially the same specification as a nanoparticle material used to prepare the nanoporous layer of the CGM device used in the method.

Protective Layer

In any of the foregoing methods, the first electrode of the CGM device may comprise at least one protective layer over the nanoporous layer, wherein the correlation is determined for multiple CGM devices each comprising at least one protective layer which is manufactured using the same material and the substantially the same thickness as the first electrode of the CGM device used in the method.

Electrical Signal

In any of the foregoing methods, the electrical signal is an electric current generated by glucose oxidation in the nanoporous layer, wherein a change in the electric current from glucose oxidation in the nanoporous layer in response to a change in a glucose concentration in a liquid represents the glucose sensitivity for the nanoporous layer.

Electrical Circuit

In any of the foregoing methods, the CGM device may comprise at least one electrical circuit configured to generate both a DC voltage and a non-DC voltage waveform, measuring the electrical signal comprises applying a DC voltage to the nanoporous layer for an electric current indicative of glucose oxidation occurring in the nanoporous layer, wherein measuring the electrical signal is repeated continuously or intermittently, wherein determining the glucose sensitivity comprises applying a non-DC voltage input to the nanoporous layer.

Single Body

In any of the foregoing methods, the CGM device may be in a single body, wherein causing to insert comprises causing to implant the single body of the CGM device in its entirety such that no portion of the single body stays outside the subject's body and such that the CGM device is maintained in the subject's body for an extended period of time longer than one month, wherein determining the glucose sensitivity is performed multiple times while the CGM device is maintained in the subject body.

Effective Surface Area

In any of the foregoing methods, an effective surface area of the metal nanoparticles may decrease and the glucose sensitivity of the nanoporous layer for glucose oxidation may deteriorate over time while the CGM device is maintained in the subject's body as materials from the interstitial fluid contact or cover some surfaces of the metal nanoparticles, wherein the method further comprises improving the glucose sensitivity of the nanoporous layer while the CGM device is maintained in the subject's body. Improving the glucose sensitivity may comprise applying a cleaning voltage input to the nanoporous layer such that at least part of the materials contacting or covering surfaces of the metal nanoparticles are removed therefrom, wherein the cleaning voltage input comprises a non-DC voltage. Applying the cleaning voltage input to improve the glucose sensitivity may be repeated multiple times while the CGM device is maintained in the subject body. Determining the glucose sensitivity may be performed subsequent to every time the cleaning voltage input is applied. The CGM device may be in a single body, wherein causing to insert comprises causing to implant the single body of the CGM device in its entirety such that no portion of the single body stays outside the subject's body and such that the CGM device is maintained in the subject's body for an extended period of time longer than one month. Determining the glucose sensitivity may be performed multiple times while the CGM device is maintained in the subject body. Applying the cleaning voltage input to improve the glucose sensitivity may be repeated multiple times while the CGM device is maintained in the subject body.

Obtaining Glucose Sensitivity

One aspect of the disclosure provides a method of obtaining glucose sensitivity of a continuous glucose monitor (CGM) device. The method may comprise: providing the CGM device that comprises a first electrode and a second electrode, and does not comprise a glucose-specific enzyme, wherein the first electrode comprises a nanoporous layer comprising metal nanoparticles; wherein the CGM device is configured to provide a DC current indicative of glucose oxidation in the nanoporous layer in response to applying a DC voltage between the first electrode and the second electrode, whereas the CGM device is configured to provide an impedance indicative of solid-liquid interface information of the metal nanoparticles in the nanoporous layer; causing to insert the CGM device into a subject's body such that the first electrode and the second electrode contact interstitial fluid of the subject; applying an AC voltage between the first electrode and the second electrode and obtaining, at a predetermined frequency, an obtained impedance value indicative of an effective surface area of the metal nanoparticles of the nanoporous layer that is capable of participating in glucose oxidation; and determining the glucose sensitivity using the obtained impedance value without use of information or data related to glucose sensitivity of a sensor or sensors over use or time.

Predetermined Correlation

In the foregoing method, the glucose sensitivity is determined using a predetermined correlation between the impedance and the glucose sensitivity of the CGM device. Any of the foregoing methods may comprise determining a predetermined correlation between the impedance and the glucose sensitivity of the CGM device, which comprises: prior to causing to insert the CGM device into the subject's body, causing the CGM device to be in contact with a fluid with a first glucose concentration; applying a first DC voltage between the first electrode and the second electrode and obtaining a first DC current indicative of first glucose oxidation in the first electrode; causing the CGM device to be in contact with a fluid with a second glucose concentration; applying a second DC voltage between the first electrode and the second electrode and obtaining a second DC current indicative of second glucose oxidation in the first electrode; obtaining a first glucose sensitivity by dividing a difference between the first DC current and the second DC current by a difference between the first glucose concentration and the second glucose concentration; repeating the above steps for a plurality of other CGM devices and obtaining a plurality of glucose concentrations; obtaining corresponding impedance values at the predetermined frequency for the CGM device and the plurality of other CGM devices in a test liquid; plotting inverse of the corresponding impedance values against the first glucose sensitivity of the CGM device and the plurality of glucose concentrations of the plurality of other devices sensors and obtaining the predetermined correlation.

Manufacturing Continuous Glucose Monitor Sensor

One aspect of the disclosure provides a method of manufacturing a continuous glucose monitor (CGM) sensor that comprises a glucose oxidation electrode and a counter electrode and does not comprise a glucose-specific enzyme. The method may comprise: preparing the glucose oxidation electrode by putting a metal nanoparticles suspension onto a conductive layer and drying the metal nanoparticles suspension to form a nanoporous layer on top of the conductive layer; providing the counter electrode to form the CGM sensor; obtaining a predetermined correlation between impedance and glucose sensitivity of the CGM sensor, which comprises: causing the CGM sensor to be in contact with a fluid with a first glucose concentration; applying a first DC voltage between the glucose oxidation electrode and the counter electrode and obtaining a first DC current indicative of the first glucose oxidation in the glucose oxidation electrode; causing the CGM sensor to be in contact with a fluid with a second glucose concentration; applying a second DC voltage between the glucose oxidation electrode and the counter electrode and obtaining a second DC current indicative of second glucose oxidation in the glucose oxidation electrode; obtaining a first glucose sensitivity by dividing a difference between the first DC current and the second DC current by a difference between the first glucose concentration and the second glucose concentration; repeating the above steps for a plurality of other CGM sensors and obtaining a plurality of glucose concentrations; obtaining corresponding impedance values at the predetermined frequency for the CGM sensor and the plurality of other CGM sensors in a test liquid; plotting inverse of the corresponding impedance values against the first glucose sensitivity of the CGM sensor and the plurality of glucose concentrations of the plurality of other CGM sensors and obtaining the predetermined correlation.

Another Method of Obtaining Glucose Sensitivity

One aspect of the disclosure provides a method of obtaining glucose sensitivity of a continuous glucose monitor (CGM) sensor that comprises a glucose oxidation electrode and a counter electrode and does not comprise a glucose-specific enzyme. The method may comprise: causing the CGM sensor to be in contact with a fluid with a first glucose concentration; applying a first DC voltage between the glucose oxidation electrode and the counter electrode and obtaining a first DC current indicative of first glucose oxidation in the glucose oxidation electrode; causing the CGM sensor to be in contact with a fluid with a second glucose concentration; applying a second DC voltage between the glucose oxidation electrode and the counter electrode and obtaining a second DC current indicative of second glucose oxidation in the glucose oxidation electrode; obtaining the glucose sensitivity by dividing a difference between the first DC current and the second DC current by a difference between the first glucose concentration and the second glucose concentration.

Obtaining Glucose Level

One aspect of the disclosure provides a method of obtaining a glucose level of a subject. The method may comprise: providing a continuous glucose monitor (CGM) sensor that comprises a glucose oxidation electrode and a counter electrode, and does not comprise a glucose-specific enzyme, wherein the glucose oxidation electrode comprises a nanoporous layer comprising metal nanoparticles; wherein the CGM sensor is configured to provide a DC current indicative of glucose oxidation in the glucose oxidation electrode when applying a DC voltage between the glucose oxidation electrode and the counter electrode, wherein the CGM sensor is configured to provide an impedance indicative of solid-liquid interface information of the metal nanoparticles in the nanoporous layer; causing to insert the CGM sensor into the subject's body, while the glucose oxidation electrode and the counter electrode are in contact with the interstitial fluid of the subject, applying an AC voltage between the glucose oxidation electrode and the counter electrode and obtaining, at a predetermined frequency, an obtained impedance value indicative of an effective surface area of the metal nanoparticles of the nanoporous layer that is capable of participating in glucose oxidation; determining the glucose sensitivity using the obtained impedance value and a predetermined correlation between impedance and glucose sensitivity of the CGM sensor; and obtaining the glucose level of the subject using the glucose sensitivity and the DC current indicative of glucose oxidation in the glucose oxidation electrode provided by the CGM sensor when the DC voltage is applied between the glucose oxidation electrode and the counter electrode.

DETAILED DESCRIPTION

Figure 1:
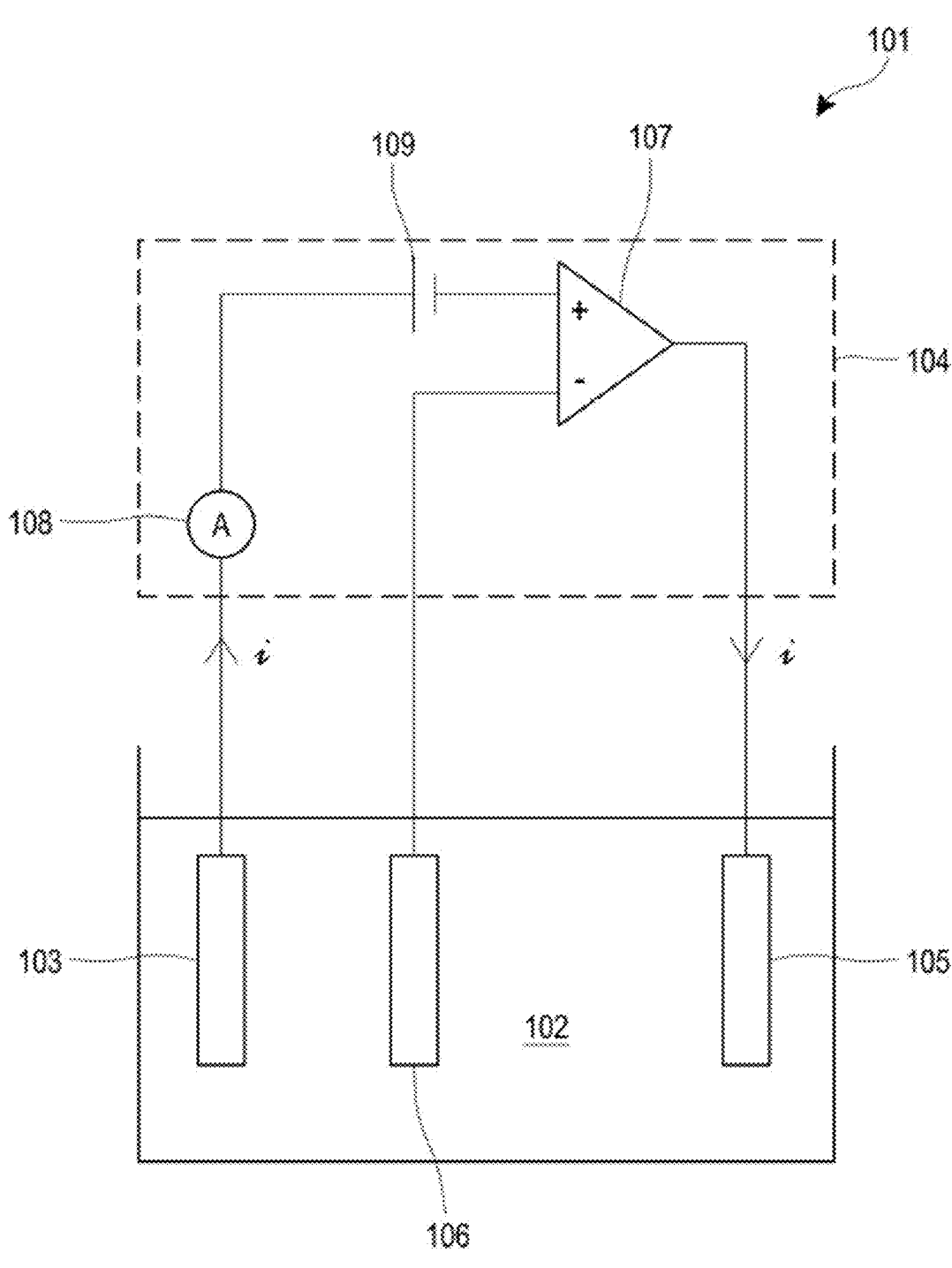
FIG. 1 illustrates an electrochemical sensing system for CGM according to an embodiment.

Hereinafter, implementations of the present invention will be described with reference to the drawings. These implementations are provided for better understanding of the present invention, and the present invention is not limited only to the implementations. Changes and modifications apparent from the implementations still fall in the scope of the present invention. Meanwhile, the original claims constitute part of the detailed description of this application.

Overview

Non-Enzyme Continuous Glucose Monitoring System

In a non-enzyme Continuous Glucose Monitoring (CGM) system with a nanoporous layer, the sensor's performance is closely tied to its effective surface area. A larger surface area provides more active sites for direct glucose oxidation, leading to a stronger current as a result of the increased number of oxidation reactions. Additionally, this expanded surface enhances the electrode's capacity, which influences its capacitance reactance—a key electrical property that reflects how the sensor stores and responds to charge. However, over time, the sensitivity of the CGM sensor can decline due to the accumulation of biomaterials, such as proteins and cellular debris, on the electrode surface. This buildup creates a barrier that interferes with the electrode's ability to effectively oxidize glucose, leading to reduced current generation and impaired glucose sensitivity. To combat this issue and restore optimal performance, a cleaning voltage can be applied to the electrode. This voltage helps dislodge and remove the deposited materials, thereby rejuvenating the electrode surface and improving the sensor's sensitivity.

Glucose Measurements

To ensure accurate glucose measurements, the relationship between glucose sensitivity and capacitance reactance is established. This is done by testing multiple sensors with the same design or from the same batch and plotting glucose sensitivity-calculated as the change in current divided by the change in glucose concentration-against reactance. This correlation establishes how reactance influences the sensor's ability to detect glucose levels. Once the implantable CGM device is in use, it first measures its reactance to determine its glucose sensitivity at that moment based on the pre-established correlation. Then, as glucose undergoes oxidation at the electrode, the generated current is measured. By applying the calculated glucose sensitivity, the system accurately converts the measured current into a real-time glucose concentration, ensuring precise monitoring while compensating for variations in sensor performance over time. This continuous process, including the cleaning mechanism, allows for sustained accuracy and reliability in glucose management.

Continuous Glucose Monitoring

Continuous Glucose Monitoring

Continuous glucose monitoring (CGM) is a system that tracks glucose levels in real-time for an extended period of time from a few days to several months. It typically involves a small sensor that is placed under the skin, which measures glucose levels in the interstitial fluid. This data is then sent wirelessly to a receiver, smartphone app, or insulin pump, allowing patients or healthcare professionals to monitor their glucose level continuously. The patients are then able to receive real-time information on how glucose levels are changing, helping them to make informed health decisions and better manage blood sugar levels to reduce the risk of complications associated with diabetes. CGMs typically determine electrical signals proportional to glucose concentration although not limited thereto.

Electrochemical CGM

Electrochemical glucose sensing measures glucose concentration in an electrolyte solution. FIG. 1 conceptually illustrates an electrochemical glucose-sensing system 101 for detecting a glucose concentration in a test fluid or electrolyte solution 102. The system 101 includes a working or sensing electrode 103, a counter electrode 105 and a reference electrode 106 that are connected to a potentiostat 104 and in contact with the test fluid 102. In embodiments, the potentiostat includes electric circuitry for functioning as a voltage source 109 and a current sensor 108. The voltage source 109 provides a bias voltage that drives redox reactions at the working electrode 103 and counter electrode 105. The potentiostat further includes an electric circuitry such as an op-amp 107 for maintaining the bias voltage at the working electrode 103 relative to the reference electrode 106. The current sensor 108 detects electric current generated by redox reactions involving glucose contained in the test fluid 102.

Enzymatic CGM

Many electrochemical CGMs utilize a glucose-specific enzyme for the detection of glucose molecules. The glucose-specific enzymes are placed in the working electrode 103 to react with glucose present in the interstitial fluid. When glucose molecules contact these glucose-specific enzymes, the enzymes catalyze or facilitate oxidation of glucose, and electron transfers generated in glucose oxidation generate electric current in the electrical circuit of the electrochemical sensing system.

Non-Enzymatic Glucose-Sensing Electrode

Non-enzymatic glucose-sensing systems do not use a glucose-specific enzyme or any enzyme for the glucose detection. Non-enzymatic electrochemical CGMs uses a working electrode that oxidizes glucose molecules without a glucose-specific enzyme. The working electrode may contain a material other than glucose-specific enzymes that can facilitate oxidation of glucose molecules at a moderate level of bias voltage. Generally, the higher the bias voltage, the more likely glucose oxidation occurs at the at least one glucose oxidation layer. However, because other chemical entities will also be oxidized at a high bias voltage, there is a limit for the bias voltage. Thus, non-enzymatic electrochemical glucose sensing relies on a material that oxidizes glucose at a bias voltage that does not cause oxidation of other chemical entities contained in the test fluid. Alternatively, there are non-electrochemical glucose-sensing systems that do not use redox reactions and do not use glucose-specific enzymes.

Nanoporous Layer for Non-Enzymatic Glucose-Sensing Electrode

Figure 2:
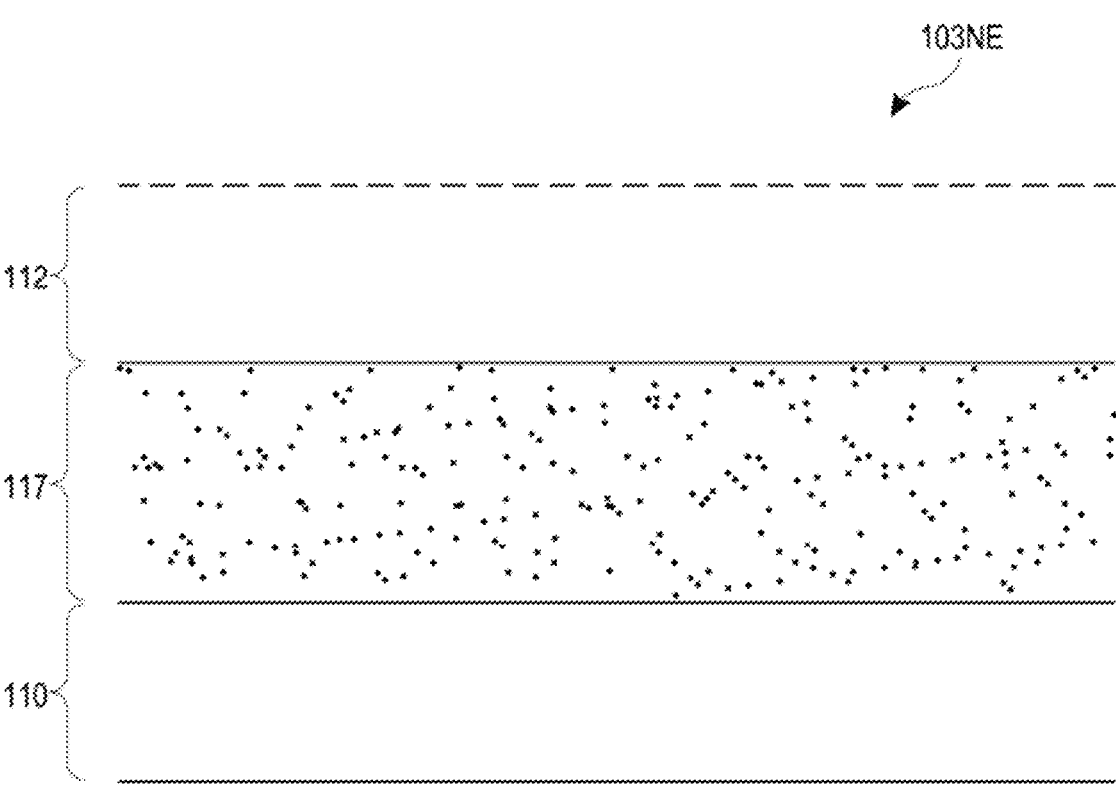
FIG. 2 illustrates layers of a working electrode including a nanoporous layer in the electrochemical sensing system of FIG. 1 according to an embodiment.

FIG. 2 illustrates a non-enzymatic working electrode (simply "working electrode") 103NE that includes an electrically conductive layer 110 and a nanoporous glucose oxidation layer (or nanoporous layer) 117. In embodiments, the nanoporous layer 117 includes nanoporous internal structures for causing, enabling or facilitating oxidation of glucose at a moderate bias voltage. When glucose oxidation occurs, the conductive layer 110 takes electrons from glucose oxidation, and electrical current is generated in the electrical circuit. The electrical current can be detected by the current sensor 108 and interpreted by hardware and software of the CGM system. Optionally, the working electrode 103NE may include at least one functional layer 112 over the nanoporous layer 117 or between the nanoporous layer 117 and conductive layer 110 (not shown).

Conductive Layer—Materials

With the bias voltage, the conductive layer 110 of FIG. 2 takes electrons from glucose oxidation and transfers them to the current sensor 108. In embodiments, the conductive layer 110 includes or is made of at least one electrically conductive material and is connected to electrical circuit of the system 101. In some embodiments, given the small scale of the conductive layer 110, semiconductive materials may be used instead of electrically conductive material. Non-limiting examples for a material of the conductive layer includes platinum (Pt), gold (Au), silver (Ag), ruthenium (Ru), stainless steel, silicon (amorphous, poly and single crystalline), conductive carbon materials, including graphite, graphene, fluorene, carbon nanotubes. In the embodiments, the conductive layer 110 does not include nanoporous internal structures of the glucose oxidation layer 117.

Conductive Layer—Configurations

In embodiments, the conductive layer 110 may be formed of a single layer of a homogeneous material. In the alternative, the conductive layer 110 may include multiple sublayers made of different materials. In some embodiments, the conductive layer 110 includes top sublayer and one or more sublayers under the top sublayer. In embodiments, the top sublayer does not contain silver, copper, aluminum or other conductive materials that are prone to oxidation more than silver, copper or aluminum. The top sublayer may be less electrically conductive than the other sublayer(s). In some embodiments, the conductive layer 110 includes a conductive carbon layer as the top sublayer and a silver layer as another sublayer under the carbon layer. The conductive layer 110 has a thickness that can vary significantly depending upon particular examples. In some embodiments, the conductive layer 110 may be omitted, and the nanoporous layer is directly connected to the current sensor via an electrically conductive wire or connection.

Functional Layer

Over the nanoporous layer 117 or between the nanoporous layer 117 and conductive layer 110 (not shown), there may be one or more functional layers 112, such as a maltose blocking layer, an electrolyte ion-blocking layer, and/or a biocompatibility layer, although not limited thereto.

Protective Layer

The functional layer 112 may be a protective layer, which may be crucial for enhancing the sensor's stability, selectivity, and longevity. Common materials and methods used for creating protective layers include, for example, nafion, metal-organic frameworks (MOFS), polymeric coatings, silica coatings, self-assembled monolayers (SAMS). Nafion is a widely used protective layer in electrochemical sensors. Nafion is a perfluorinated polymer that provides excellent chemical stability and selective permeability, allowing glucose to reach the sensor while blocking interfering substances. MOFs can be used as protective layers due to their high porosity and tunable structures. They can enhance the sensor's selectivity and stability by providing a controlled environment for glucose detection. Polymers like polyaniline, polypyrrole, and polyethylene glycol (PEG) can be used to coat the nanoporous metal surface. These coatings can improve biocompatibility and reduce fouling, which is essential for long-term sensor performance. Silica-based materials can be used to create a protective layer that is both biocompatible and chemically stable. Silica coatings can also be functionalized to improve selectivity and sensitivity. SAMs of thiols or silanes can be used to modify the surface of the nanoporous metal. These monolayers can provide a protective barrier while allowing for the functionalization of the surface with specific recognition elements for glucose. These protective layers help to enhance the performance and durability of the glucose sensor by preventing fouling, improving selectivity, and maintaining the activity of the sensing elements.

Counter Electrode

With the bias voltage, reduction of a chemical entity occurs at the counter electrode 105. In embodiments, the counter electrode 105 includes at least one electrically conductive or semiconductive material and is connected to electrical circuit of the system 101. In embodiments, the counter electrode 105 may be formed of a single layer of a homogenous material or multiple layers made of different materials. The conductive or semiconductive materials for the conductive layer 110 may also be used in the counter electrode 105 although not the same materials are used in the conductive layer 110 and in the counter electrode 105 in a particular system.

Reference Electrode

The reference electrode 106 provides stability in the electrochemical sensing system by maintaining the bias voltage between the sensing electrode 103 and the reference electrode. As a result, glucose oxidation can continue at the sensing electrode 103 even if reduction at the counter electrode 105 is not at the same rate as the oxidation at the sensing electrode 103. In some embodiments, the counter electrode 105 may be omitted, and the reference electrode 106 may serve dual functions of the counter and reference electrodes. In embodiments, the reference electrode 106 may be formed of a single layer of a homogenous material or multiple layers made of different materials. The conductive or semiconductive materials for the conductive layer 110 may also be used in the reference electrode 105 although not the same materials are used in the conductive layer 110 and in the reference electrode 106 in a particular system. In some embodiments, the reference electrode 106 may include a salt layer over the conductive or semiconductive material layer. For example, the salt layer may be made of or include silver chloride (AgCl).

Current Sensor

The current sensor 108 measures electric current flowing from the working electrode 103. The current sensor 108 may amperometrically detect electric current flowing at a specific point in time. In the alternative, the current sensor 108 may be a coulometric charge-measuring device.

Test Fluid

In embodiments, the test fluid may be a biological fluid of human or animal, although not limited thereto. In some embodiments, the test fluid may be a liquid mixture including a biological fluid and at least one additional substance added to the biological fluid. The biological fluid may include, for example, blood, interstitial fluid, cerebral spinal fluid, lymph fluid or urine, although not limited thereto. In some embodiments, the test fluid may include a non-biological liquid prepared for experiments.

Bias Voltage

The bias voltage applied between the working electrode 103NE and reference electrode 106 or counter electrode 105 may be at or about 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.5, 0.6, 0.7, 0.8, 0.9, 1, 1.1, 1.2, 1.3, 1.4, 1.5, 1.6, 1.7, 1.8, 1.9, 2, 3, 4, 5, 6, 7, 8, 9, 10 V, etc. In embodiments, the bias voltage applied may be within a range formed by selecting any two numbers (two voltage values) listed in the immediately previous sentence, e.g., between about 0.05 V and about 0.10 V, between about 0.20 V and about 0.30 V, between about 0.30 V and about 0.40 V, between about 0.28 V and about 0.40 V, between about 0.30 V and about 0.38 V, between about 0.28 V and about 0.36 V, between about 0.45 V and about 0.50 V, etc.

Glucose Sensitivity and Accuracy of CGM Sensor

The glucose sensitivity of CGM sensors can vary depending on the specific design and materials used. CGM sensors are generally less accurate than blood glucose meters, which should deliver measurements within ±15% of a highly precise lab measurement 95% of the time, and within ±20% 99% of the time according to FDA guidelines.

Sensitivity Deterioration Over Use

Over time, CGM sensor's sensitivity to glucose can change due to factors like the natural wear and tear of the sensor materials and the body's immune response to the sensor. For example, glucose-specific enzymes can degrade over time. Also, the body's immune system can react to the sensor as a foreign object, causing tissue changes around the sensor that can affect its accuracy. Predicting changes in CGM sensor sensitivity is challenging due to factors such as the rate of sensor material degradation, biological variability of person's body, and environmental factors like temperature, pH, etc.

Calibration of CGM Systems

When the sensitivity of an electrochemical CGM sensor deteriorates, the electric current from glucose oxidation becomes smaller even if the glucose concentration stays the same. Considering the complex nature of predicting the changes, calibration techniques have been used to make the CGM measurements more accurate. Manual Calibration involves users performing finger prick tests and entering blood glucose values into the CGM system. Alternatively, factory calibration allows users to use CGM sensors without finger prick tests.

Factory Calibration

Factory calibration typically involves batch testing and calibration algorithms. During production, sensors from each batch are tested against known glucose concentrations. The data collected from these tests are used to determine how the sensor's electrical signals correspond to actual glucose levels. The correlation between the electrical current generated by the CGM sensor and the glucose concentration is embedded into the sensor's memory. The embedded calibration data is used by the sensor's algorithms to continuously adjust and ensure accurate glucose readings over time. The factory calibration is conducted batch by batch, and sensors in each batch should have a similar deterioration rate and/or sensitivity. In the meantime, a user usually uses the same type of sensor repeatedly and thus produces user specific data for the sensor they use. Factory calibration data by batch is often combined with such user specific data to further improve the calibration.

Nanoporous Layer for Glucose Sensing

Nanoporous Layer

The nanoporous layer 117 for the working electrode 103NE includes nano-size internal structures such as cavities, spaces and openings (collectively "nano-pores" or "nanopores"). Overall, the nanoporous layer 117 is conductive. When a voltage is applied to the working electrode and the reference electrode or the counter electrode, electrons travel between the electrodes and inside the nanoporous layer of the working electrode. In the meantime, glucose can travel generally inside the nanoporous layer via the nanopores inside the nanoporous layer and can be oxidized generally anywhere in the nanoporous layer. In embodiments, nanopores of the nanoporous layer 117 enable or facilitate oxidation of glucose, and glucose concentration can be measured based on electric current caused by glucose oxidation. Although any aspects of the invention are not bound by any theory or belief, it is conceivable that glucose oxidation occurs when glucose molecules enter nanopores and contact internal surfaces more often and for a longer time in the nanoporous layer 117 than on a non-porous surface of an electrode.

No Enzyme and No Electron Mediator

With the incorporation of the nanoporous layer 117, the working electrode 103NE can be provided without a glucose-specific enzyme that requires more complex fabrication processes and is less stable than the solid-state material of the nanoporous layer 117. Further, the working electrodes 103NE can operate without an electron mediator that facilitates electron transfers between different materials. In embodiments, the working electrode 103NE includes neither an enzyme nor an electron mediator.

Materials for Nanoporous Layer

In some embodiments, the nanoporous layer 117 is made of or includes platinum (Pt), gold (Au), palladium (Pd), rhodium (Rh), titanium (Ti), chrome (Cr), ruthenium (Ru), tin (Sn), nickel (Ni), copper (Cu), indium (In), thallium (Tl), zirconium (Zr), iridium (Ir), or an oxide of the foregoing elements, although not limited thereto. In other embodiments, the nanoporous layer 117 is made of or includes an alloy material of two or more of the metal elements listed in the previous sentence including Pt—Ir, Pt—Ru, Pt—Pd, although not limited thereto.

Nanoparticles

The nanoparticles 121 in the nanoporous layer 117 are discrete and generally in a spherical (ball-like) or oval (egg-like) shape, although not limited thereto. The nanoparticles may have a diameter from less than about 1 nm, about 1 to about 100 nm, or greater than about 100 nm, such as at or about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 90, 91, 92, 93, 94, 95, 96, 97, 98, 99, 100 101, 102, 103, 104, or 105 nm, etc. In embodiments, the diameter of the nanoparticles may be within a range formed by selecting any two diameter values listed in the immediately previous sentence, such as from about 0.8 to 1 nm, from about 10 to about 50 nm, from about 50 to about 100 nm, from about 1 to 10 nm, from about 2 nm to about 5 nm, or from about 95 to 105 nm, etc. The nanoparticles may have a mean diameter less than about 2 nm, from about 2 to about 5 nm, or greater than 5 nm, such as at or about 1, 1.5, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.10, 4.15, 4.2, 4.25, 4.3, 4.35, 4.4, 4.45, 4.5, 4.55, 4.6, 4.65, 4.7, 4.75, 4.8, 4.85, 4.9, 4.95, 5, 6, 7, 8, 9, or 10 nm, etc. In embodiments, the mean diameter of the nanoparticles may be within a range formed by selecting any two numbers listed in the immediately previous sentence, e.g., between about 1.5 nm and about 3.5 nm, between about 2.5 nm and about 4.0 nm, between about 2.75 nm and about 3.75 nm, between about 2.25 nm and about 3.5 nm, between about 3 nm and about 6 nm, etc. In embodiments, nanoparticles having a mean diameter of 2-5 nm are found throughout the nanoporous layer 117.

Nanoparticle Size Distribution

The size of the nanoparticles may be generally homogeneous. The nanoparticles may also exhibit a variety of particle size distributions depending on their synthesis methods, environmental conditions, and post-processing treatments. Their small size and high surface area make them particularly sensitive to factors such as agglomeration, growth kinetics, and dispersibility, leading to different distribution patterns. For example, the nanoparticles can follow a normal (Gaussian) distribution, where most particles are concentrated around an average size with fewer extremes on either end. The nanoparticles may have a log-normal distribution, where a larger number of small particles exist alongside a few larger aggregates. The nanoparticles may display bimodal or multimodal distributions, where two or more distinct size populations exist.

Binder for Nanoporous Layer

In some embodiments, the nanoporous layer 117 may include a binder. The selection of a binder depends on factors like desired mechanical, thermal, and electrical properties; compatibility with metal nanoparticles; and application-specific requirements, such as conductivity, flexibility, or environmental stability. In other embodiments, no binder is used in the nanoporous layer 117.

Thickness of Nanoporous Layer

In embodiments, the thickness of nanoporous layer 117 may be less than 1 μm, from about 1 μm to about 1 mm, or greater than 1 mm, such as at or about 100, 200, 300, 400, 500, 600, 700, 800, 900 nm, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μm, 1.1, 1.2, 1.3, 1.4, 1.5, 1.6, 1.7, 1.8, 1.9, or 2 mm, etc. In some embodiments, the thickness may be within a range formed by selecting any two numbers (two thickness values) listed in the immediately previous sentence, e.g., between about 500 nm and about 1 μm, between about 1 μm and about 10 μm, between about 50 μm and about 80 μm, or between about 10 μm and about 400 μm, between about 1 mm and about 1.5 mm, etc.

Nanoparticle Clusters

In a nanoparticle suspension or colloid, nanoparticles are not always evenly dispersed as isolated entities; rather, they can form temporary clusters due to various interactions such as van der Waals forces, electrostatic forces, or steric effects. These clusters are a transient phenomenon, meaning they exist only while the nanoparticles are suspended in a liquid medium. Once the suspension dries and a nanoporous layer is formed, these clusters no longer exist in the same way. The drying process removes the solvent, leading to a structural rearrangement of the nanoparticles. Any previous clustering in the liquid phase does not necessarily dictate the final solid-state arrangement, as particle-particle interactions change upon solvent evaporation. It is important to note that the term "clusters" is used only for conceptual clarity and does not imply permanent aggregates or solid-phase structures. The observed clustering in suspension is a dynamic and reversible process, governed by the balance of repulsive and attractive forces, and does not persist in the final nanoporous layer.

Making Nanoparticle Clusters

The nanoporous layer 117 may be prepared using a liquid composition that contains metal ions and a surfactant. In embodiments, different morphologies of the nanoporous layer may be formed using different phases of the surfactant. A micelle phase, a reverse micelle phase, a liquid crystalline phase or another phase of the surfactant may be used to produce the nanoporous layer in a particular morphology. In these different phases, the metal ions are locally concentrated next to hydrophilic moieties of the surfactant in the liquid composition. When adding a reducing agent, the localized metal ions in the liquid composition form metal nanoparticles. Subsequently, a process to remove the surfactant follows to provide a liquid suspension or colloid of irregularly shaped clusters of metal nanoparticles. This process is discussed in more detail in U.S. Pat. No. 11,717, 199, which is incorporated by reference in its entirety herein.

Size of Nanoparticle Clusters

The number of nanoparticles 121 in each cluster may vary wildly, and the size of clusters 125 may vary accordingly. In some embodiments, some clusters 125 are nano-sized (for example, smaller than 100 nm), and others are micro-sized (from example, 100 nm to 200 μm). The clusters 125 have a length or diameter of less than about 20 nm, from about 20 nm to about 200 μm, or greater than about 200 μm, such as at or about 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700, 800, 900 nm, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 μm, etc. In embodiments, the length or diameter of the clusters 125 may be within a range formed by selecting any two numbers (two length or diameter values) listed in the immediately previous sentence, e.g., between about 20 nm and about 300 nm, between about 60 nm and about 240 nm, between about 20 μm and about 100 μm, between about 50 μm and about 200 μm, etc. The clusters 125 may have a mean diameter or length of less than about 20 nm, from about 20 nm to about 200 μm, or greater than about 200 μm, such as at or about 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700, 800, 900 nm, 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 μm, etc. In embodiments, the mean diameter of the clusters 125 may be within a range formed by selecting any two numbers listed in the immediately previous sentence, e.g., between about 100 nm and about 220 nm, between about 20 μm and about 200 μm, between about 50 μm and about 100 μm, etc.

Forming Nanoporous Layer

In embodiments, the liquid suspension or colloid with or without adjusting concentration is dispensed on the substrate, which is subject to drying. As the liquid dries off, clusters are spontaneously deposited over the substrate and over other clusters. There may be no external force applied to the clusters while drying. Accordingly, the clusters do not get packed as they deposit. As clusters deposit and stack over other clusters, each cluster may contact the substrate surface or neighboring clusters. After completion of drying, the clusters abut or contact adjacent or neighboring clusters. The deposited clusters are interconnected or integrated via the abutments and contacts. Due to the irregular shapes of individual clusters, irregularly shaped gaps and spaces are formed between adjacent clusters, in which the gaps and spaces define the irregular shapes of the deposited clusters as if the surfaces and contours of deposited clusters are surrounded by the irregularly shaped gaps and spaces. The irregularly shaped gaps and spaces are referred to as intercluster gaps or spaces 127.

Illustration of Clusters

Figure 3A:
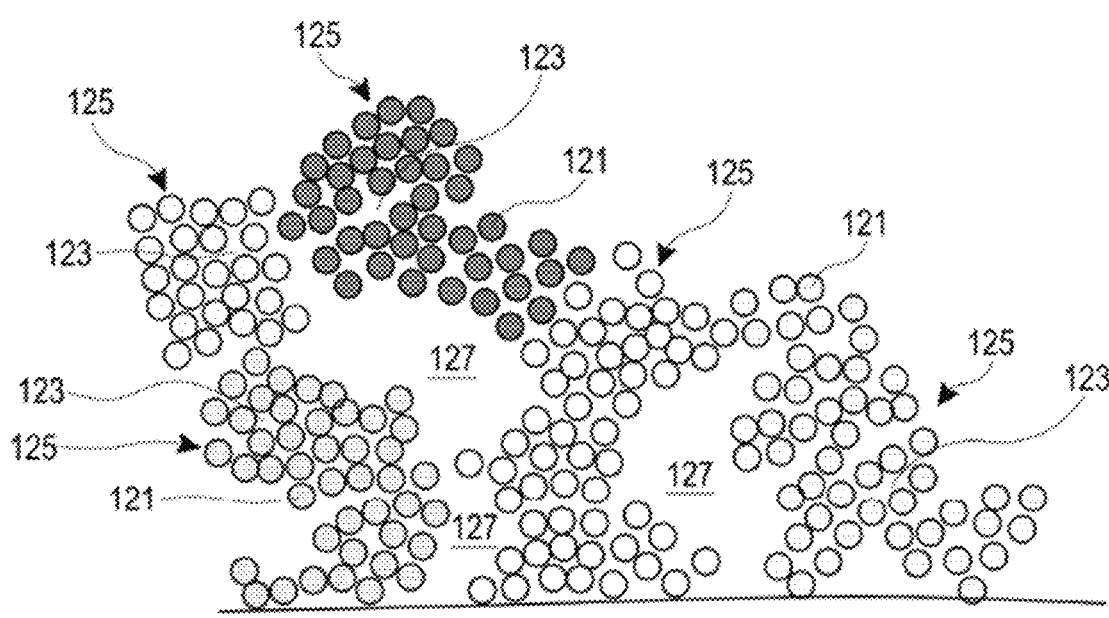
FIGS. 3A and 3B illustrate nanoparticle clusters in a nanoparticle suspension or colloid on a top surface of the substrate and the morphology of the nanoporous layer according to some embodiments.
Figure 3B:
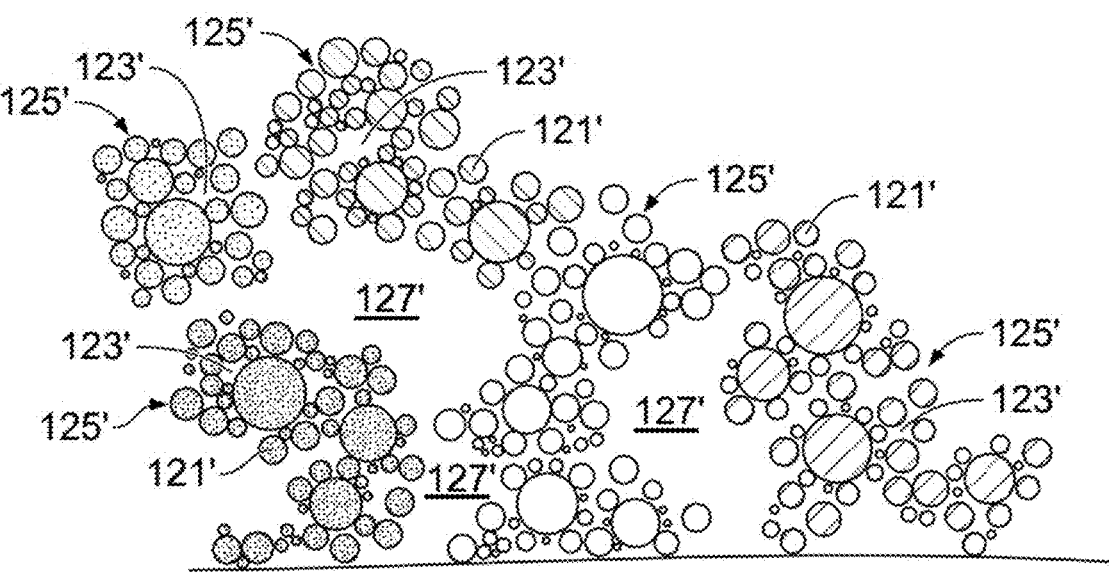
Figure 4A:
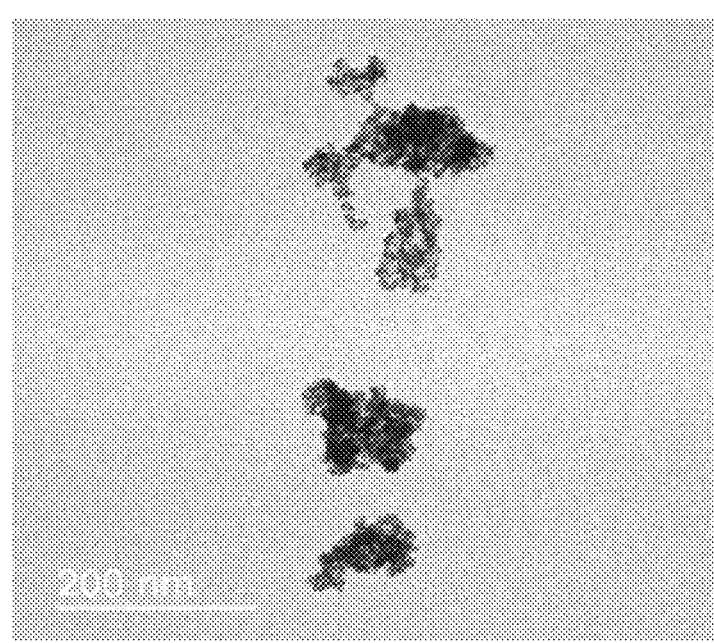
FIG. 4A is a TEM photographic image of clusters according to an embodiment.
Figure 4B:
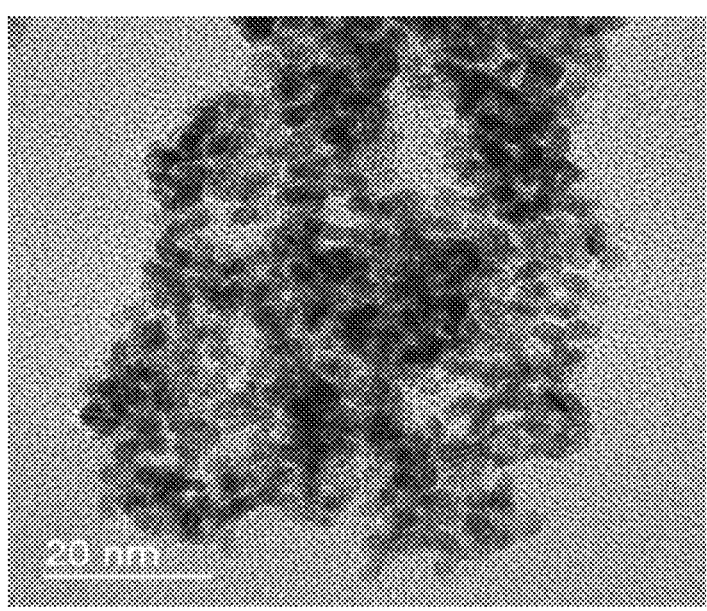
FIG. 4B is a zoomed-in image of the TEM photographic image of FIG. 4A.
Figure 4C:
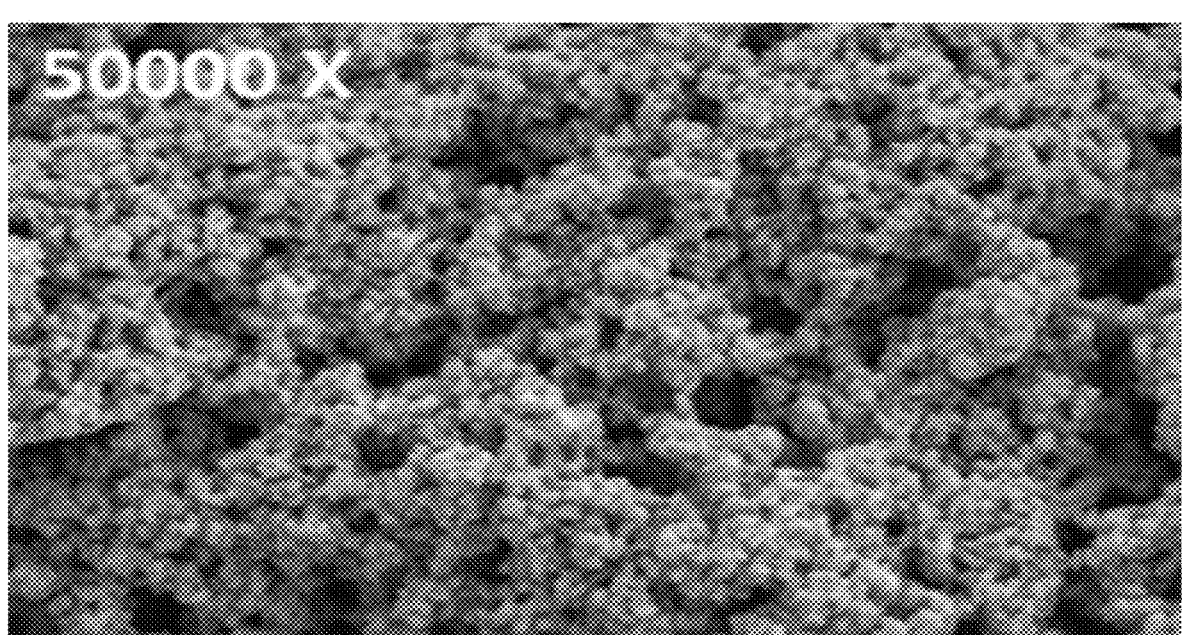
FIG. 4C is an SEM photographic image of a nanoporous layer taken from its top according to an embodiment.

FIGS. 3A and 3B are illustrations of the nanoparticle clusters in the suspension or colloid when the suspension or colloid is put, dispensed, sprayed, deposited, placed, or coated (or whatever other procedures) onto a top surface of the substrate. In nano-sized reality, the top surface of the substrate may not be as straight as illustrated and may be bumpy. As illustrated in FIG. 3A, a number of nanoparticles 121 get together and form irregularly shaped clusters 125. For the sake of illustration, different shadings or hatchings are used in different clusters 125. These irregularly shaped clusters 125 are stacked irregularly to form the nanoporous layer. FIG. 3A illustrates an embodiment in which the sizes of the nanoparticles are generally homogenous. It is understood that the sizes of the nanoparticles can vary in other embodiments, such as the one illustrated in FIG. 3B. FIG. 4A is a transmission electron microscope (TEM) photographic image of some clusters 125 before they deposit to form a nanoporous layer. FIG. 4B is a zoomed-in image of a portion of FIG. 4A. FIG. 4C is a scanning electron microscope (SEM) photographic image of a nanoporous layer having a clustered morphology taken from the top of the nanoporous layer. When the nanoparticle suspension or colloid is dried on top of the substrate, the nanoparticles and clusters may experience structural rearrangement, but it is understood that FIGS. 3A and 3B still generally illustrate the morphology of the formed nanoporous layer in some embodiments.

Morphologies of Nanoporous Layer

The nanoporous layer 117 may have different internal morphologies in each specific manufacture. In some embodiments, the nanoporous layer 117 may include or be made of nanoparticles deposited together forming nanopores among themselves (interparticular nanopores). In other embodiments, the nanoporous layer 117 may include interparticular nanopores and also spaces among clusters (intercluster gaps or spaces). In other embodiments, the nanoporous layer 117 may include or be made of repetition of a specific shape of nanostructure such as hexagonal structure that includes nanopores therein. Also, in each specific manufacture, the nanoporous layer 117 may have different levels of porosity and different roughness factor values per unit volume.

Distribution of Clusters and Intercluster Gaps

In embodiments, the irregularly shaped cluster bodies 125 are distributed throughout the clustered morphology of the nanoporous layer 117. The irregularly shaped cluster bodies 125 are interconnected via abutments, which means these cluster bodies contact themselves and form a three-dimensional network of cluster bodies generally throughout the nanoporous layer 117. The intercluster gaps 127 define and surround surfaces of the irregularly shaped cluster bodies and are interconnected themselves to form a three-dimensional interconnected or networked channels throughout the nanoporous layer 117. The intercluster gaps and spaces 127 are well distributed throughout the nanoporous layer 117 from the top (not shown) to the bottom (on or immediately above the substrate). The three-dimensional network of cluster bodies and channels may be similar to the three-dimensional internal shapes of a sponge except that the interparticular gaps and spaces are networked together throughout the nanoporous layer 117.

Distribution of Nanoparticles and Interparticular Nanopores

Given that each cluster is formed with many nanoparticles 121 and interparticular nanopores 123, the nanoparticles 121 and interparticular nanopores 123 are distributed generally throughout the nanoporous layer 117. Accordingly, interparticular nanopores 123 are interconnected within each cluster and interconnected with interparticular nanopores of other clusters generally throughout the nanoporous layer 117 via interparticular nanopores in abutments between clusters and via intercluster gaps 127 that are interconnected throughout the nanoporous layer 117.

Intercluster Gaps/Spaces for Diffusion of Glucose

The glucose molecules can travel inside the nanoporous layer through the irregular-shaped intercluster gaps and spaces 127 that are interconnected generally three-dimensionally and can be oxidized anywhere in the nanoporous layer. In embodiments, the interconnection of intercluster gaps 127 provides networked channels for diffusion of glucose molecules (0.7-0.8 nm long) within the nanoporous layer 117. It is understood that glucose oxidation occurs primarily in nano-sized interparticular nanopores rather than in micro-sized spaces. As the intercluster gaps 127 are networked or interconnected three-dimensionally generally throughout the nanoporous layer 117, glucose molecules can travel through these intercluster gaps 127 and enter the interparticular nanopores 123 anywhere in the nanoporous layer. The glucose molecules thus may reach almost anywhere in the nanoporous layer 117 via the intercluster spaces that are large scale considering the size of glucose molecules. Also, as the intercluster gaps 127 are well interconnected to the interparticular nanopores 123, interparticular nanopores 123 anywhere in the nanoporous layer 117 may be exposed and open for glucose oxidation. Accordingly, the three-dimensional interconnected or networked channels of the intercluster gaps may provide more glucose oxidation, i.e., stronger signals (higher electric current) of the glucose oxidation than a nanoporous layer without such interconnected channels formed of intercluster gaps.

Two Types of Particles and Two Types of Pores

As discussed, the clustered morphology 120 includes two different types of particles defining two different types of pores. In terms of particles, one is the nanoparticles 121, and the other is the clusters 125 made of nanoparticles 121. In terms of pores, one is the interparticular nanopores 123 between nanoparticles 121 within a cluster 125, and the other is the intercluster gaps 127 between clusters 125.

Interparticular Nanopores

The TEM photographic image of FIG. 4B also shows interparticular nanopores between nanoparticles in the cluster. The interparticular nanopores may be networked and interconnected within the cluster. The interparticular gaps or nanopores 123 have an interparticular gap distance that may be less than about 0.5 nm, from about 0.5 nm to about 70 nm, or greater than about 70 nm, such as at or about 0.1, 0.15, 0.2, 0.25, 0.3, 0.35, 0.4, 0.45, 0.5, 0.55, 0.6, 0.65, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.1, 2.15, 2.2, 2.25, 2.3, 2.35, 2.4, 2.45, 2.5, 2.55, 2.6, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nm, etc. In embodiments, the interparticular gap distance may be within a range formed by selecting any two numbers (two distance values) listed in the immediately previous sentence, e.g., between about 0.5 nm and about 4.5 nm, between about 1.5 nm and about 4.0 nm, between about 1 nm and about 50 nm, between about 2 nm and about 10 nm, or between about 50 nm and about 70 nm, etc. The interparticular nanopores 123 may have a mean interparticular gap distance that may be less than about 0.5 nm, from about 0.5 nm to about 70 nm, or greater than about 70 nm, such as at or about 0.1, 0.15, 0.2, 0.25, 0.3, 0.35, 0.4, 0.45, 0.5, 0.55, 0.6, 0.65, 0.75, 0.8, 0.85, 0.9, 0.95, 1.0, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2.0, 2.1, 2.15, 2.2, 2.25, 2.3, 2.35, 2.4, 2.45, 2.5, 2.55, 2.6, 2.7, 2.75, 2.8, 2.85, 2.9, 2.95, 3.0, 3.05, 3.1, 3.15, 3.2, 3.25, 3.3, 3.35, 3.4, 3.45, 3.5, 3.55, 3.6, 3.65, 3.7, 3.75, 3.8, 3.85, 3.9, 3.95, 4.0, 4.05, 4.1, 4.15, 4.2, 4.25, 4.3, 4.35, 4.4, 4.45, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nm, etc. In embodiments, the mean interparticular gap distance of the nanopores 123 may be within a range formed by selecting any two numbers listed in the immediately previous sentence, e.g., between about 0.75 nm and about 1.5 nm, between about 1.0 nm and about 2.5 nm, between about 1 nm and about 50 nm, between about 2 nm and about 10 nm, or between about 30 nm and about 50 nm, etc. In embodiments, interparticular nanopores 123 having a mean interparticular gap distance of 1-2.5 nm may be found throughout the nanoporous layer 117.

Size Distribution of Interparticular Nanopores

The sizes of the interparticular nanopores may be generally homogeneous. The interparticular nanopores may also exhibit a variety of particle size distributions. For example, the interparticular nanopores can follow a normal (Gaussian) distribution, where most interparticular nanopores are concentrated around an average size with fewer extremes on either end. The interparticular nanopores may have a log-normal distribution, where a larger number of small particles exist alongside a few larger aggregates. The interparticular nanopores may display bimodal or multimodal distributions, where two or more distinct size populations exist.

Intercluster Gaps/Spaces

The SEM photographic image of FIG. 4C shows openings of the networked intercluster gaps that can be seen from the top of the nanoporous layer. Although the three-dimensional shapes are not well presented in the two-dimensional image of FIG. 4C, the top surface of nanoporous layer includes valleys and hills formed by stacked clusters. Inside the nanoporous layer, the valleys and hills form the intercluster gaps. The intercluster gaps or spaces may be in irregular shapes. The intercluster gaps 127 may be nano-sized to micro-sized. The intercluster gaps 127 may have an intercluster gap distance that is less than about 10 nm, from about 10 nm to about 50 μm, or greater than about 50 μm, such as at or about 5, 6, 7, 8, 9, 10, 15, 20, 25, 30, 35, 40, 45, 50, 55, 60, 65, 70, 75, 80, 85, 90 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 nm, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 μm, etc. In embodiments, the intercluster gap distance may be within a range formed by selecting any two numbers listed in the immediately previous sentence, e.g., between about 100 nm and about 1000 nm, between about 20 nm and about 100 nm, between about 200 nm and about 800 nm, between about 10 μm and about 20 μm, between about 20 μm and about 25 μm, between about 30 μm and about 40 μm, or between about 15 μm and about 30 μm, etc. The intercluster gaps 127 may have a mean intercluster gap distance that is less than about 10 nm, from about 10 nm to about 50 μm, or greater than about 50 μm, such as at or about 5, 6, 7, 8, 9, 10, 15, 20, 25, 30, 35, 40, 45, 50, 55, 60, 65, 70, 75, 80, 85, 90 95, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 nm, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 μm, etc. In embodiments, the mean intercluster gap distance may be within a range formed by selecting any two numbers listed in the immediately previous sentence, e.g., between about 150 nm and about 400 nm, between about 50 nm and about 100 nm, between about 20 nm and about 200 nm, between about 300 nm and about 900 nm, between about 5 μm and about 25 μm, between about 15 μm and about 35 μm, between about 35 μm and about 55 μm, or between about 20 μm and about 35 μm, etc.

Size Distribution of Intercluster Gaps/Spaces

The sizes of the intercluster gaps/spaces may be generally homogeneous. The intercluster gaps/spaces may also exhibit a variety of particle size distributions. For example, the size of the intercluster gaps/spaces can follow a normal (Gaussian) distribution, where most intercluster gaps/spaces are concentrated around an average size with fewer extremes on either end. The size of the intercluster gaps/spaces may have a log-normal distribution, where a larger number of small particles exist alongside a few larger aggregates. The size of the intercluster gaps/spaces may display bimodal or multimodal distributions, where two or more distinct size populations exist. The size of the intercluster gaps/spaces may display some other types of distributions, one or more types of distributions, and/or random distributions.

Glucose Sensitivity of Nanoporous Layer

Glucose Oxidation on Surfaces of Metal Nanoparticles

When a glucose sensor is inserted in a subject's body and contacts the interstitial fluid of the subject, glucose molecules in the interstitial fluid may travel to the metal nanoporous layer 117, in which the glucose molecules travel through the intercluster spaces 127 to reach the interparticular nanopores 123 and the metal nanoparticles 125. When a voltage is applied on the working electrode 105, the glucose molecules are oxidized at or near the surfaces of the metal nanoparticles. While not bound by any theory or belief, it is conceivable that glucose oxidation occurs or is likely when glucose molecules enter interparticular nanopores 123 and contact internal surfaces multiple times and stay there for an extended period of time in the nanoporous layer 117. Electrons from glucose oxidation travels to the electrically conductive substrate 110 of the working electrode to generate electric current, which is measured by the current sensor 108.

Current Measured by Sensor and Glucose Sensitivity of Sensor

The magnitude of this current may be proportional to the net electrochemical reactions occurring in the glucose sensor including the glucose oxidation and other redox reactions. With electric signal processing, one can obtain an electrical current proportional to only glucose oxidation which should be proportional to the glucose concentration in the interstitial fluid. However, as discussed above, the glucose sensitivity of the sensor can change and in fact deteriorate over time during which the sensor is in contact with the interstitial fluid. Thus, the current from glucose oxidation may not accurately indicate the glucose concentration in the interstitial fluid. Also, the glucose sensitivity change may have different time profiles for different sensors even if they are in contact with the identical interstitial fluid. To accurately determine the glucose concentration based on the electric current measured by the sensor, one must know the glucose sensitivity of the sensor at the time of the current measurement.

Determining Glucose Sensitivity from Current and Concentration

The value of the current generated from glucose oxidation can be used to obtain the glucose sensitivity of the sensor at the time of measuring the current. As glucose concentration increases, more glucose molecules undergo oxidation at the electrode surface, leading to a greater flow of electrons and, consequently, a higher current. Conversely, when glucose levels decrease, fewer oxidation reactions occur, resulting in a lower current. This direct correlation allows real-time glucose measurement based on the strength of the generated current.

Method of Determining Glucose Sensitivity from Current and Concentration

Figure 10:
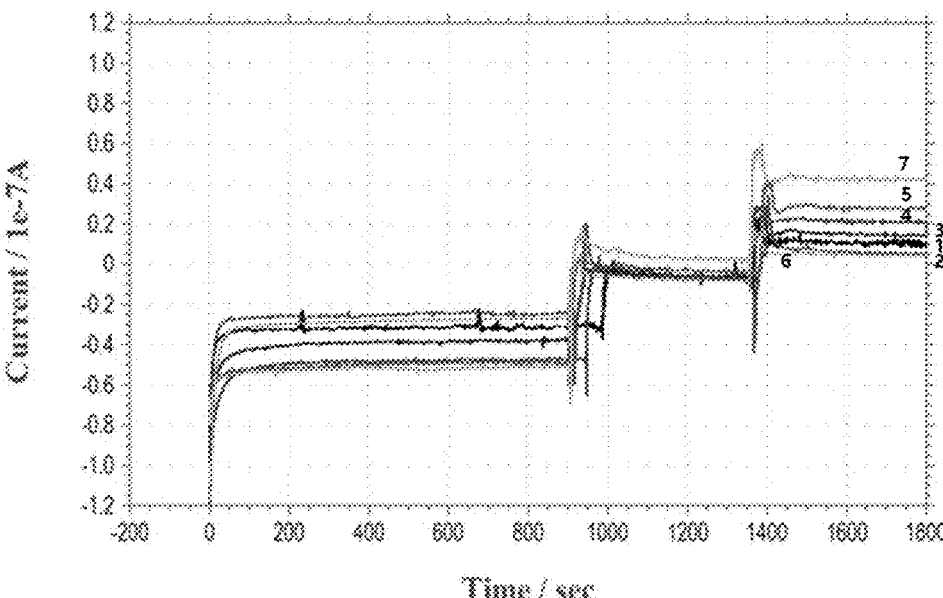
FIG. 10 is a graph showing sensor current signals over time of the sensors in PBS (phosphate buffered saline) solution in Example 2.19.

To determine glucose sensitivity of sensors with the same characteristics, multiple glucose solutions with known concentrations are prepared, and the current response for each glucose concentration when the sensor is placed in each glucose solution is measured at a fixed potential. The current response (y-axis) can be plotted against the glucose concentration (x-axis) to obtain a calibration curve. The sensitivity of the sensor is determined from the slope of the linear portion of the calibration curve. Mathematically, it can be expressed as:

$$\text{Sensitivity} = \frac{\Delta I}{\Delta C},$$

where $\Delta I$ is the change in current and AC is the change in glucose concentration. The sensitivity is usually expressed in units of current per concentration, such as μA/mM, nA/μM, nA/mM, etc. Example 2 and FIG. 10 illustrate how the glucose sensitivity is obtained as described herein. This glucose sensitivity obtained from the current and glucose concentration data is considered the "actual" glucose sensitivity, as compared to the "calculated" glucose sensitivity obtained from the impedance and its correlation with the glucose sensitivity as described later in this disclosure.

Effective Surface Area of Nanoporous Layer

Assuming that glucose molecules are oxidized on or adjacent the surfaces of the metal nanoparticles, it is conceivable that there is a correlation between the surface area of metal nanoparticles available for glucose oxidation and the glucose sensitivity of CGM sensors using the metal nanoparticles. In other words, the more surface areas of the metal nanoparticles, the more likely the glucose oxidation can occur when the glucose sensor contacts liquid with the same glucose concentration. This surface area of the metal nanoparticles available for and capable of oxidizing glucose molecules is referred to as the effective surface area of the metal nanoporous layer. Generally, a larger effective surface area of the metal nanoporous layer provides more opportunity for glucose molecules to interact with the metal nanoparticles, allowing more glucose molecules to be oxidized and detected. Thus, the glucose sensitivity of the sensor is considered proportional to the effective surface area of the nanoporous layer.

Obtaining Effective Surface Area

The effective surface area of the nanoporous layer can be obtained by cyclic voltammetry (CV), as illustrated in Example 3 and FIG. 7. CV is an electrochemical technique used to study the redox properties of chemical compounds. It involves sweeping the potential of a working electrode linearly with time and then reversing the direction to return to the initial potential, creating a cyclic pattern. This process is repeated multiple times to obtain a cyclic voltammogram, which plots current versus potential. The charge of the hydrogen adsorption peak in CV is used to calculate the effective surface area of the nanoporous layer in the working electrode.

Hydrogen Evolution Reaction

The charge of the hydrogen adsorption peak is proportional to the effective surface area of the nanoporous layer. In CV, the hydrogen evolution reaction (HER) is a key electrochemical process where hydrogen gas is produced from water. HER typically occurs in two main steps: Volmer step: $H3O++e-\rightarrow Hads+H2O$; Tafel step: $2Hads\rightarrow H2$, and alternatively, the Heyrovsky step can occur: $Hads+H3O++e-\rightarrow H2+H2O$. In CV, the potential is swept linearly, and the current response is recorded. For HER, the current increases sharply at a certain negative potential, indicating the onset of hydrogen evolution. When hydrogen adsorbs onto a platinum electrode, it forms a monolayer. The charge associated with this adsorption process—indicated by the hydrogen adsorption peak—can be measured using CV.

Calculating Effective Surface Area

The charge of the hydrogen adsorption peak is proportional to the hydrogen adsorption area and thus the effective surface area of the nanoporous layer. The effective surface area can be calculated by dividing the integrated charge— the area under the hydrogen adsorption peak in the CV—by the charge density of the metal material used in the nanoporous layer. The charge density represents the amount of charge required to form a complete monolayer of hydrogen on the surface of the metal nanoporous layer. The choice of the mental material can significantly affect the HER activity in CV. For example, platinum (Pt) is often used due to its high catalytic activity. Typically, the charge density for hydrogen adsorption on a platinum electrode is around 210 $\mu C/cm^2$ per monolayer of hydrogen. Thus, the surface area of a Pt nanoporous layer can be calculated by dividing the integrated charge (Q)—the integrated area under the hydrogen adsorption peak in the CV—by the charge density (210 $\mu C/cm^2$):

$$\frac{Q}{210\ \mu C/cm^2},$$

as illustrated in Example 3.9.

Electrical Double Layer Capacitance

Ions in the interstitial fluid may be attracted to the surfaces of the nanoparticles and form a charged layer over nanoparticle surfaces. Simultaneously, a second layer of opposite charge forms in the interstitial fluid adjacent to the first layer. This electric double layer behaves like a capacitor, storing electrical charge, and the capacity of the double layer to store charges is measured by the electrical double layer capacitance, in farads (F). This electrical double layer capacitance is proportional to the effective surface area of the nanoporous layer. Further, changes in the effective surface area are reflected on changes in electrical signals generated by glucose oxidation on the surfaces of the nanoparticles. Thus, the electrical double layer capacitance is proportional to the glucose sensitivity of the nanoporous layer sensor.

Impedance

The correlation between the electrical double layer capacitance and the glucose sensitivity of the nanoporous layer sensor can be determined through the correlation between impedance of the sensor system in the interstitial fluid and the sensor's glucose sensitivity. Impedance, denoted as Z, is the total opposition that a circuit presents to the flow of alternating current (AC). It is a combination of resistance (R) and reactance (X), and it is measured in ohms (Ω). Impedance can be represented as a complex number, having both magnitude and phase.

Capacitance and Impedance in AC Circuits

In general, the impedance is vector $Z=R-jX_C$, where R is the resistance and XC is the capacitive reactance. j is the imaginary unit, $\sqrt{-1}$. In general, the impedance can be represented as $$Z(\omega)=Z_{Re}-jZ_{Im}$$

where $Z_{Re}$ and $Z_{Im}$ are the real and imaginary part of the impedance, respectively. Here, $Z_{Re}=R$, where R is the resistance (ohm) and $Z_{Im}=X_C=1/\omega C$, where $\omega=2\pi f$, and $\omega$ is the angular frequency, f is the frequency, and C is the capacitance in farads (F). The magnitude of Z is given by $$|Z|=\sqrt{R^2+X_C^2}$$

Capacitive reactance decreases with increasing frequency, meaning capacitors oppose low-frequency signals more than high-frequency signals.

Capacitance and Impedance in DC Circuits

When a capacitor is connected to a direct current (DC) voltage source, $X_C=1/2\pi f$ is infinite since f=0.

Electrochemical Impedance Spectroscopy

Figure 13:
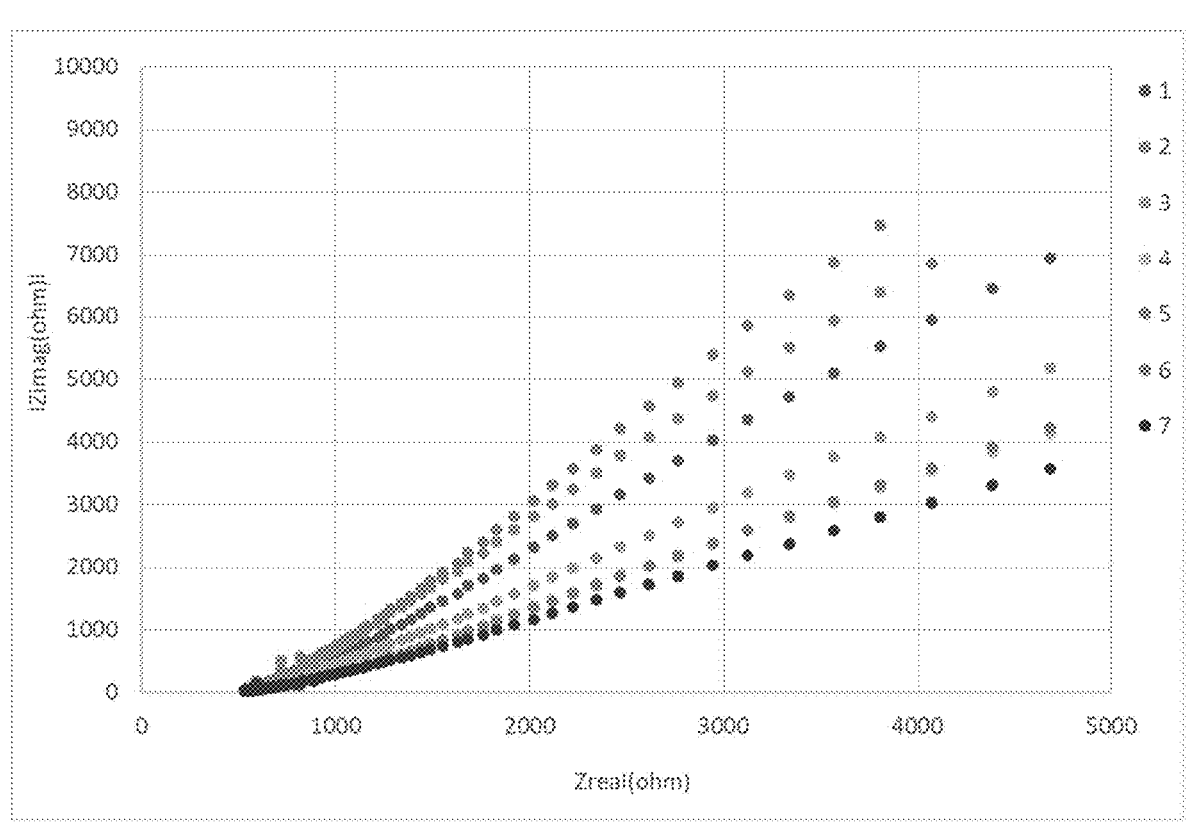
FIG. 13 is Nyquist plot for seven nanoporous layer electrodes used in FIGS. 11A-11C according to an embodiment.

EIS may be deployed for determination of impedance. EIS is a technique widely used to test the electrical properties of chemical systems. A potentiostat can be used to apply a sinusoidal AC potential added on DC potential to the electrode such as the nanoporous layer sensor, and the response of the electrode can be measured as a function of frequency and be analyzed. Alternatively, a galvanostat can be used to control the current and to measure and analyze the response. The amplitude of the AC signal is small enough to maintain linearity in the system's response. The measurements are taken over a range of frequencies, and the resulting data is analyzed to determine the impedance of the system such as the real part impedance (ZRe), the imaginary impedance (ZIm), and the phase angle (φ). In a Nyquist Plot, as illustrated in FIG. 13, the imaginary part (ZIm) is plotted against the real part (ZRe) to visualize the impedance at different frequencies and identify different electrochemical processes. In a Bode Plot, the magnitude and phase angle of impedance are plotted against the frequency to show how the impedance and phase shift vary with frequency. The phase angle (φ) is calculated as $$\tan\phi=Z_{Im}/Z_{Re}=X_C/R=1/\omega RC$$

The EIS thus provides insights into the electrochemical processes and properties, including the electrical double layer capacitance of the nanoporous layer sensor system in the interstitial fluid.

Impedance and Frequency: Self-Resonant Frequency (SRF)

It is important to find the self-resonant frequency (SRF) of the nanoporous layer electrical double-layer in EIS. The SRF of a capacitor is the frequency at which the capacitor's impedance is at its minimum, and it transitions from behaving like a capacitor to behaving like an inductor. Below the SRF, the capacitor primarily exhibits capacitive behavior, and the impedance (Z) is dominated by the capacitive reactance (XC); and the capacitor behaves as expected, with impedance decreasing with increasing frequency. Above the SRF, the capacitor behaves more like an inductor, with impedance increasing with frequency. Knowing the SRF helps ensure that impedance measurements are accurate and reflect the true capacitive behavior of the nanoporous layer electrical double-layer. Operating near or above the SRF can lead to incorrect interpretations of the impedance data. By identifying the SRF, these frequencies can be avoided, and reliable EIS measurements can be ensured. In a plot of the imaginary part of impedance (ZIm) against frequency, the SRF can be identified by looking for the point where the imaginary part crosses zero, which is the point where the impedance changes from negative (capacitive behavior) to positive (inductive behavior).

Equivalent Circuit

Figure 6:
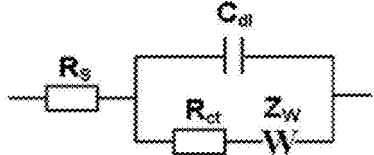
FIG. 6 illustrates a Randles equivalent circuit.

An electrochemical cell comprising electrodes and electrolyte solution can be considered as impedance to a small sinusoidal excitation. Thus, the performance of the electrochemical cell can be represented by an equivalent circuit of resistors and capacitors that pass current with the same amplitude and phase angle that the real cell does under a given excitation. For example, a Randles equivalent circuit, as shown in FIG. 6, represents the electrochemical cell with the double layer capacitance (Cdl), the charge transfer resistance (Rct), the Warburg impedance (Zw) which is a kind of resistance to mass transfer, and the electrolyte resistance (Rs).

Impedance of Nanoporous Layer Electrode

The impedance of a nanoporous platinum layer electrode, ID-npPt, is given by Equation 1:

$$Z=\sqrt{r/K(j\omega)^\alpha}\coth(l\sqrt{rK(j\omega)^\alpha})\qquad\text{(Equation 1)},$$

where r is electrolyte resistance in the pores ($\Omega cm^{-1}$), K is a constant analogous to capacitance (F), l is film thickness (cm), and $\alpha$ is a constant. When Equation 1 is normalized by area by multiplying by the apparent geometric area, it becomes Equation 2:

$$ZA = \sqrt{\rho/(K/A)(j\omega)^{\alpha}} \coth(l\sqrt{rK(j\omega)^{\alpha}}) \qquad \text{(Equation 2)}$$

where ZA is the normalized impedance in $\Omega cm^2$, $\rho$ is resistivity in the pores ($\Omega cm$), and K/A is a constant analogous to capacitance per unit area ($Fcm^{-2}$). By high frequency approximation, the real and imaginary branches at high frequencies are merged into a line with a slope of $-\alpha/2$, which corresponds to the behavior of Warburg impedance. In the low and intermediate frequency region, Equation 2 is approximated by Equation 3. According to Equation 3, a short plateau should appear at intermediate frequencies due to pore resistance $l/3$, whereas there should be real and imaginary branches in parallel with slope of $-\alpha$ and separation by $\log(\tan(\alpha/2))$ in the low frequency region.

$$ZA = \frac{l\rho}{3} + \frac{1}{(K/A)\omega^{\alpha}}\cos\left(\frac{\alpha\pi}{2}\right) - j\frac{1}{(K/A)\omega^{\alpha}}\sin\left(\frac{\alpha\pi}{2}\right) \qquad \text{(Equation 3)}$$

Choice of Frequency to Determine Double Layer Capacitance of Nanoporous Layer Electrode The K of Equation 3 is the capacitance dominated by double layer capacitance. Thus, the real and imaginary part of normalized impedance (ZA) is as below $$Z_{Re}A = \frac{l\rho}{3} + \frac{1}{(C_{dl}/A)\omega^{\alpha}}\cos\left(\frac{\alpha\pi}{2}\right) \qquad \text{(Equation 4)}$$

$$Z_{Im}A = \frac{1}{(C_{dl}/A)\omega^{\alpha}}\sin\left(\frac{\alpha\pi}{2}\right) \qquad \text{(Equation 5)}$$

Figure 12A:
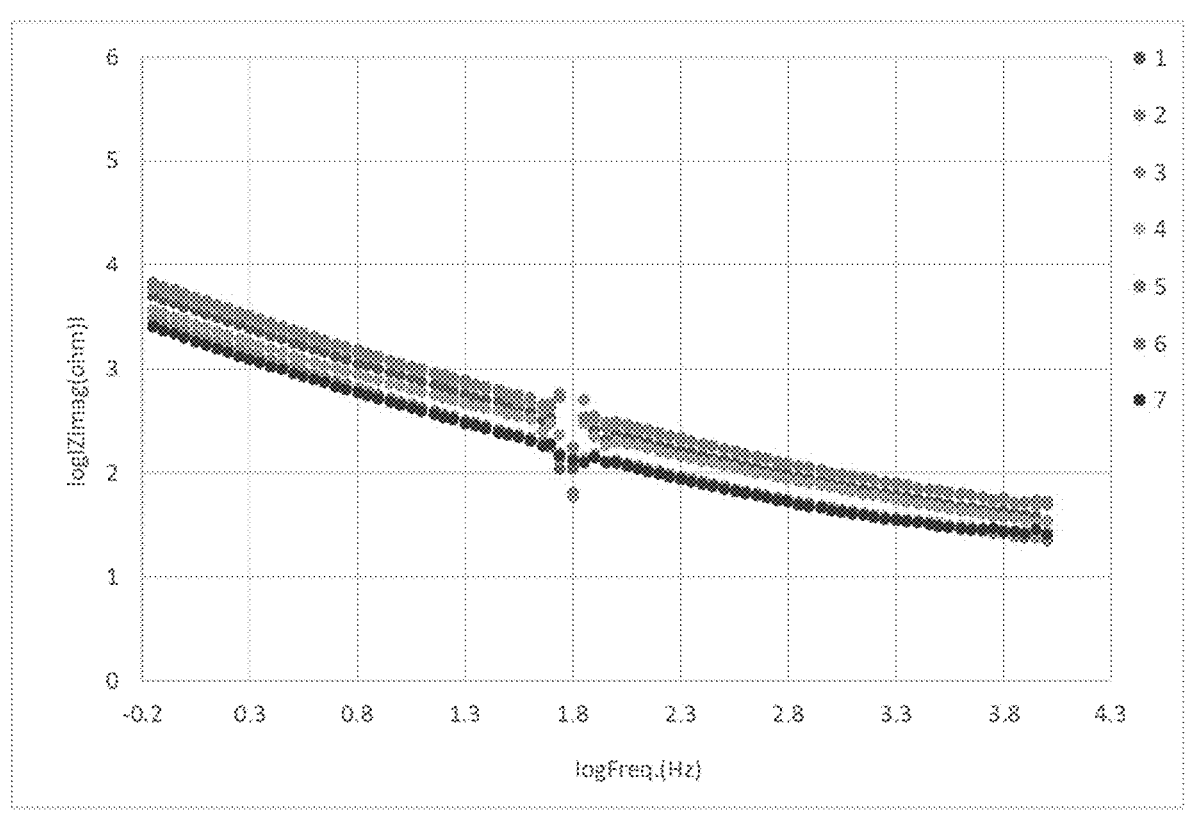
FIG. 12A is the impedance spectra (Zim vs frequency) plotted to find the frequency range of the nanoporous layer electrodes used in FIG. 10.

According to Equation 5, $\log Z_{Im}$ A and log w have a linear relationship with a slope of $-\alpha$. In other words, Equation 5 is valid in the frequency range where this linear relationship is established. Thus, the double layer capacitance Cdl can be determined by EIS data gathered in the frequency range where $\log Z_{Im}A$ or $\log Z_{Im}$ and log w have a linear relationship—if $\log Z_{Im}A$ and log $\omega$ have a linear relationship, and $\log Z_{Im}$ and log $\omega$ have a linear relationship. Example 4.1 and FIG. 12A illustrate the process of finding the frequency range. FIG. 12A is a plot of log |ZIm| v. log frequency. It shows that in the frequency range between 1 Hz and 1 kHz, log |ZIm| and log frequency have a linear relationship, and thus frequences in this range can be used. The figure shows that SRF does not exist in the frequency range between 1 Hz and 1 kHz. It is noted that once the frequency range for sensors with the same design should be the same. According to Equation 4, log $Z_{Re}A$ is linear to log w in low frequency range and separated from log $Z_{Im}A$ by log $(\tan(\alpha/2))$. However, in intermediate frequency range, $Z_{Re}A$ is dominated by pore resistance $$\frac{l\rho}{3}.$$

Therefore, the EIS data measured in this frequency region provides information about the mass transfer rate such as diffusion of glucose molecules inside the nanopores. What has been described above is the case when there is no outer membrane on the surface of the nanoporous layer electrode. If an additional outer film is coated, the resistance caused by the outer film is measured together, so it should be considered as the sum of the pore resistance and the outer membrane resistance.

Impedance, Effective Surface Area, and Glucose Sensitivity

From Equation 5, Cdl is inversely proportional to the imaginary capacitance at each frequency in low and intermediate frequency range:

$$C_{dl} = \frac{1}{(Z_{Im})\omega^{\alpha}}\sin\left(\frac{\alpha\pi}{2}\right) \qquad \text{(Equation 6)}$$

From Equation 4, Cdl is inversely proportional to the real capacitance at each frequency in low frequency range:

$$C_{dl} = \frac{1}{(Z_{Re})\omega^{\alpha}}\cos\left(\frac{\alpha\pi}{2}\right) \qquad \text{(Equation 7)}$$

In the meantime, the electrical double layer capacitance of the nanoporous layer is proportional to the effective surface area and the glucose sensitivity of the nanoporous layer sensor. Therefore, the effective surface area and the glucose sensitivity of the nanoporous layer sensor are inversely proportional to the imaginary capacitance at each frequency in low and intermediate frequency range; and are inversely proportional to the real capacitance at each frequency in low frequency range.

Linear Relationship of Hydrogen Adsorption Charge and Inverse of Imaginary Impedance (Capacitance)

As discussed herein, the charge of the hydrogen adsorption peak in a cyclic voltammetry is proportional to the effective surface area of the sensor, and the 1/|ZIm| value is also proportional to the effective surface area of the sensor. As such, the charge of the hydrogen adsorption peak (uC) and the 1/|ZIm| value should also be proportional to each other. However, in reality, the charge of the hydrogen adsorption peak (uC) and/or the 1/|ZIm| value obtained from experiments may have a linear relationship instead of a strictly proportional relationship because of deviations from theoretical values due to factors such as system setups, experimental conditions, and measurement errors, etc. The charge (Q) obtained from a cyclic voltammetry and the effective surface area (A) may have a linear relationship represented by Q=k1*A+c (c may or may not be 0). The 1/|ZIm| value obtained from an impedance spectrum and the effective surface area (A) may have a linear relationship represented by 1/|ZIm|=k2*A+d (d may or may not be 0). As such, the obtained hydrogen adsorption peak charge and/or 1/|ZIm| value at least have a linear relationship represented by Q=(k1/k2)(1/|Zimag|)+c−(k1/k2) d, where c−(k1/k2)d may or may not be 0, briefly as Equation 8. This linear relationship is illustrated in Example 5.2 and FIG. 11C.

$$Q = k(1/Z_{Im}) + l \qquad \text{(Equation 8)}$$

Obtaining Glucose Sensitivity from Impedance

Since the imaginary impedance of the nanoporous layer sensor system in the interstitial fluid measured in low and intermediate frequency is inversely proportional to the glucose sensitivity of the nanoporous layer sensor, 1/|ZIm| can be plotted against the glucose sensitivity of the sensor previously obtained from the current and concentration data to find the correlation between the 1/|ZIm| and the glucose sensitivity of the nanoporous layer sensor, which usually can be represented by a linear equation. This predetermined correlation, namely the linear fitting equation, can be used to obtain glucose sensitivity of the sensor according to the impedance data, specifically the imaginary impedance, measured by EIS at the selected frequency range, as illustrated in Examples 6 to 8 and FIGS. 10,14B, 15B, 16B, 17B, and 18B.

Summary of Process of Determining Glucose Sensitivity

Figure 5:
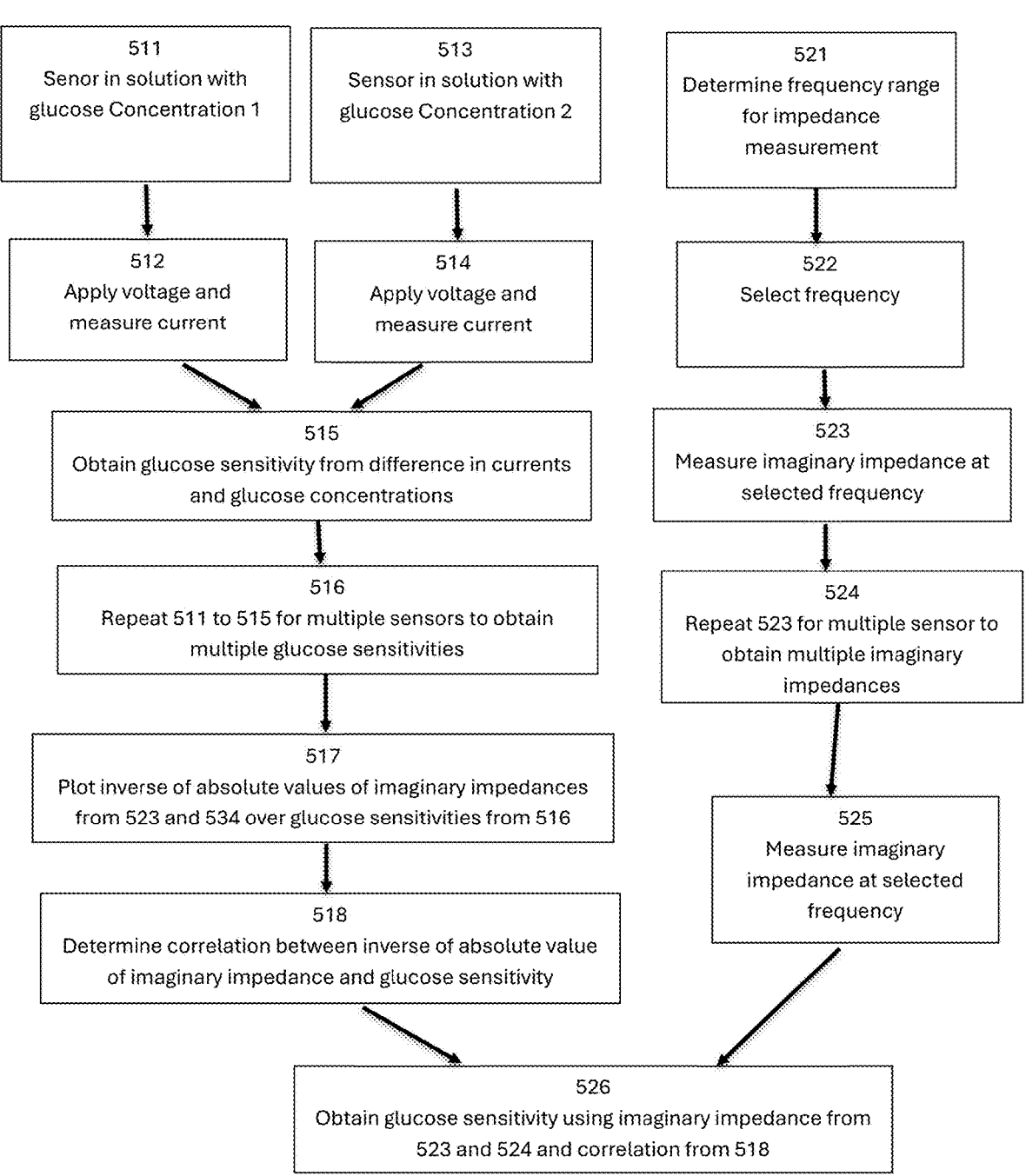
FIG. 5 is a flowchart illustrating the process of obtaining glucose sensitivity using impedance according to an embodiment.

As illustrated in the flowchart in FIG. 5, in step 511, a nanoporous layer sensor is submerged in a glucose solution with concentration 1. In step 512, a voltage is applied, and the generated current is measured. This process is repeated in another glucose solution with concentration 2 in steps 513 and 514. Then, in step 515, the glucose sensitivity of this sensor is obtained by dividing the difference in the measured currents by the difference in the glucose concentrations. In step 516, steps 511 to 515 are repeated for multiple sensors. In the meantime, in step 521, a frequency range is first determined for impedance measurement, and in step 522, a frequency is selected. In step 523, the imaginary impedance is measured at the selected frequency. In step 524, step 523 is repeated for multiple sensors. In step 517, the inverse of absolute values of imaginary impedances from step 524 are plotted over glucose sensitivities from step 516, and the correlation is determined. In step 523, the imaginary impedance of a sensor is measured. In step 524, the glucose sensitivity of the sensor is obtained using the imaginary impedance obtained in step 523 and the correlation obtained in step 518.

Measurement of Electronic Signal

The measurement of electronic signal (e.g., current, impedance, etc) in the methods provided herein can be repeated continuously or intermittently. In some embodiments, the measurement can be taken without interruption over a period of time. This means the data is being collected in real-time or at very short, consistent intervals. In some other embodiments, the measurement can be taken at specific intervals or only when needed.

Factory Batch Calibration of Nanoporous Layer Sensors

When each batch of nanoporous layer sensors is manufactured, samples sensors with different amounts of nanoporous layers are prepared using the material used in the batch. Alternatively, samples sensors can be randomly selected from each batch. The correlation between the inverse of the absolute imaginary impedance values and the glucose sensitivity of the sample sensors is determined as described herein. This correlation can be found for each of multiple batches or all batches. The manufactured sensors can carry the batch information, which can be linked to a manufacturing database that includes the information of the predetermined correlation of the batches. For sensors with the same design, if the deviation in the manufacturing process is small enough, meaning if the manufacturing process is consistent enough, this correlation may not need to be determined for all batches. The predetermined correlation can then be used for calibration of a sensor after it has been used for a certain period of time. Further, for sensors with the same design, the frequency range for impedance measurement should be the same. Even if manufacturing of nanoparticles does not affect the frequency range, it can affect the impedance of the nanoporous layer, but once the manufacturing process is consistent and repeatable, the frequency can stay the same and does not need to be changed. The impedance of the sensor can be obtained at appropriate time intervals, and the glucose sensitivity can be obtained using the predetermined correlation and the impedance, as illustrated in Examples 6 to 8 and FIGS. 10 and 14A to 18B.

Contamination, Cleaning, and Regeneration of Sensor

Deterioration of Glucose Sensitivity

When the nanoporous layer glucose sensor is implanted in a patient body and immersed in the interstitial fluid, some biological molecules other than glucose in the interstitial fluid can travel with glucose molecules through the intercluster spaces 127 to reach interparticular nanopores 123 and nanoparticles 125. These biological molecules may be contact or accumulate on at least part of surfaces of the metal nanoparticles that are accessible and thus cover the at least part of surfaces of the metal nanoparticles that would otherwise be available for glucose oxidation, rendering the covered surfaces incapable of interacting with glucose molecules for the oxidation reaction. As such, the effective surface area of the nanoparticles may decrease over time, causing the CGM sensor's glucose sensitivity to deteriorate. This decrease in surfaces of nanoparticles available for glucose oxidation results in diminished glucose sensitivity of the CGM sensing using the nanoporous layer sensor.

Electrochemical Cleaning of Nanoparticle Surfaces

The reduction of sensitivity may be recovered at least in part by removal of such contaminants from surfaces of the metal nanoparticles. Cleaning of contaminants may be done by application of a cleaning voltage input to the nanoporous layer. For example, when a positive potential is applied to the working electrode, an oxide layer may be formed on at least part of surfaces of the nanoparticles, and any organic material contacting or accumulated on these surfaces may be simultaneously stripped off of these surfaces. Following formation of the oxide and removal of the contaminants, a reducing potential can be applied to the working electrode, and the oxide layer may be cathodically dissolved by the reducing potential. This serves to clean or refresh the nanoporous layer and regenerate the clean, oxide-free surfaces of the metal nanoparticles.

Cleaning Voltage Input

The voltage input required for electrochemical cleaning of the nanoporous electrode can vary depending on the specific material and the contaminants being removed. For example, a pulse voltage may be applied to remove the contaminants to increase the effective surface area of the metal nanoparticles. FIGS. 29A, 30A, 31B, 31D, 32B, 32D, and 32F show the cyclic or pulse voltage input applied in Examples 9.4, 9.6, 9.7, 10.4, 10.5, and 10.6. As demonstrated in these examples, these voltage inputs were shown to have good cleaning efficiency. As illustrated in these figures, such a voltage input includes a series of repeating square wave voltage pulses. Each pulsing phase includes voltage steps alternating between a positive peak voltage and a negative peak voltage, with each peak voltage held for a pulse duration and the whole voltage input lasting for a total duration. The absolute value of the peak voltage is referred to as the amplitude or the peak amplitude. The peak-to-peak amplitude refers to the voltage range between the top peak to the bottom peak. The cleaning voltage input usually includes positive peak voltages and negative peak voltages as shown in these examples, and the peak-to-peak amplitude of the cleaning voltage input usually means the voltage range between the positive and negative peak voltages, namely, from the negative peak voltage to the positive peak voltage or from the positive peak voltage to the negative peak voltage. The cleaning voltage input may have different waveforms, and a cleaning voltage input with any waveform may be defined by parameters including the peak amplitude, peak-to-peak amplitude, pulse duration, and total duration.

Peak Amplitude of Cleaning Voltage Input

The cleaning voltage input, such as the pulse voltage inputs shown in FIGS. 29A, 30A, 31B, 31D, 32B, 32D, and 32F, may have a peak amplitude of at or about 100, 150, 200, 250, 300, 350, 400, 450, 500, 550, 600, 650, 700, 750, 800, 850, 900, 950, 990, 1000, 1010, 1020, 1030, 1040, 1050, 1060, 1070, 1080, 1090, 1100, 1200, 1300, 1400, 1500, 1600, 1700, 1800, 1900, 2000 mV, etc. In embodiments, the peak amplitude of the cleaning voltage input may be within a range formed by selecting any two numbers in the immediately preceding sentence, such as from about 250 to about 300 mV, or from about 200 to about 700 mV, etc. Preferably, the cleaning voltage input has a peak amplitude that is at the hydrogen reduction adsorption potential as measured in the CV of the nanoporous layer electrode.

Peak-to-Peak Amplitude of Cleaning Voltage Input

The cleaning voltage input may have a peak-to-peak amplitude with the positive peak voltages at or about 100, 150, 200, 250, 300, 350, 400, 450, 500, 550, 600, 650, 700, 750, 800, 850, 900, 950, 990, 1000, 1010, 1020, 1030, 1040, 1050, 1060, 1070, 1080, 1090, 1100, 1200, 1300, 1400, 1500, 1600, 1700, 1800, 1900, 2000 mV, etc. and with the negative peak voltages at or about −100, −150, −200, −250, −300, −350, −400, −450, −500, −550, −600, −650, −700, −750, −800, −850, −900, −950, −990, −1000, −1010, −1020, −1030, −1040, −1050, −1060, −1070, −1080, −1090, −1100, −1200, −1300, −1400, −1500, −1600, −1700, −1800, −1900, −2000 mV, etc. In embodiments, the peak-to-peak amplitude of the cleaning voltage input may be from any negative peak voltage in the immediately preceding sentence to any positive peak voltage in the immediately preceding sentence, such as from about −1000 mV to about 1000 mV, from about −250 mV to about 700 mV, from about −300 mV to about 700 mV, and from about −250 mV to about 250 mV, from about −300 mV to about 300 mV, from about −700 mV to about 250 mV, or from about −700 mV to about 300 mV, from about −500 mV to about 500 mV, from about −250 mV to about 500 mV, from −500 mV to about 250 mV, from about −2000 mV to about 500 mV, from about −500 mV to about 1500 mV, from about −1500 mV to about 1500 mV, etc.

Variations of Amplitudes of Cleaning Voltage Input

Figure 7A:
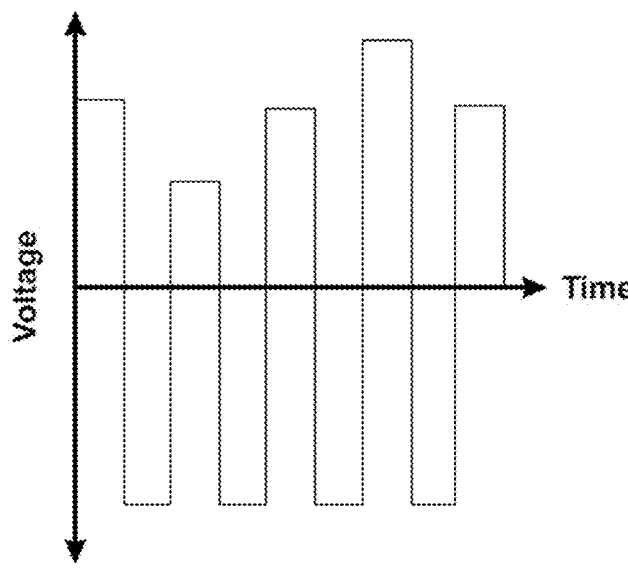
FIGS. 7A-7O illustrates example waveforms of the cleaning voltage input according to some embodiments.
Figure 7B:
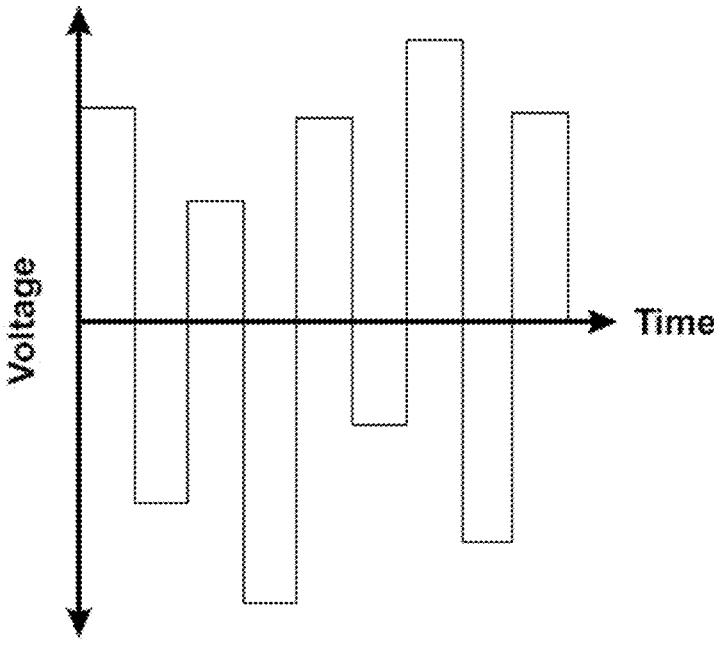
Figure 7C:
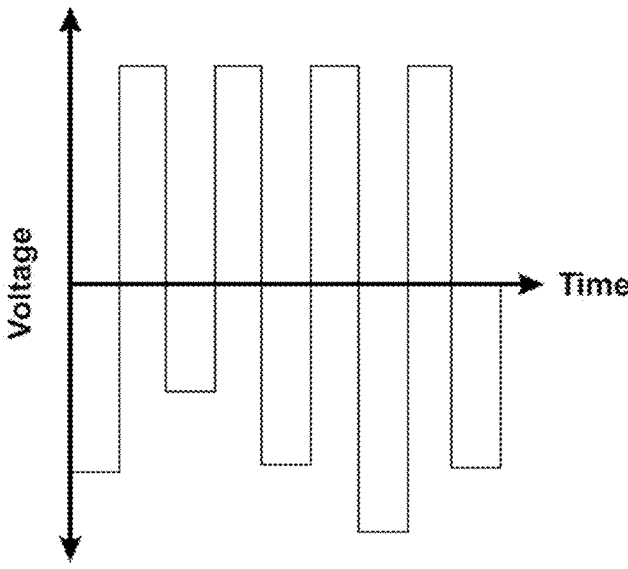

In the examples shown in FIGS. 29A, 30A, 31B, 31D, 32B, 32D, and 32F, the positive peak voltages are all the same in each pulsing phase; and similarly, the negative peak voltages are also all the same in each pulsing phase. In some other embodiments, different pulsing phases may have the same or different positive peak voltages and may have the same or different negative peak voltages, as illustrated in FIGS. 7A, 7B, and 7C. The amplitude in the positive direction may be the same as or different from the amplitude in the negative direction. For example, in FIG. 29, all pulsing phases have the same positive peak voltage 700 mV and also have the same negative peak voltage-250 mV; and the amplitude in the positive direction is 700 mV, and the amplitude in the negative direction is 250 mV.

Determining Peak Voltages of Cleaning Voltage Input

As the overvoltage—difference between the measurement voltage and the amplitude of the cleaning voltage input—increases, the sensitivity of the nanoporous layer is recovered more effectively. The greater the amplitude of the cleaning voltage input, the more effectively the nanoporous layer is cleaned, refreshed, or regenerated. However, excessive overvoltage can cause the irreversible reactions of any polymer material in or on the nanoporous layer surface if the nanoporous layer includes, for example, one or more polymer binder or ion-blocking materials, and can also cause gas evolution (oxygen). These reactions cause irreversible changes in the performance of the nanoporous layer. Thus, the positive peak voltage of the cleaning voltage input is usually chosen to be greater than the voltage that causes oxidation of surfaces of the metal nanoparticles but smaller than the voltage that causes any irreversible reaction. Likewise, the negative peak voltage of the cleaning voltage input is usually chosen to be more negative than the voltage that causes reduction of surfaces of the metal nanoparticles and less negative than the voltage that causes any irreversible reaction. The peak voltages of the cleaning voltage input may be determined experimentally.

Pulse Duration of Cleaning Voltage Input

Figure 7D:
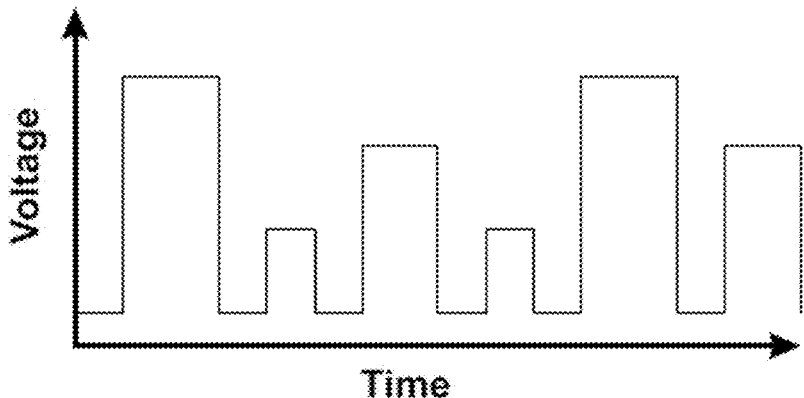

Each pulse phase or each step of the cleaning voltage input may last a pulse duration at or about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 seconds, etc. In embodiments, the total duration of the cleaning voltage input may be within a range formed by selecting any two numbers in the immediately preceding sentence, such as from about 0.1 to about 0.5, from about 1 to about 5, from about 1 to about 10, from about 5 to about 10, from about 5 to about 30, from about 10 to about 30, from about 30 to about 40, from about 30 to about 50, from about 30 to about 60, from about 60 to about 90, from about 60 to about 70, from about 70 to about 80, or from about 70 to about 90 seconds, etc. For instance, the examples shown in FIGS. 29A, 30A, 31B, 31D, 32B, 32D, and 32F each has a pulse duration of 30 seconds, and all pulse phases in each example have the same pulse duration. In other embodiments, the pulse phases may have varying pulse durations, as illustrated in FIG. 7D. It is understood that FIG. 7D is merely an illustrative example and is non-limiting. The pulse durations may be the same or different and may not be in any particular orders.

Total Duration of Cleaning Voltage Input

The cleaning voltage input may be applied for a total duration at or about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 minutes, etc. In embodiments, the total duration of the cleaning voltage input may be within a range formed by selecting any two numbers in the immediately preceding sentence, such as from about 0.1 to about 0.5, from about 1 to about 5, from about 1 to about 10, from about 5 to about 10, from about 5 to about 30, from about 10 to about 30, from about 30 to about 40, from about 30 to about 50, from about 30 to about 60, from about 60 to about 90, from about 60 to about 70, from about 70 to about 80, or from about 70 to about 90 minutes, etc. If needed, the cleaning voltage input can be applied for more than 90 minutes. For instance, the examples shown in FIGS. 29A, 30A, 31B, 31D, 32B, 32D, and 32F each has a duration of 30 minutes, which means the cleaning voltage input in these examples is applied for a total of 30 minutes.

How Often and how Long of Cleaning

"Sensor usage period" is the time that the sensor is inserted in a user's body and operated with measuring voltage applied. The longer the sensor usage period, the longer the cleaning. If the sensor is used for a long duration, the cleaning voltage input may need to be applied for a long duration and/or more often. For example, after the sensor has been operated for 10 days, it may be necessary to apply the cleaning voltage input for 30 minutes to recover the sensor signal. If the sensor has been operated for a longer time, such as for one or more months, it may be necessary to apply the cleaning voltage input longer, such as for a few hours. If the sensor has been operated for several hours, a few minutes of cleaning voltage may be enough to recover the sensor signal. As the sensor is operated for a longer time, the contamination of the nanoporous layer surface takes place extensively, and thus cleaning voltage is required to be applied for a longer time. On the other hand, the sensor may be cleaned every day, every few days, every week, or every month. If the sensor is cleaned often, then the cleaning voltage input may be applied for a short time each time the sensor is cleaned. For example, if the sensor is cleaned once every few hours, then each time the sensor is cleaned, the cleaning voltage input may only need to be applied for a few seconds. If the sensor is cleaned once every day, then each time the sensor is cleaned, the cleaning voltage input may need to be applied for a few minutes. If the sensor is cleaned once every week, then each time the sensor is cleaned, the cleaning voltage input may need to be applied for 10, 20, or 30 minutes. If the sensor is cleaned once every month, then each time the sensor is cleaned, the cleaning voltage input may need to be applied for 30, 40, 50 minutes, 1, 1.5, or 2 hours.

Other Possible Waveforms of Cleaning Voltage Input

Figure 7E:
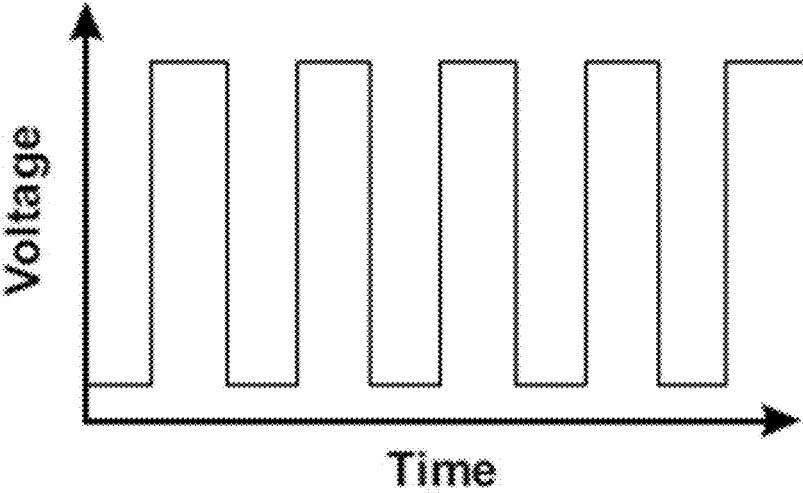
Figure 7F:
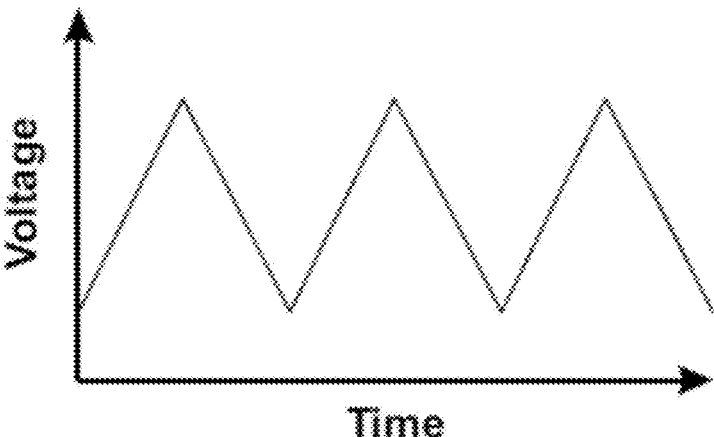
Figure 7G:
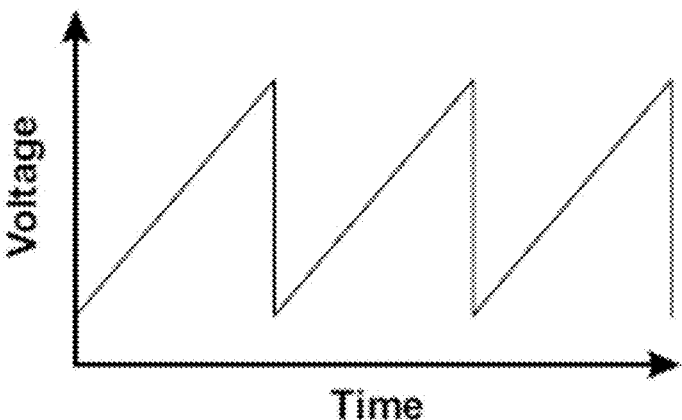
Figure 7H:
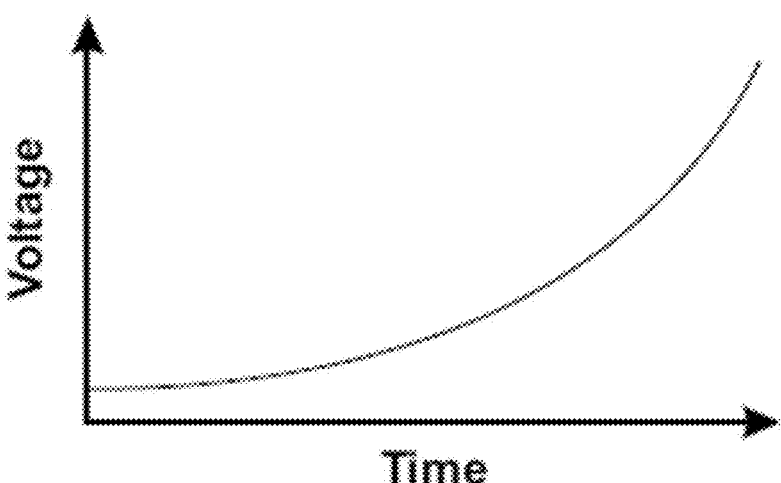
Figure 7I:
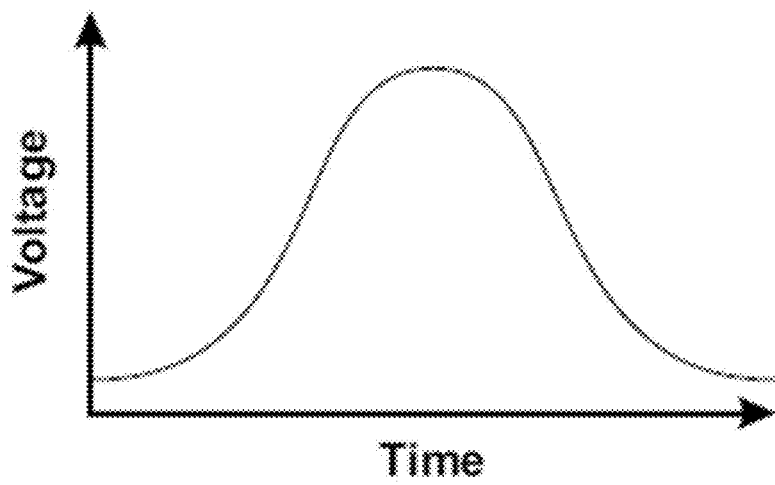
Figure 7J:
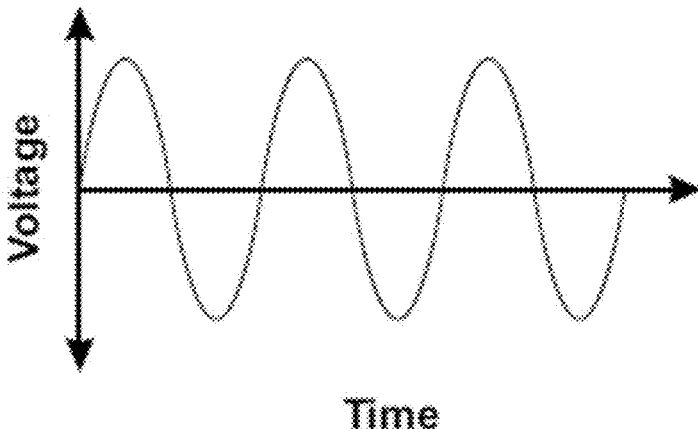
Figure 7K:
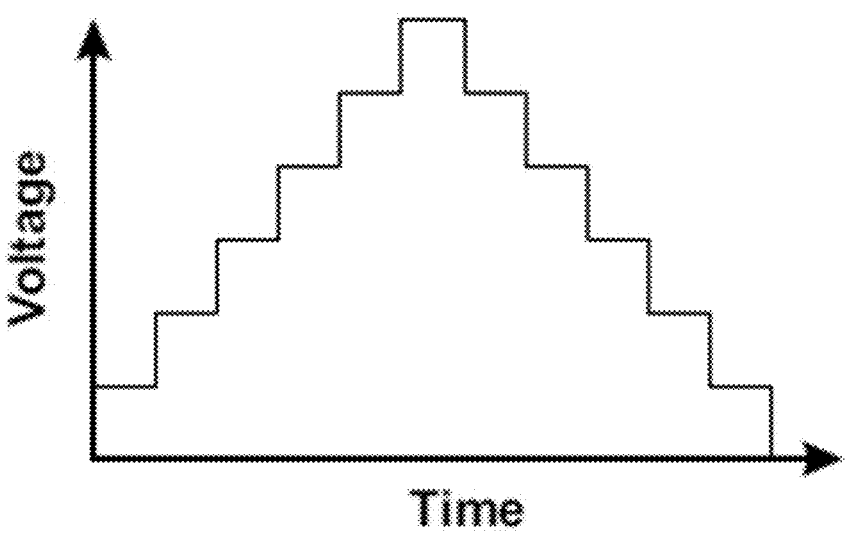
Figure 7L:
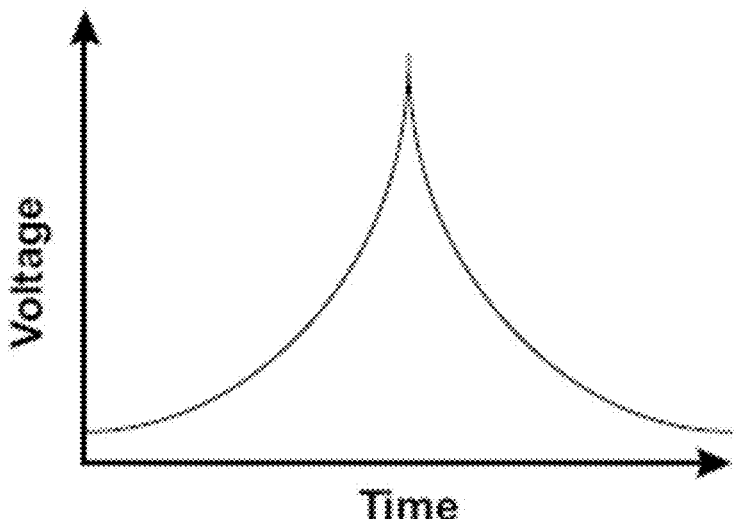
Figure 7M:
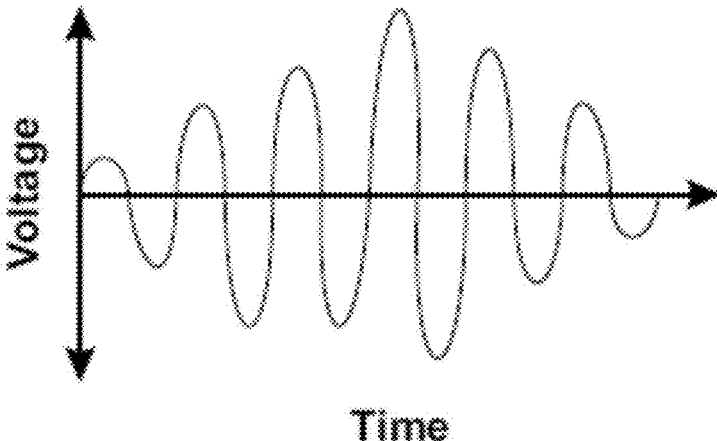
Figure 7N:
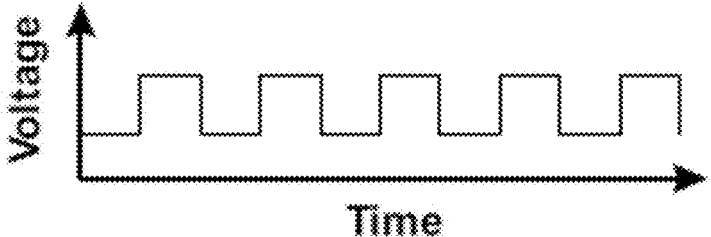
Figure 7O:
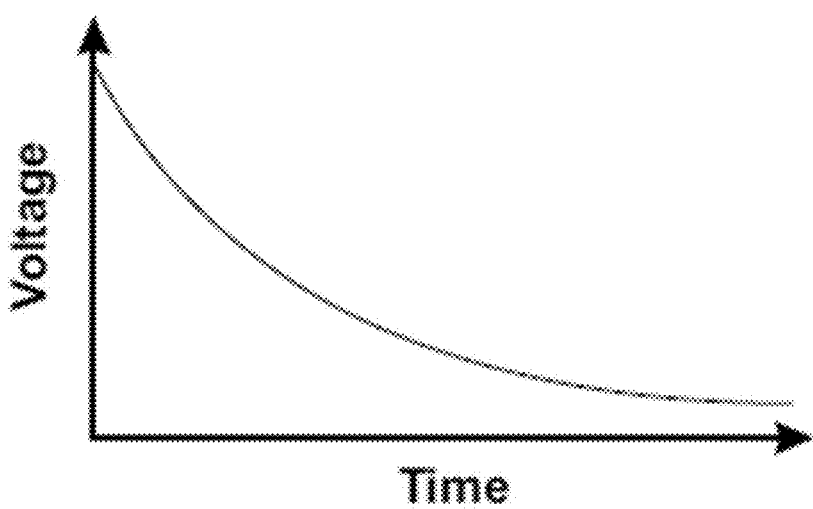

The cleaning voltage input may have one or more waveforms The possible waveforms include, but are not limited to, rectangular, triangular, sawtooth, exponential, Gaussian, sinusoidal, step, double exponential, bipolar, sigmoidal, or square, etc. As illustrated in FIG. 7E, a rectangular pulse is a pulse with a sharp rise and fall time and a constant voltage in between and is defined by its amplitude, duration (pulse width), and repetition rate. The waveforms shown in FIGS. 29A, 30A, 31B, 31D, 32B, 32D, and 32F are examples of a rectangular pulse waveform. As illustrated in FIG. 7F, A triangular pulse voltage increases linearly to a peak and then decreases linearly. As illustrated in FIG. 7G, a sawtooth pulse voltage increases (or decreases) linearly and then drops (or rises) sharply. As illustrated in FIGS. 7H and 7O, an exponential pulse voltage rises or falls exponentially with time. As illustrated in FIG. 7I, a Gaussian pulse is shaped like a Gaussian curve, with smooth transitions and no sharp edges. As illustrated in FIG. 7L, a double exponential pulse has an exponential rise time and an exponential decay. As illustrated in FIG. 7M, a sinusoidal pulse has a shape of a segment of a sinusoidal wave. As illustrated in FIG. 7N, a square wave is a periodic waveform with alternating constant high and low levels. A step pulse has a sudden rise or fall in voltage without a return to the baseline level within the observed period. A bipolar pulse has alternating positive and negative polarities. The waveforms shown in FIGS. 29A, 30A, 31B, 31D, 32B, 32D, and 32F may be considered examples of a step pulse waveform or a bipolar pulse waveform. The cleaning voltage waveform may also be pulse function with repeating positive and negative overvoltage. The pulse voltage may have one or more waveforms that are not discussed above.

Determining Glucose Sensitivity

After the cleaning voltage input is applied to the nanoporous layer sensor as provided herein, the biomaterials or contaminants covering surfaces of the nanoparticles in the nanoporous layer are stripped off or removed therefrom, and thus the nanoporous layer is cleaned, refreshed, and/or renewed. The sensor's glucose sensitivity after the cleaning is unknown and can be obtained as described herein. The cleaning may be repeated multiple times. In some embodiments, the sensor's sensitivity may be determined every time after the cleaning is performed. The measurement of the electrical signal may be repeated continuously or intermittently as described herein. In embodiments, every time the cleaning is performed, the sensor's glucose sensitivity may be determined between the cleaning step and the measuring step.

Benefits of Cleaning Followed by Sensitivity Measurement

The cleaning, refreshing and/or renewal of surfaces of the metal nanoparticles in the nanoporous layer can be triggered automatically at preset intervals or activated on demand by the user, which continuously removes biofouling and surface contaminants to preserve sensor integrity and extend its operational life. Immediately following each cleaning cycle, the system performs a sensitivity measurement as provided herein, ensuring consistently accurate glucose readings over time. These combined features enable a permanent or semi-permanent CGM device or system, overcoming the limited lifespans and drift issues of enzymatic sensors caused by factors such as enzyme degradation and leaching. No other CGM technology today can both regenerate its sensing surface and verify its own sensitivity in real time, making this platform a true breakthrough in long-term, reliable glucose monitoring. While the integrated electrochemical cleaning and sensitivity measurement theoretically pave the way for a truly permanent implantable CGM, real-world factors inevitably introduce imperfections. Material fatigue, microfractures in the electrodes, and unpredictable biological responses such as encapsulation or inflammatory reactions can all compromise long-term functionality. As a result, instead of lasting indefinitely, the device may be best viewed as semi-permanent: it can operate reliably for extended periods far beyond conventional enzymatic sensors, but will eventually require replacement or refurbishment when cumulative defects impair its performance.

Implantable Glucose Sensor

Implantable Glucose Sensor Device

An implantable glucose sensor device provided herein includes a glucose oxidation electrode comprising a nanoporous layer which comprises metal nanoparticles as provided herein. The device also includes a counter electrode and optionally a reference electrode. The device further includes a circuit configured to apply a DC voltage between the glucose oxidation electrode and the counter electrode or the reference electrode. The circuit is further configured to apply an AC voltage between the glucose oxidation electrode and the counter electrode or the reference electrode. The circuit is configured to create the cleaning voltage input as provided herein. The device can apply the cleaning voltage to the glucose oxidation electrode and the counter electrode or the reference electrode to clean, refresh, renew, and/or regenerate surfaces of the metal nanoparticles of the glucose oxidation electrode as provided herein. The device also includes circuits to enable determination of the glucose sensitivity of the glucose oxidation electrode and measurement of the glucose level of the user in whose body the device is implanted. The circuits can also measure DC currents indicative of glucose oxidation in the glucose oxidation electrode when applying the DC voltage between the glucose oxidation electrode and the counter electrode or the reference electrode. The circuits further can measure an impedance indicative of solid-liquid interface information of the metal nanoparticles in the nanoporous layer.

Body or Housing

Figure 8A:
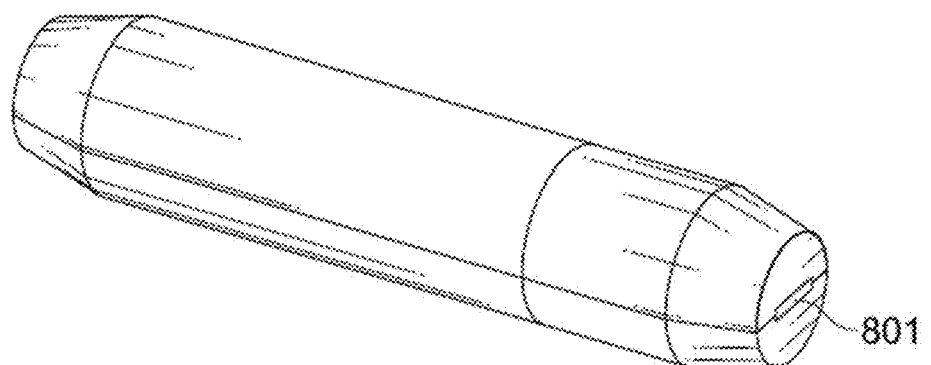
FIGS. 8A to 8B are drawings of an example embodiment of the implantable device.

According to embodiments, the implantable glucose sensor device provided is in the form of a sealed case with a passage for liquids to enter and exit herein. It includes a body or housing that houses the components thereof, such as the glucose oxidation electrode comprising the nanoporous layer and the electrical circuits, as well as a power source, although not limited thereto. The body or housing is usually made from biocompatible materials like titanium, ceramic, or polymer composites. The sealed encapsulation protects sensitive electronics from bodily fluids while allowing wireless energy and signals to pass through effectively. FIG. 8A shows an example implantable device provided herein. The body or housing of this example device has the shape of a tube, and the two ends of the tube may have a smaller diameter than the diameter of the middle portion of the tube. The body or housing of the implantable device may have any shape suitable for implantation. The body or housing can be in any size that is suitable for implantation in the user's body. In some embodiments, the body of the device has a length in a range of from about 10 to about 20 mm, such as 18.5 mm, and the cross-section of the body has a diameter in a range from about 2 to about 5 mm, such as 4 mm. The body has an opening that allows or guides the user's interstitial fluid to enter the device. The shape and location of the opening may depend on the specific design. The example device in FIG. 8A has the opening 801 on one end, and the opening is in the form of a fattened groove or slit, which allows controlled entrance of the interstitial fluid containing glucose into the device when the device is implanted in the user's body.

Nanoporous Layer Glucose Sensor

Figure 8B:
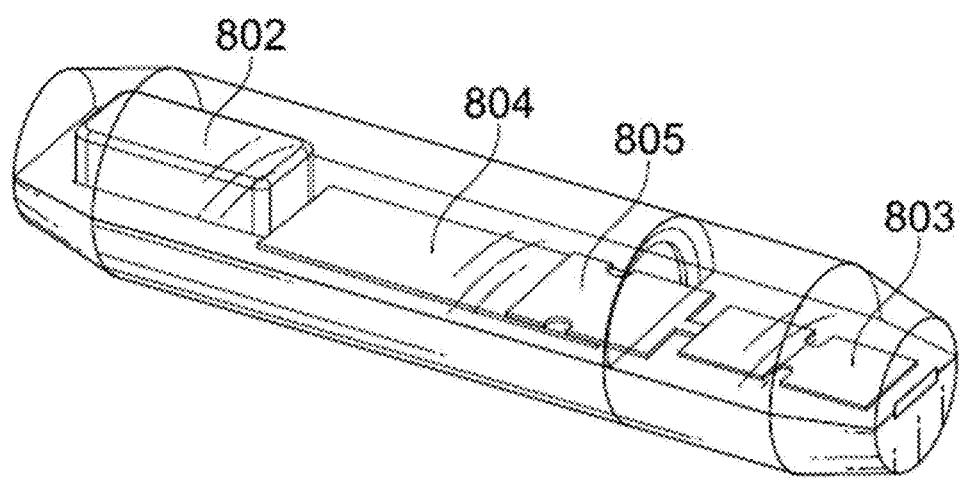
Figure 9:
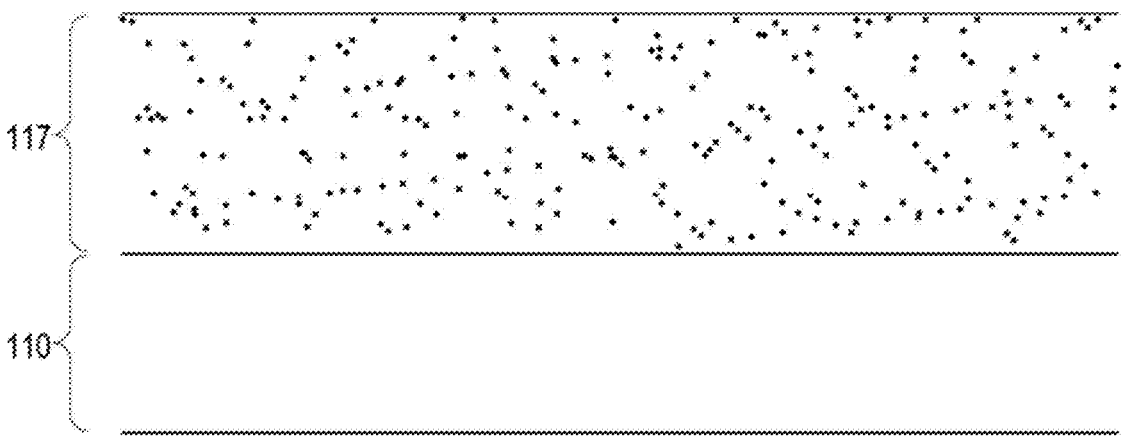
FIG. 9 illustrates layers of a working electrode including a nanoporous layer and a substrate according to an embodiment.

FIG. 8B shows the internal structure of the example device in FIG. 8A. As shown in FIG. 8A, a membrane 803 may cover the inside wall of the opening, may be located along the opening, or may be located between the opening 801 for the interstitial fluid and the sensor 805. The membrane 803 may be, for example, an ion blocking layer, a maltose blocking layer, etc., and filter out some biological or other undesirable materials or block undesirable ions in the interstitial fluid when it passes through the membrane inside of the opening. Near the end of or behind the membrane 803 is the nanoporous layer glucose sensor 805 comprising the nanoporous layer electrode and a counter electrode and optionally a reference electrode. The sensor 805 is located at the front end of the device, right behind the membrane 803 and connected with the printed circuit board (PCB) 805. The nanoporous layer electrode may have a cross-section layer structure as illustrated in FIG. 2 or 9. When the device is implanted in the user's body, the interstitial fluid containing glucose enters the device from the opening 801, passes through the membrane 803, and reaches the sensor 805, and thus the nanoporous layer electrode and the counter electrode or reference electrode on the sensor are both fully submerged in the fluid containing glucose. When a voltage is applied to the opposing electrodes, an electrical signal is generated and measured as provided herein, and then the glucose sensitivity and the glucose level are obtained as provided herein.

Power Source

The device includes a power source. In the example device of FIG. 8B, the power source is a battery located near the end opposite where the opening is located. The battery provides power to the circuits for the circuits to generate DC and/or non-DC voltages to the sensor. The battery may be rechargeable wirelessly.

Printed Circuit Board (PCB)

The device includes a miniaturized printed circuit board (PCB) comprising circuits built thereon that enable the operation of the device and serving as the foundation for all electrical components of the device. In the example device shown in FIG. 8B, the PCB 804 is located between the battery 802 and the sensor 805 and electrically connected thereto. The PCB is usually made from biocompatible materials and may be designed in a multi-layer configuration to accommodate complex circuitry while maintaining a small footprint. Its layout is usually tightly packed to reduce volume and power consumption.

Circuits

The electrical circuits include a control module, an EIS module, a wireless communication module, and a wireless charging module although not limited thereto. Each module includes electrical circuits with or without at least one chip. At least one electrical circuit may generate a DC voltage and/or a non-DC voltage waveform. The generated voltage, whether a DC or a non-DC voltage, may be applied to the two opposing electrodes of the sensor.

Control Module

The circuits include a control module that manages and regulates the operation of the device and its components by processing inputs, executing programmed logic, and/or delivering appropriate outputs. The control module is a compact, programmable system that integrates both sophisticated functionality and a miniaturized, durable structure to support continuous glucose monitoring within the user's body using the device. It serves as the central processor of the device, responsible for managing sensor data, power, communication, and system diagnostics—all while operating reliably in the challenging conditions of long-term implantation. Structurally, the control module is built on a multi-layer printed circuit board (PCB), designed for high-density integration within a small form factor. At its core is a low-power microcontroller or application-specific integrated circuit (ASIC) that has been pre-programmed to run glucose monitoring algorithms, manage sensor inputs, and control system behavior in real time. This processor is surrounded by supporting circuitry, including the Analog Front-End (AFE).

AFE Circuit

The AFE processes analog signals from the sensor before converting them into digital signals for further analysis and amplifies, filters, and digitizes weak signals from the glucose sensor for accurate interpretation. The AFE may include components such as signal generators (AC waveform sources), programmable amplifiers, filters, and analog-to-digital converters (ADC) or digital-to-analog converters (DAC).

Electrical Impedance Spectroscopy Module

The circuits also include an Electrical Impedance Spectroscopy (EIS) module to measure the impedance of the glucose sensor submerged in the interstitial fluid inside the device as described herein. The EIS module may be integrated in the control module circuitry or a separate circuit.

At the core of the EIS module is a signal generation unit that produces an alternating current (AC) signal, for example, in the range of 1 Hz to 1 MHz. This signal is injected applied to the sensor electrodes, and the resulting voltage drop is measured to determine the impedance. The current injection is often achieved using a voltage-to-current converter, which ensures a stable and controlled current flow, minimizing noise and interference. The voltage response is captured by a differential amplifier, which offers low offset voltage and high common-mode rejection ratio, making it suitable for low-power, implantable applications. This amplified signal is then digitized by an Analog-to-Digital Converter (ADC), which provides high-resolution measurements essential for accurate impedance analysis. Data processing is typically handled by a microcontroller, which performs calculations to extract the real and imaginary components of impedance. This microcontroller may be the same as or different from the microcontroller of the control module. As shown in the example system diagram shown in FIG. 8C of the example device in FIGS. 8A and 8B, the EIS module is an AFE circuit that includes hardware and circuitry for generating signals, measuring responses, and processing data to analyze the electrochemical properties of the sensor. The AFE generates precise voltage or current signals, applies them to the sensor and measures the resulting signals to extract the impedance data, which is then used for determining the glucose sensitivity of the glucose sensor as provided herein.

Wireless Communication Module

Figure 8C:
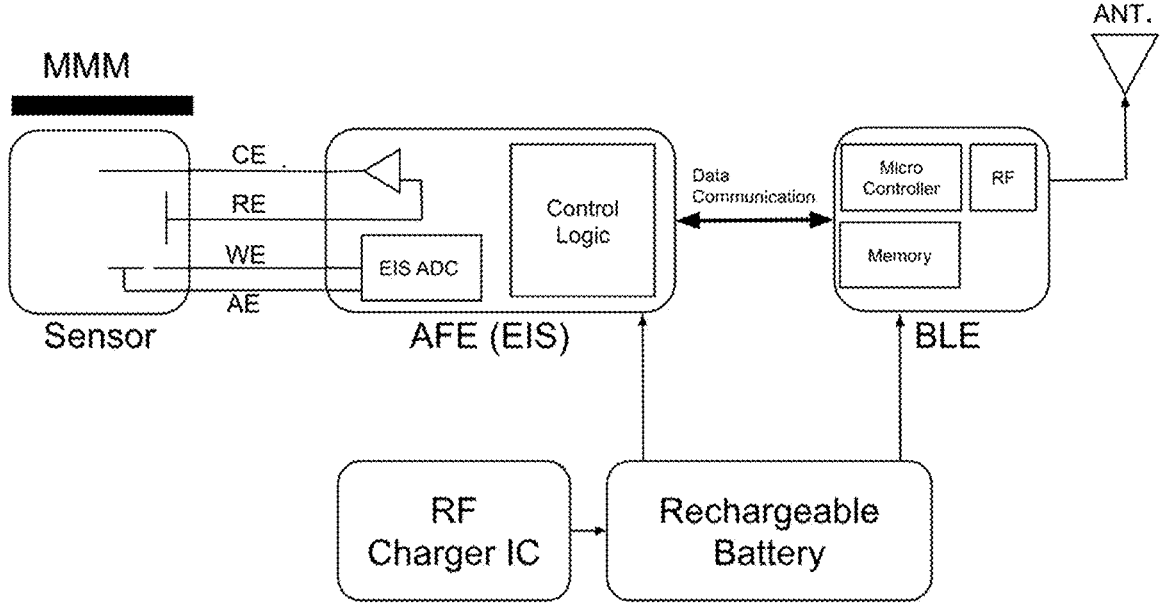
FIG. 8C shows the system diagram of the example implantable device shown in FIGS. 8A to 8B.

The circuits also include a wireless communication module to enable seamless data sharing, which sometimes may be stacked or embedded into the same PCB layer(s) as the control module and/or the EIS module. The wireless communication module sends and receives signals using protocols like Bluetooth Low Energy (BLE), proprietary Radio Frequency (RF), Wi-Fi, and/or cellular networks. It securely transmits real-time glucose data to external receivers, such as smartphones or insulin pumps, without physical connections, while usually maintaining low power usage to preserve battery life. The module typically includes a transmitter, receiver, and processing unit to manage data flow, ensure signal integrity and optimize connectivity. By enabling real-time wireless data exchange, it enhances flexibility, reduces wiring complexity, and supports remote operation. The implantable device provided herein may include one or more wireless communication modules. As shown in FIG. 8C, the example device uses BLE, which is part of the Bluetooth standard (introduced in Bluetooth 5.2). BLE operates in the 2.4 GHz ISM (Industrial, Scientific, and Medical) band and uses frequency-hopping spread spectrum (FHSS) to minimize interference. It uses predefined profiles to ensure interoperability between devices and is designed for applications where battery life is critical. BLE typically operates within a range of about 10 meters. It is optimized for small, intermittent data exchanges rather than continuous high-bandwidth streaming. This makes it ideal for receiving and sending data from and to the AFE and the sensor. As shown in FIG. 8C, the wireless communication module in the example device also includes an antenna, which is a transducer that converts electrical signals into electromagnetic waves for transmission and vice versa. It serves as the interface between the wireless communication module and the air, enabling the transmission and reception of radio waves. The wireless communication module may include an external antenna and/or an integrated antenna, depending on factors like desired communication range, device size, and environmental conditions. The example device as shown in FIG. 8C also includes a RF module. RF refers to the range of electromagnetic wave frequencies from approximately 3 kilohertz (kHz) to 300 gigahertz (GHz). An RF module typically comprises a transmitter and/or receiver, and it may include an antenna either integrated within the module or as an external component. The antenna serves as the interface between the RF module and the air, converting electrical signals into electromagnetic waves for transmission and vice versa.

Wireless Charging Module

Supporting the operation of the implantable device and the functions of its components, such as the sensor, the control module, the EIS module, and the wireless communication module, is the power source such as the rechargeable battery powered by a wireless charging module, which enables power transfer without physical connectors by using electromagnetic induction or resonant coupling and thus eliminating the need for invasive charging mechanisms. The wireless charging module may be a standalone component or a separate circuit connected to the control module or integrated directly into the control module. The control module manages the charging process, regulating power flow and temperature to ensure safe and efficient energy transfer without damaging surrounding tissue. The wireless charging module may include a miniature receiving coil or antenna that allows the device to recharge inductively through the skin by receiving power inductively from an external transmitter. The control module manages this energy and distributes the received power to charge the rechargeable battery in the device. As shown in FIG. 8C, the wireless charging module in the example device includes a RF charger integrated circuit (IC), which facilitates wireless charging using RF energy of varying power levels and frequencies. The RF charger IC can collect energy from ambient RF sources (e.g., Wi-Fi, cellular signals) or dedicated RF transmitters. For example, in the charging process, an external RF transmitter generates RF signals, typically in the range of MHz to GHz, and sends them wirelessly through the air. The receiving coil or antenna in the RF charger IC captures the RF signals and converts it into a stable DC output using a rectifier to convert RF (AC) to DC and a voltage regulator to ensure the output is within the desired range. The DC power can then be used to charge the battery. The RF charger IC has a compact size and can be easily integrated into the implantable device.

Single Body Embodiments

In some embodiments, the implantable glucose sensor device is in a single body and may be implanted in its entirety in a user's body without any portion of the device outside the user's body. The device is entirely self-contained and fully internal once implanted. The device is constructed as one complete unit—a single, unified structure—rather than being made up of separate components that need to be connected externally or through the skin. When implanted, the entire device resides within the user's body, with no wires, ports, sensors, extensions, or any part protruding outside. The fully internal, single-body implant can reduce risk of infection (for example, since there are no openings in the skin), greater comfort for the user, and improved aesthetics. It may also allow for greater freedom of movement and reduce the need for ongoing maintenance or visible attachments. The compact, fully enclosed device, once implanted, becomes a seamless part of the body without any external elements, promoting better integration and usability.

Implementation of EIS Measurement in Implantable Glucose Sensor Device

The implantable device is pre-programmed, and the EIS measurement condition and interval can be automatically applied and/or adjusted. For example, in the example device illustrated in FIGS. 8A-8C, in the Potentiostat mode (DC Mode), the circuits apply a constant voltage to the sensor as instructed by the control module, and the electrochemical reaction of glucose occurs in the sensor at, on, and/or near the surface of the nanoporous layer electrode, and the current flows. This current value is changed to a digital value through the ADC and transmitted to the BLE chip through the internal control logic of the AFE (EIS). In the EIS mode (AC mode), the circuits apply an AC voltage at a set frequency (e.g., about 1 Hz to about 10,000 Hz) to the sensor, the change in the sensor output value is converted to a digital value (real and imaginary impedance data) in the sensor ADC and stored in a data buffer or memory queue where the first data entered is the first to be retrieved (FIFO). In the BLE chip, the values stored in the FIFO are read, and the phase and magnitude are calculated through programmed formulas. Overlapping AC modes can be used during DC mode operation. The BLE chip and AFE (EIS) chips are controlled through data communication (SPI, UART, GPIO, I2C, etc.).

Use of Implantable Glucose Sensor Device

The implantable device is designed for people with diabetes, offering real-time glucose tracking without the need for frequent finger sticks. The device may be implanted subcutaneously in the upper arm or another suitable location of the user's body by a healthcare provider where it may measure glucose levels in the interstitial fluid for a long period of time. Healthcare providers may follow a detailed, sterile procedure that could involve cleaning the insertion area, administering local anesthesia, making a small incision, creating a shallow pocket with the blunt dissector, and finally placing the device into position. Once the device is in place, a removable smart transmitter may be positioned externally over the device. This transmitter may power the device and continuously send glucose data via Bluetooth to a mobile app, which can display real-time readings, trends, and alerts. The transmitter may feature on-body vibration alerts to notify the user when glucose levels reach pre-set thresholds, and it may be powered by a rechargeable battery designed to last for a long time. Daily adhesive patches may be used to secure the transmitter to the skin. The transmitter may need to be recharged regularly but can be removed as needed. After a certain amount of time, the device may be replaced by a healthcare provider. The device may also be cleaned as provided herein after use for a period of time and thus does not need to be replaced. The device is programmed to conduct the cleaning and the glucose sensitivity determination automatically, and the user also has the option to trigger the cleaning and the glucose sensitivity determination any time they desire. Unlike traditional CGMs, which require frequent sensor changes, the device provided herein offers long-term wear, reducing the need for frequent replacements. The system, including the implantable device and any external ancillary device(s), provides continuous monitoring, offering real-time data and alerts for high and low glucose levels. This system provides accurate glucose tracking, trend analysis, and customizable alerts, making it a convenient option for diabetes management, ensuring that the user has continuous access to critical glucose data through a well-integrated combination of the nanoporous layer sensor technology; automatic and on-demand cleaning mechanisms, glucose sensitivity determination, and glucose measurement; and wireless communication and charging.

Implant Duration

After the implantable glucose sensor device is inserted into the user's body, it can be maintained in the user's body for a period of at least 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, at least 25 months, at least 26 months, at least 27 months, at least 28 months, at least 29 months, at least 30 months, at least 31 months, at least 32 months, at least 33 moths, at least 34 months, at least 35 months, or at least 36 months, and even longer.

EXAMPLES

Example 1: Nanoporous Layer Electrodes without Outer Membrane

Seven samples of glucose sensing electrodes with various amounts of platinum mesoporous layers were prepared. Generally, clusterized platinum nanoparticles were suspended in a liquid to provide a cluster colloid. Then, the cluster colloid is dispensed on a gold-plated conductive layer for producing each glucose sensing electrode with the nanoporous layer. The amount of platinum mesoporous layers was varied by varying the dispensed volume of the colloid. The seven electrodes with the colloids dropped thereon were then dried to form the samples of the glucose-sensing electrodes.

Example 1.1: Nanoparticles 36 g of non-ionic surfactant and 15 g of chloroplatinic acid hydrate are dissolved in deionized water (DIW) at room temperature for 24 hours. After the solution is heated to 50° C.,) ascorbic acid aqueous solution is slowly added, and the mixture is allowed to react and produce platinum nanoparticles for 48 hours. The reaction solution is centrifuged at 4,000 rpm for 10 minutes to remove the supernatant. The pellet is redispersed with 1.5 L of 1 M sodium hydroxide aqueous solution, and the supernatant is removed by centrifugation at 4,000 rpm for 10 minutes. This process is repeated twice. The pellet is redispersed with 1.3 L of DIW and centrifugation at 4,000 rpm for 10 minutes to remove the supernatant. This process is repeated 4 times. The washed pellet is lyophilized for 24 hours to prepare the power of platinum nanoparticles and nanoclusters.

Example 1.2: Nanoparticle Suspension (Ink)

1 g of binder and 1 g of Ethylene glycol diacetate are mixed with a magnetic stirrer at 80° C. for 12 hours. 0.28 g of the prepared binder solution, 0.7 g of mPt powder (UXN Co., Ltd., South Korea), and 0.05 g of Ethylene glycol diacetate (EGDA) are mixed in order. A Thinky mixer (Thinky Corporation, Japan) is used to remove the gas from the mixture at 2,000 rpm for 30 seconds, and this process is repeated 5 times in total. Additionally, a Homogenizer (T 10 basic ULTRA-TURRAX®, Germany) is used to stir the mixture 30 seconds, followed by 1 minute rest, which is repeated 50 times.

Example 1.3: Electrodes No. 1

Example 1.3.1: Preparation of Nanoporous Layer Electrode No. 1 as Working Electrode The prepared dispensing ink in Example 1.2 is dispensed on the gold electrode (prepared for a working electrode of sensor) using a digital dispenser (SuperSigma CMIII-V5, Musashi Engineering, Inc., Japan). Fill the syringe with 0.5 g of ink and discharge it with parameters of 0.100 s, 40.0 kPa, 0.9 mm application gap, and plate temperature: 45° C.

The amount of nanoparticle coated on the conducting layer of working electrode is controlled by the volume of each dispensed ink drops and the number of drops. Typically, about 3 to 10 µg of ink drop is repeatedly dispensed two to three times so that the surface of the conducting layer can be uniformly covered, and dispensing is performed while being careful not to form voids. The prepared electrode is dried at 80° C. for 30 minutes and cured at 150° C. for 1 to 3 hr. 1 drop (approximately 5 ug) of the nanoparticle suspension is used to prepare the nanoporous layer electrode No. 1 as a working electrode.

Example 1.3.2: Preparation of Nanoporous Layer Electrode as Counter Electrode Example 1.3.1 was repeated, except that nanoporous particle ink is dispensed on the gold electrode prepared for a counter electrode of sensor.

Example 1.3.3: Preparation of Reference Electrode

AgCl paste is dispensed on the gold electrode prepared for the reference electrode of the sensor using a digital dispenser. 0.5 g of Medical Grade Electrically Conductive Ink (Creative Materials, Inc., USA) is used as dispensing ink, and parameters of 0.100 s, 40.0 kPa, 0.9 mm application gap, and plate temperature 45° C. are used for the discharge. About 1 to 10 µg of ink is discharged and dispensed while being careful not to form voids. The manufactured electrode is dried at 80° C. for 30 min and cured at 150° C. for 1 to 3 hr.

Example 1.4: Electrodes No. 2

Example 1.3 was repeated, except that 1 drop (approximately 5 ug) of the nanoparticle suspension is used to prepare the nanoporous layer electrode No. 2 as a working electrode.

Example 1.5: Electrodes No. 3

Example 1.3 was repeated, except that 1 drop (approximately 5 ug) of the nanoparticle suspension is used to prepare the nanoporous layer electrode No. 3 as a working electrode.

Example 1.6: Electrodes No. 4

Example 1.3 was repeated, except that 2 drops (approximately 10 ug) of the nanoparticle suspension is used to prepare the nanoporous layer electrode No. 4 as a working electrode.

Example 1.7: Electrodes No. 5

Example 1.3 was repeated, except that 2 drops (approximately 10 ug) of the nanoparticle suspension is used to prepare the nanoporous layer electrode No. 5 as a working electrode.

Example 1.8: Electrodes No. 6

Example 1.3 was repeated, except that 1 drop (approximately 5 ug) of the nanoparticle suspension is used to prepare the nanoporous layer electrode No. 6 as a working electrode.

Example 1.9: Electrodes No. 7

Example 1.3 was repeated, except that 3 drops (approximately 10 ug) of the nanoparticle suspension is used to prepare the nanoporous layer electrode No. 7 as a working electrode.

Example 2: Glucose Sensitivities

Example 2.1: Glucose Stock Solution

D-(+)-glucose powder purchased from Sigma-Aldrich was dissolved in purified water to prepare 1 M glucose stock solution.

Example 2.2: Phosphate Buffered Saline 500 ml aqueous solution containing 0.1 M $NaH_2PO_4$ and 0.15 M NaCl in purified water was prepared. 500 ml aqueous solution containing 0.1 M $Na_2HPO_4$ and 0.15 M NaCl in purified water was prepared. The two aqueous solutions were mixed to prepare 1 L stock phosphate buffered saline (PBS) in pH 7.4.

Example 2.3: Glucose-Sensing System No. 1 in PBS 20 ml of the PBS prepared in Example 2.2 was placed in a beaker, in which the temperature of PBS was maintained at 37° C. The electrochemical cell (also referred to as "glucose-sensing system") of FIG. 1 was prepared using electrochemical analyzer CHI660 from CH Instruments Inc. as potentiostat 104 and using the nanoporous layer electrode No. 1 prepared in Example 1.3.1 as the working electrode 103, a platinum wire or the nanoporous layer electrode prepared in Example 1.3.2 as the counter electrode 105, and the Ag/AgCl (3 M KCl) or reference electrode prepared in Example 1.3.3 as the reference electrode 106. The gold layer of the electrode was connected to the potentiostat 104. The electrodes were submerged into PBS and electrically connected to the electrochemical analyzer.

Example 2.4: Glucose-Sensing System No. 2 in PBS

Example 2.3 was repeated, except that the nanoporous layer electrode No. 2 prepared in Example 1.4 was used as the working electrode 103.

Example 2.5: Glucose-Sensing System No. 3 in PBS

Example 2.3 was repeated, except that the nanoporous layer electrode No. 3 prepared in Example 1.5 was used as the working electrode 103.

Example 2.6: Glucose-Sensing System No. 4 in PBS

Example 2.3 was repeated, except that the nanoporous layer electrode No. 4 prepared in Example 1.6 was used as the working electrode 103.

Example 2.7: Glucose-Sensing System No. 5 in PBS

Example 2.3 was repeated, except that the nanoporous layer electrode No. 5 prepared in Example 1.7 was used as the working electrode 103.

Example 2.8: Glucose-Sensing System No. 6 in PBS

Example 2.3 was repeated, except that the nanoporous layer electrode No. 6 prepared in Example 1.8 was used as the working electrode 103.

Example 2.9: Glucose-Sensing System No. 7 in PBS

Example 2.3 was repeated, except that the nanoporous layer electrode No. 7 prepared in Example 1.9 was used as the working electrode 103.

Example 2.10: Electric Current by Glucose-Sensing System No. 1 in PBS

In the glucose-sensing system No. 1 prepared in Example 2.3, the bias voltage of 0.25 V was applied between the working electrode 103 and the reference electrode 106. Upon application of the bias voltage, electric current from the working electrode 103 was continuously measured. The electrochemical cell was kept for more than 10 minutes for conditioning the glucose-sensing system in PBS without addition of any substance thereto. Subsequently, the current value was taken for no glucose contained in the PBS.

Example 2.11: Electric Current by Glucose-Sensing System No. 1 from 5 mM Glucose in PBS After conditioning of the glucose-sensing system No. 1, 100 μl of the glucose stock solution prepared in Example 2.1 was added to the PBS of Example 2.2 to make 5 mM glucose in the PBS. Immediately after the addition, the glucose-added PBS was stirred for 3-4 seconds, which caused temporary peaks of electric current. The electric current from the working electrode was continuously measured. When the current became stable, the current value was taken for 5 mM glucose in PBS for the glucose-sensing system No. 1.

Example 2.12: Electric Current by Glucose-Sensing System No. 1 from 10 mM Glucose in PBS After the current became stable in Example 2.11, 100 μl of the glucose stock solution prepared in Example 2.1 was added to the PBS resulting from Example 2.11 to make the total glucose 10 mM in the PBS. Immediately after the addition, the glucose-added PBS was stirred for 3-4, seconds, which caused temporary peaks of electric current. The electric current from the working electrode was continuously measured. When the current became stable, the current value was taken for 10 mM glucose in PBS. The sensor sensitivity was calculated from the current values of PBS (0 mM glucose) and 10 mM glucose.

Example 2.13: Electric Currents by Glucose-Sensing System No. 2

Examples 2.10-2.12 were repeated for the glucose-sensing system No. 2.

Example 2.14: Electric Currents by Glucose-Sensing System No. 3

Examples 2.10 to 2.12 were repeated for the glucose-sensing system No. 3.

Example 2.15: Electric Currents by Glucose-Sensing System No. 4

Examples 2.10-2.12 were repeated for the glucose-sensing system No. 4.

Example 2.16: Electric Currents by Glucose-Sensing System No. 5

Examples 2.10-2.12 were repeated for the glucose-sensing system No. 5.

Example 2.17: Electric Currents by Glucose-Sensing System No. 6

Examples 2.10-2.12 were repeated for the glucose-sensing system No. 6.

Example 2.18: Electric Currents by Glucose-Sensing System No. 7

Examples 2.10-2.12 were repeated for the glucose-sensing system No. 7.

Example 2.19: Plotting Currents Over Time

The electric currents measured in Examples 2.10 to 2.18 were plotted against time in FIG. 10 for the glucose-sensing systems Nos. 1 to 7 to show the glucose-sensing systems' responses over time.

Example 2.20: Glucose Sensitivities

FIG. 10 shows an increase in the glucose concentration results in an increase in current and how the current reaches a new steady state after a change in the glucose concentration, indicating the sensor's ability to detect and quantify glucose levels. The slope of the current change in response to the glucose concentration changes indicates the sensor's sensitivity. The change in currents is divided by the difference in the glucose concentrations to obtain the glucose sensitivity of each sensing system. TABLE 1 shows the obtained current values of the seven glucose-sensing systems Nos. 1 to 7 in Examples 2.10 to 2.18 and their glucose sensitivity values calculated from their current values obtained in PBS (0 mM glucose) and 10 mM glucose.

TABLE 1

| Glucose-Sensing System No. | $I_0$ @ 0 mM Glucose in PBS (nA) | $I_5$ @ 5 mM Glucose in PBS (nA) | $I_{10}$ @ 10 mM Glucose in PBS (nA) | $\Delta I = I_{10} - I_0$ (nA) | $\Delta C$ (mM) | $\Delta I/\Delta C$ (nA/ mM) |
|---|---|---|---|---|---|---|
| 1 | −29.64 | −5.82 | 11.27 | 40.91 | 10 | 4.1 |
| 2 | −24.89 | −6.43 | 5.91 | 30.80 | 10 | 3.1 |
| 3 | −38.34 | −6.86 | 14.81 | 53.15 | 10 | 5.3 |
| 4 | −46.89 | −6.90 | 21.41 | 68.30 | 10 | 6.8 |
| 5 | −48.97 | −3.92 | 28.06 | 77.03 | 10 | 7.7 |
| 6 | −27.54 | −7.80 | 4.67 | 32.21 | 10 | 3.2 |
| 7 | −50.19 | 2.75 | 43.92 | 94.11 | 10 | 9.4 |

TABLE 1 calculated the glucose sensitivity used the current change when the glucose concentration went from 0 mM to 10 mM, but theoretically, calculation using any two of I0, I5, and I10 should result in the same sensitivity.

Example 3: Effective Surface Area

To investigate the effective surface area of the nanoporous layer electrodes Nos. 1 to 7 prepared in Examples 1.3 to 1.9, cyclic voltammetry (CV) was conducted in a potential range between 1.0 V and −1.0 V in PBS solution for each electrode. The cyclic voltammetry was performed with potential sweeping between −1.0 V and +1.0 V.

Example 3.1: Glucose-Sensing Systems Nos. A to H

Example 1.3 is repeated to prepare nanoporous layer electrodes Nos. A to H with varying amounts of nanoparticles, specifically, 3 drops (approximately 30 nl) for A, 1 drop (approximately 10 nl) for B, 3 drops (approximately 30 nl) for C, 3 drops (approximately 30 nl) for D, 2 drops (approximately 20 nl) for E, 3 drops (approximately 30 nl) for F, 3 drops (approximately 30 nl) for G, and 3 drops (approximately 30 nl) for H, respectively. Example 2.3 was repeated to prepare glucose-sending systems Nos. A to H with nanoporous layer electrodes Nos. A to H.

Example 3.2: Cyclic Voltammetry for Glucose-Sensing System No. A

The potential range was set from −1.0 V to +1.0 V and back to −1.0 V, forming a complete cycle. The scan rate was fixed at 10 mV/s unless otherwise stated. Electrical currents generated by the glucose-sensing system were taken. All experiments were conducted at room temperature (22±2° C.) under quiescent conditions. The data were recorded and analyzed using CHI660 potentiostat software.

Example 3.3: Cyclic Voltammetry for Glucose-Sensing System No. B

Example 3.2 was repeated for the glucose-sensing system No. B.

Example 3.4: Cyclic Voltammetry for Glucose-Sensing System No. C

Example 3.2 was repeated for the glucose-sensing system No. C.

Example 3.5: Cyclic Voltammetry for Glucose-Sensing System No. D

Example 3.2 was repeated for the glucose-sensing system No. D.

Example 3.6: Cyclic Voltammetry for Glucose-Sensing System No. E

Example 3.2 was repeated for the glucose-sensing system No. E.

Example 3.7: Cyclic Voltammetry for Glucose-Sensing System No. F

Example 3.2 was repeated for the glucose-sensing system No. F.

Example 3.8: Cyclic Voltammetry for Glucose-Sensing System No. G

Example 3.2 was repeated for the glucose-sensing system No. G.

Example 3.9: Cyclic Voltammetry for Glucose-Sensing System No. H

Example 3.2 was repeated for the glucose-sensing system No. H.

Example 3.10: Cyclic Voltammogram

Figure 11A:
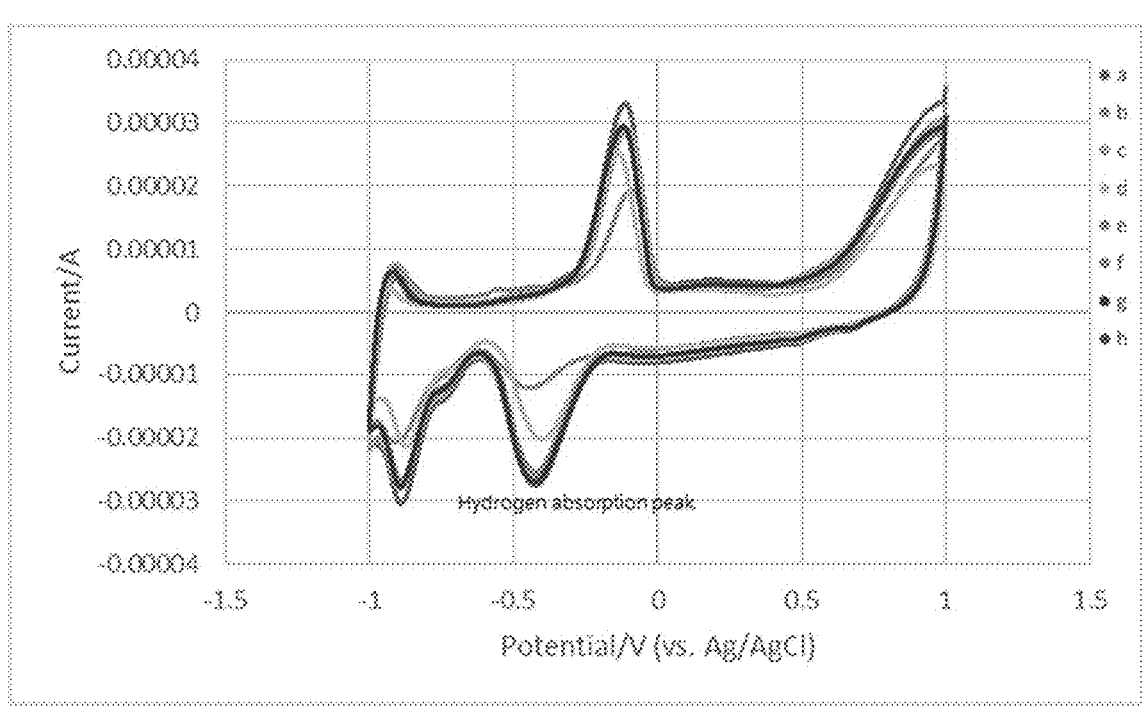
FIG. 11A shows the results of cyclic voltammograms for the sensors in Example 3.10.

The recorded electrical currents from Examples 3.2 to 3.9 were plotted against the voltage in the cyclic voltammogram in FIG. 11A for the glucose-sensing system Nos. A to H.

Example 3.11: Calculating Effective Surface Area

The current-potential curves were analyzed to identify oxidation and reduction peaks. The peak current Ip and peak potential Ep values were extracted. The amount of proton adsorbed to the surfaces of each nanoporous layer, i.e., the charge of the hydrogen adsorption peak, is proportional to the hydrogen adsorption area and thus the effective surface area of each sensor. The integrated charge (Q) values—the integrated areas under the hydrogen adsorption peaks—were extracted and divided by the charge density (210 $\mu$C/cm$^2$) of platinum to obtain the effective surface areas for the nanoporous layers Nos. a to h, as shown in TABLE 2.

TABLE 2

| Glucose-Sensing System No. | $I_p$ ($\mu$A) | $E_p$ (V) | Q ($\mu$C) | Effective Surface Area (ESA) (cm$^2$) |
|---|---|---|---|---|
| a | −20.03 | −0.427 | 199.4 | 0.949 |
| b | −6.02 | −0.452 | 63.4 | 0.302 |
| c | −18.26 | −0.428 | 183.7 | 0.874 |
| d | −19.10 | −0.437 | 196.5 | 0.935 |
| e | −15.32 | −0.405 | 152.3 | 0.725 |
| f | −19.20 | −0.423 | 197.7 | 0.941 |
| g | −19.88 | −0.424 | 207.8 | 0.989 |
| h | −20.63 | −0.431 | 216.5 | 1.030 |

Example 4: Impedance and Frequency

Example 4.1: Finding Frequency Range of
Nanoporous Layer Electrode No. 1

Figure 12B:
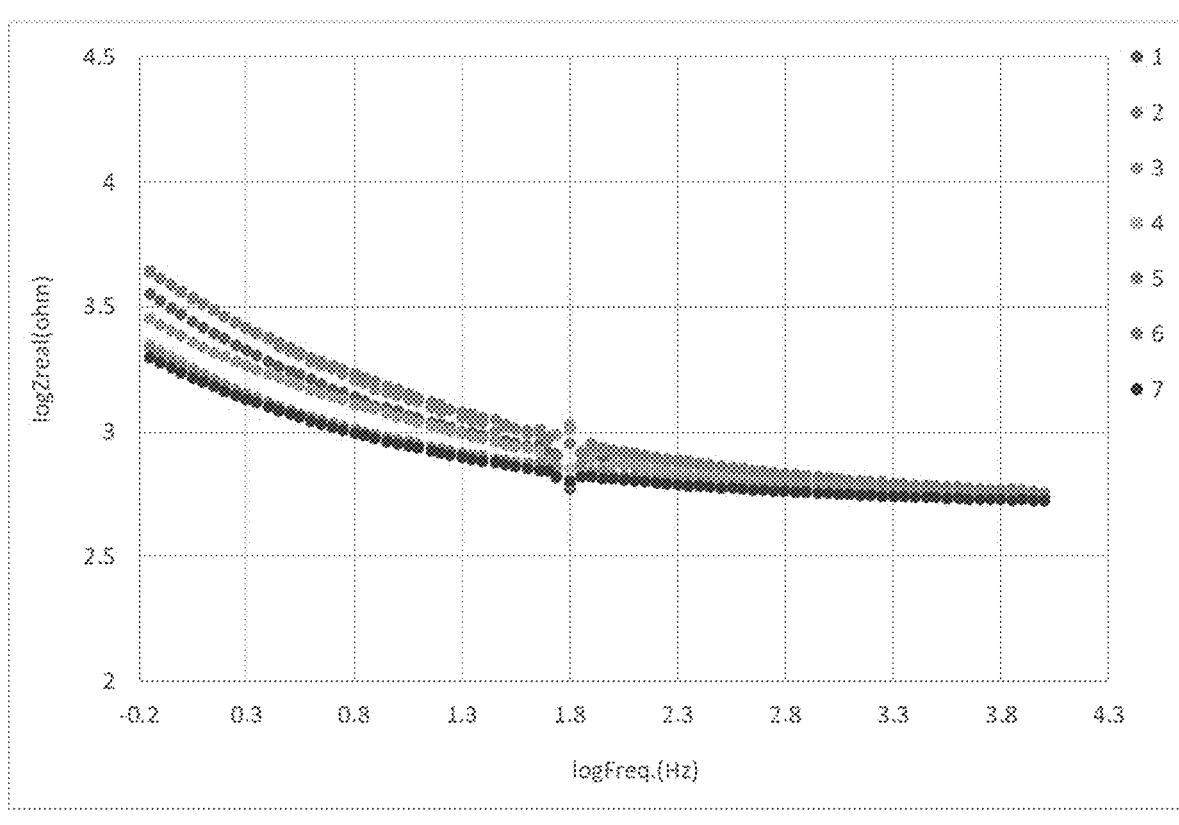
FIG. 12B is the plot of the real impedance (ZRe) vs. frequency (f) plotted to find the frequency range of the nanoporous layer electrodes used in FIG. 10.
Figure 12C:
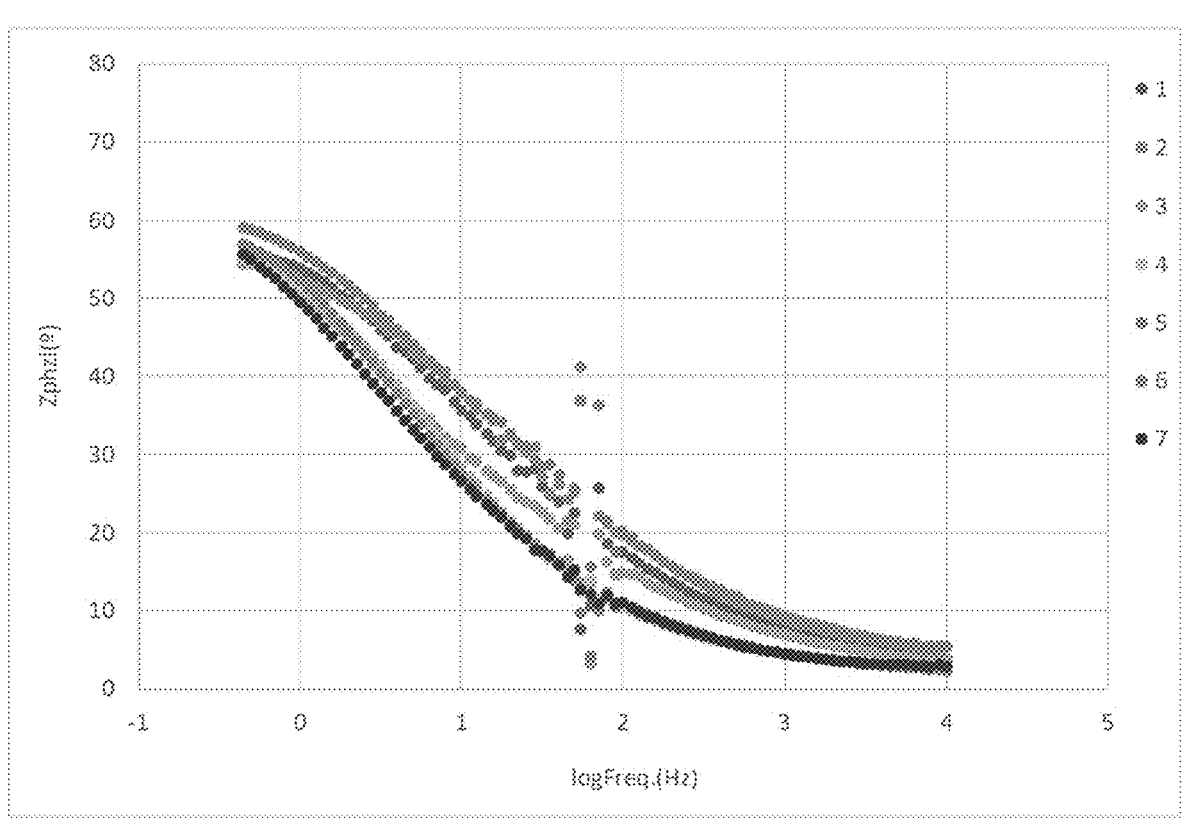
FIG. 12C is the impedance spectra (Phase vs frequency) plotted to find the frequency range of the nanoporous layer electrodes used in FIG. 10.

Impedance measurements were carried out with a potentiostat (Model: Gamry Interface 1010e) in a frequency range of 1 Hz to 1000 Hz. A sinusoidal voltage perturbation of 10 mV amplitude was applied, and the resulting current was recorded to extract the impedance data. The imaginary and real impedance values were plotted against the frequences in FIGS. 12A and 12B, respectively. The phase values were plotted against the frequences in FIG. 12C.

Example 4.2: Finding Frequency Range of
Nanoporous Layer Electrode No. 2

Example 4.1 was repeated with the glucose-sensing system No. 2 to find frequency range of the nanoporous layer electrode No. 2. The imaginary and real impedance values were plotted against the frequences in FIGS. 12A and 12B, respectively, and 7C. The phase values were plotted against the frequences in FIG. 12C.

Example 4.3: Finding Frequency Range of
Nanoporous Layer Electrode No. 3

Example 4.1 was repeated with the glucose-sensing system No. 3 to find frequency range of the nanoporous layer electrode No. 3. The imaginary and real impedance values were plotted against the frequences in FIGS. 12A and 12B, respectively. The phase values were plotted against the frequences in FIG. 12C.

Example 4.4: Finding Frequency Range of
Nanoporous Layer Electrode No. 4

Example 4.1 was repeated with the glucose-sensing system No. 4 to find frequency range of the nanoporous layer electrode No. 4. The imaginary and real impedance values were plotted against the frequences in FIGS. 12A and 12B, respectively. The phase values were plotted against the frequences in FIG. 12C.

Example 4.5: Finding Frequency Range of
Nanoporous Layer Electrode No. 5

Example 4.1 was repeated with the glucose-sensing system No. 5 to find frequency range of the nanoporous layer electrode No. 5. The imaginary and real impedance values were plotted against the frequences in FIGS. 12A and 12B, respectively. The phase values were plotted against the frequences in FIG. 12C.

Example 4.6: Finding Frequency Range of
Nanoporous Layer Electrode No. 6

Example 4.1 was repeated with the glucose-sensing system No. 6 to find frequency range of the nanoporous layer electrode No. 6. The imaginary and real impedance values were plotted against the frequences in FIGS. 12A and 12B, respectively. The phase values were plotted against the frequences in FIG. 12C.

Example 4.7: Finding Frequency Range of
Nanoporous Layer Electrode No. 7

Example 4.1 was repeated with the glucose-sensing system No. 6 to find frequency range of the nanoporous layer electrode No. 6. The imaginary and real impedance values were plotted against the frequences in FIGS. 12A and 12B, respectively. The phase values were plotted against the frequences in FIG. 12C.

Example 4.8: Impedance Spectra in Frequency
Range

The imaginary impedance log values of the nanoporous layer electrodes Nos. 1 to 7 obtained in Examples 4.1 to 4.7 were plotted against the log of frequencies in FIG. 12A. FIG. 12A shows the imaginary impedance values of the seven sensors in the frequency range of 0.1 to 10 KHz. Nanoporous layer electrodes with different sensitivities have different ZIm values because the amounts of the nanoparticles and thus the effective surface areas of the nanoporous layers are different. Further, this figure shows that the seven nanoporous layer electrodes with different sensitivities have different impedance values show similar characteristics for the change of frequency. log $Z_{Im}$ is linear to log w with common slope estimated to be $-\alpha$. This trend is observed across the frequency range between 1 and 1000 Hz. Thus, Equation 5 and Equation 7 are valid in this frequency range in this frequency range, and the double layer capacitance Cdl is linear to the inverse of the imaginary impedance (1/ZIm). Generally, the double layer capacitance is proportional to the electrochemically active surface area. Thus, the more nanoparticles or nanoporous layer, the smaller imaginary impedance, the larger double layer capacitance, the larger the effective surface area, and the higher the sensitivity.

Examples 4.9-4.16: Finding Frequency Ranges of
Nanoporous Layer Electrodes Nos. a to h Example 4.1 was repeated with the glucose-sensing systems Nos. a to h to find the frequency ranges of the nanoporous layer electrodes Nos. a to h. The log imaginary impedance values were plotted against the log frequencies in FIG. 11B.

Example 5: Effective Surface Area and Impedance

Example 5.1: Plotting Charge Against Impedance

Figure 11B:
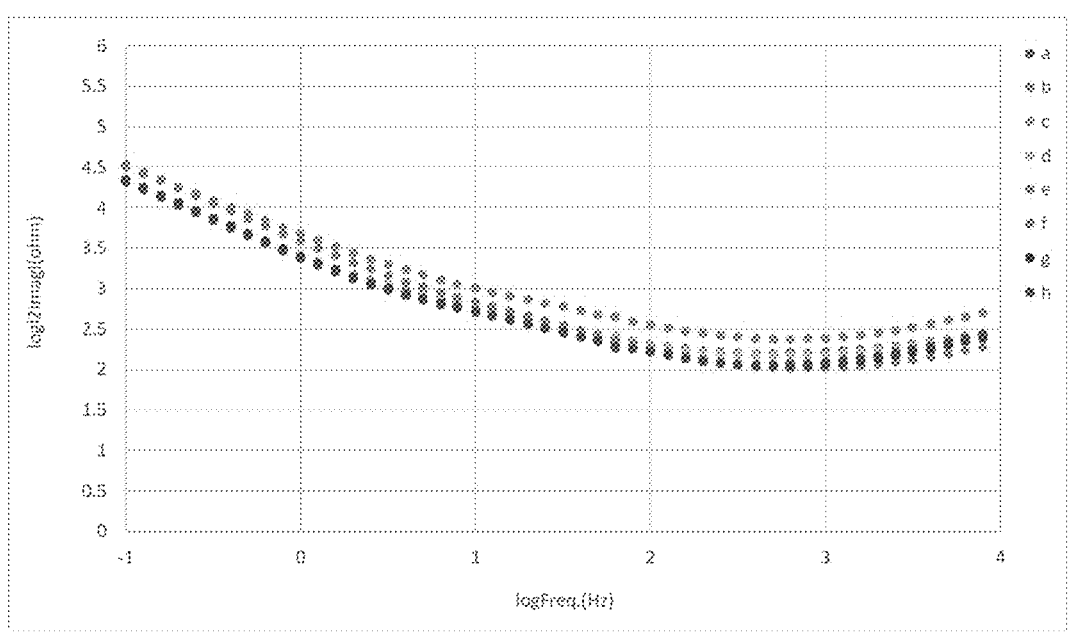
FIG. 11B is the impedance spectra plotted to find the frequency range of the sensors in Examples 4.9-4.16.
Figure 11C:
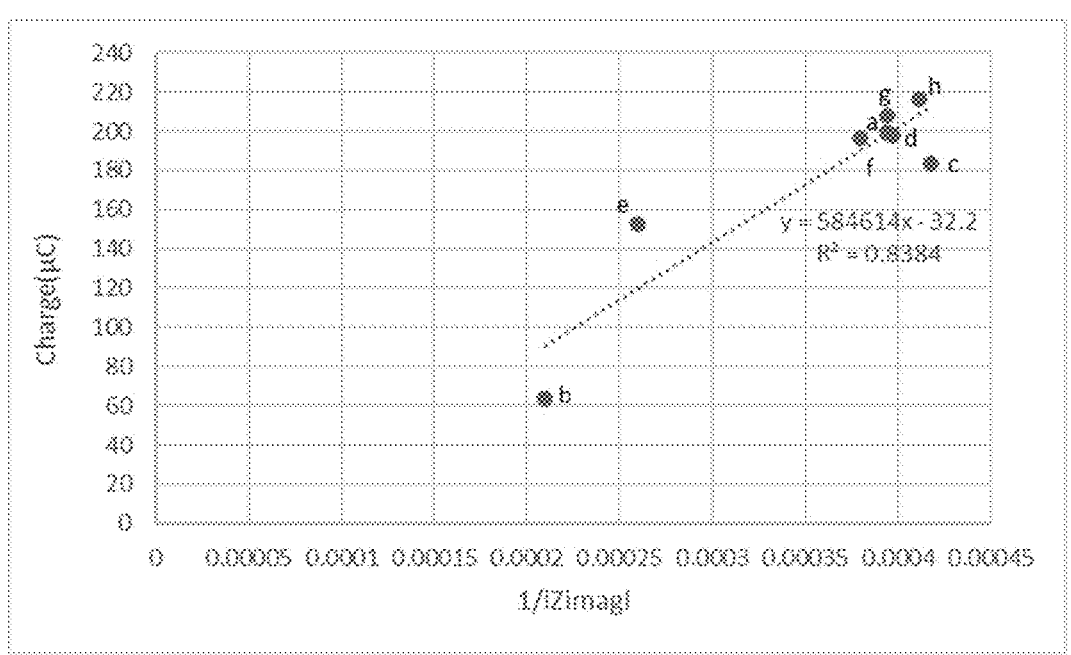
FIG. 11C shows the correlation between the charges obtained in FIG. 11A and the reverse of imaginary impedance values at 1 Hz obtained in FIG. 11B.

The integrated charge (Q) values of the glucose-sensing systems Nos. a to h obtained in Example 3.11 were plotted against the inverse of the impedance imaginary values at 1 Hz obtained in Examples 4.9 to 4.16 from FIG. 11B, as shown in TABLE 3, in FIG. 11C.

TABLE 3

| Glucose-sending Systems No. | Q (μC) | $1/Z_{im}$ at 1 Hz |
|---|---|---|
| a | 199.4 | $3.94 \times 10^{-4}$ |
| b | 63.42 | $2.10 \times 10^{-4}$ |
| c | 183.7 | $4.18 \times 10^{-4}$ |
| d | 196.5 | $3.80 \times 10^{-4}$ |
| e | 152.3 | $2.60 \times 10^{-4}$ |
| f | 197.7 | $3.97 \times 10^{-4}$ |
| g | 207.8 | $3.94 \times 10^{-4}$ |
| h | 216.5 | $4.12 \times 10^{-4}$ |

Example 5.2: Linear Fitting

A linear fitting of the plot in FIG. 11C shows that the charge of the hydrogen adsorption peak (uC) and the 1/Zim value have a linear relationship represented by Equation 8 with k=5.85×10$^5$, and 1=32.2.

$$Q=k(1/Z_{Im})+l \qquad \text{Equation 8}$$

As previously discussed, the charge of the hydrogen adsorption peak is proportional to the effective surface area of the sensor, and the 1/Zim value is also proportional to the effective surface area of the sensor. As such, the charge of the hydrogen adsorption peak (uC) and the 1/Zim value should also be proportional to each other. The linear fitting may show a linear relationship instead of a direct proportional relationship because of deviations from theoretical values due to factors such as the system setup, experimental conditions, and measurement errors, etc. The obtained hydrogen adsorption peak charge and/or 1/Zim value may not have a strict proportional relationship with the effective surface area and should at least have a linear relationship with the deviations, and thus the obtained hydrogen adsorption peak charge and the 1/Zim value at least have a linear relationship.

Example 6: Impedance and Glucose Sensitivity

Example 6.1: Plotting Impedance Against Glucose Sensitivity

Figure 14A:
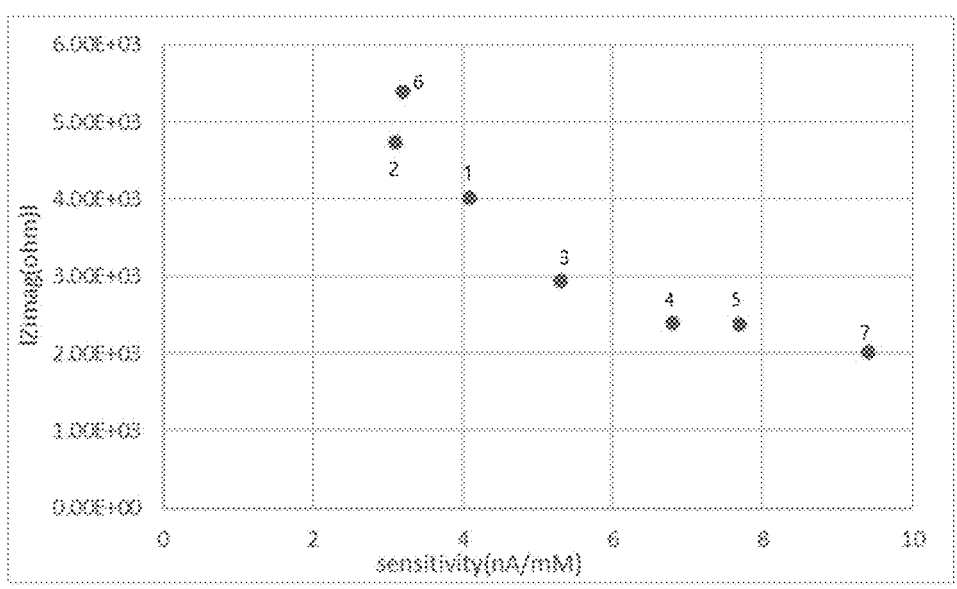
FIG. 14A is the plot of the imaginary impedance (ZIm) vs. the sensitivity of seven sensors in FIG. 10 at 1 Hz.
Figure 14B:
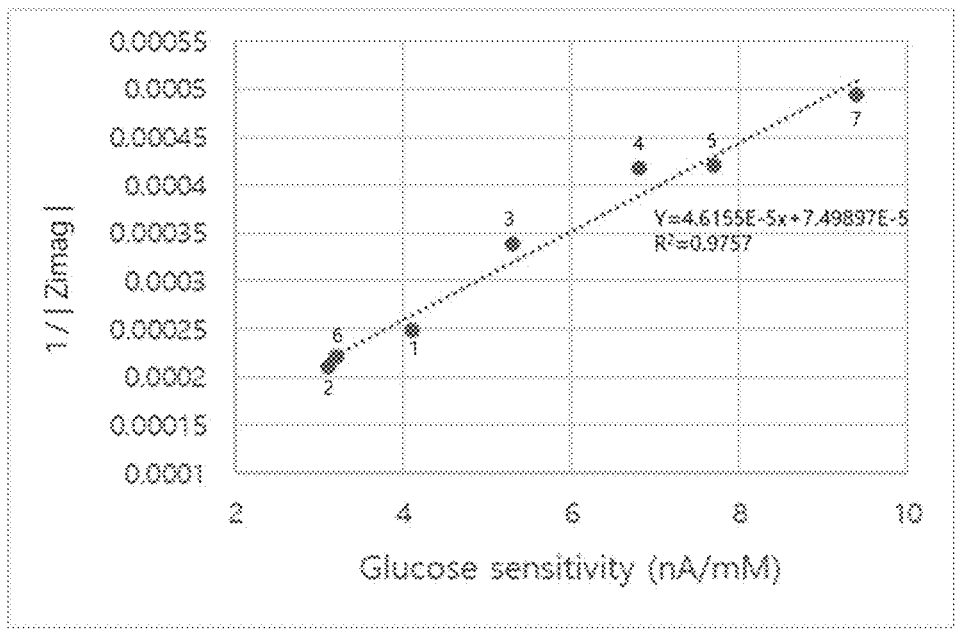
FIG. 14B is the plot of the inverse of imaginary impedance (1/ZIm) vs. the sensitivity of seven sensors in FIG. 10 at 1 Hz.
Figure 15A:
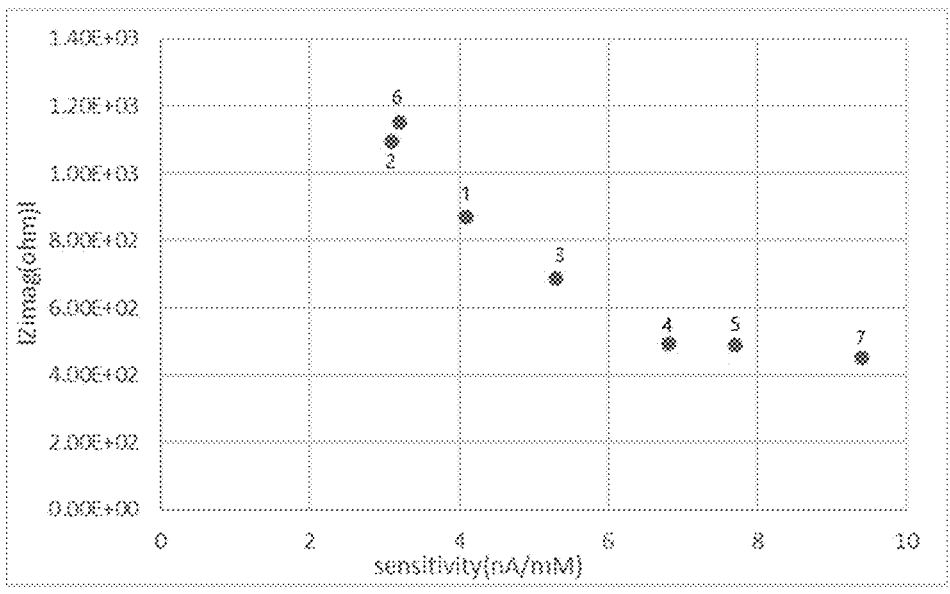
FIG. 15A is the plot of the imaginary impedance (ZIm) vs. the sensitivity of seven sensors in FIG. 10 at 10 Hz.
Figure 15B:
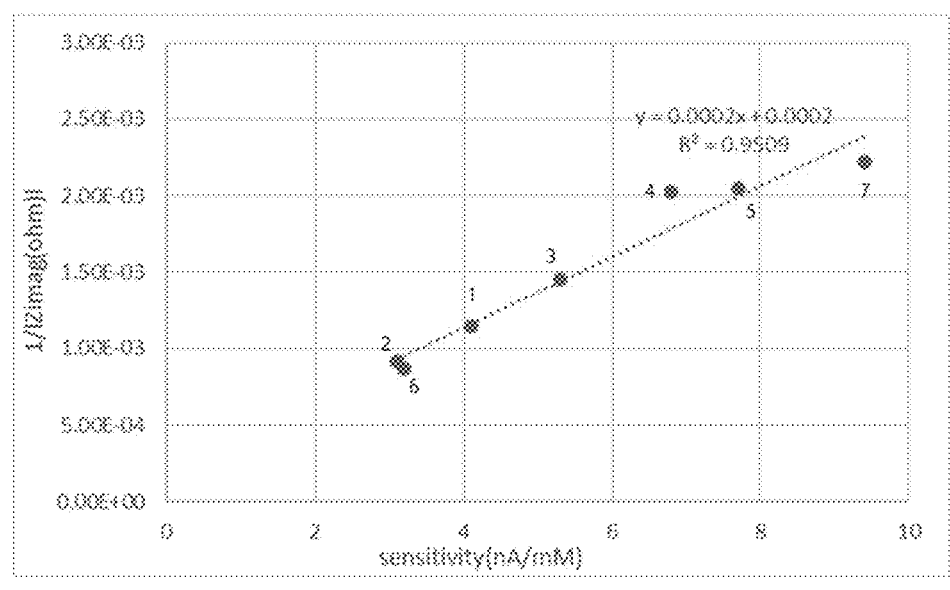
FIG. 15B is the plot of the inverse of imaginary impedance (1/ZIm) vs. the sensitivity of seven sensors in FIG. 10 at 10 Hz.
Figure 16A:
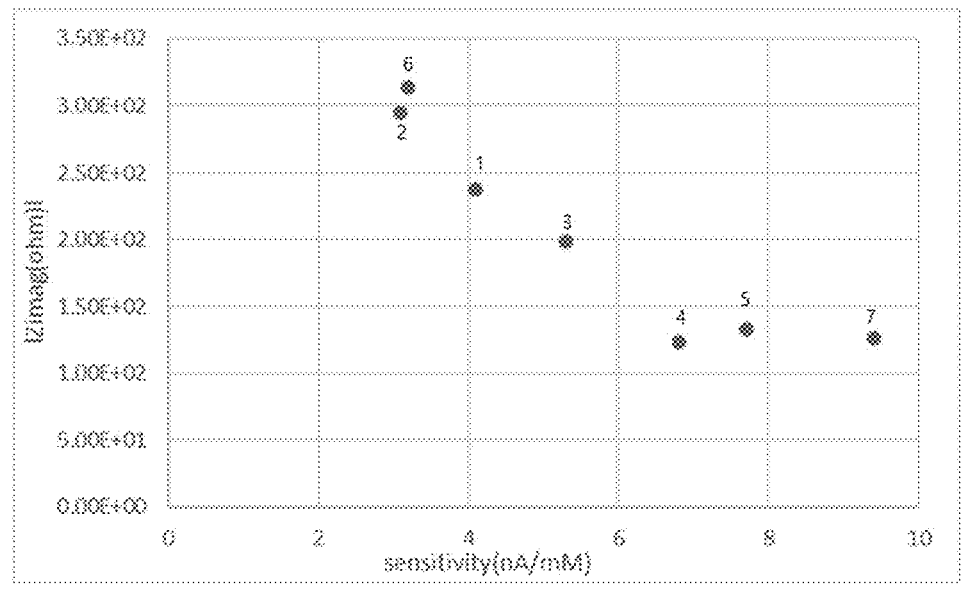
FIG. 16A is the plot of the imaginary impedance (ZIm) vs. the sensitivity of seven sensors in FIG. 10 at 100 Hz.
Figure 16B:
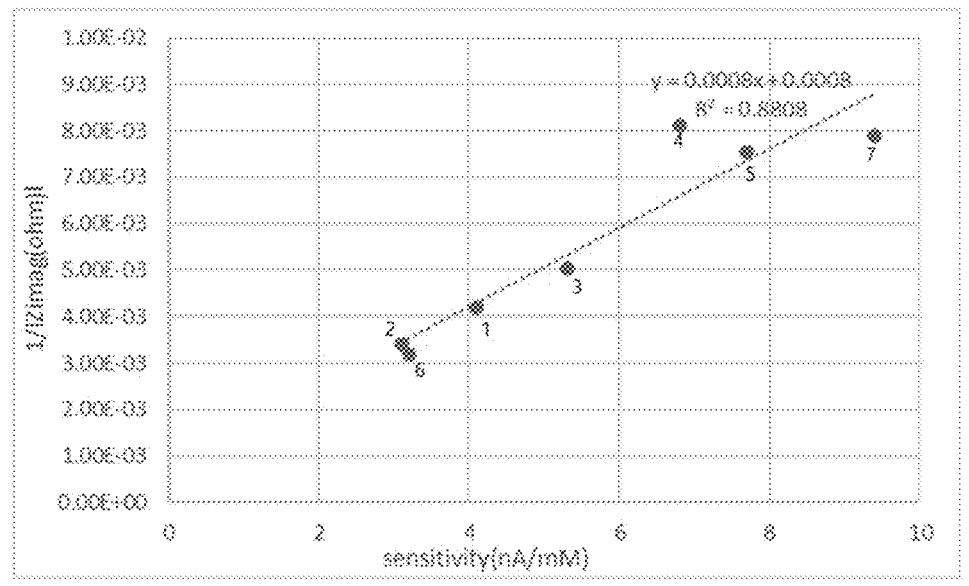
FIG. 16B is the plot of the inverse of imaginary impedance (1/ZIm) vs. the sensitivity of seven sensors in FIG. 10 at 100 Hz.
Figure 17A:
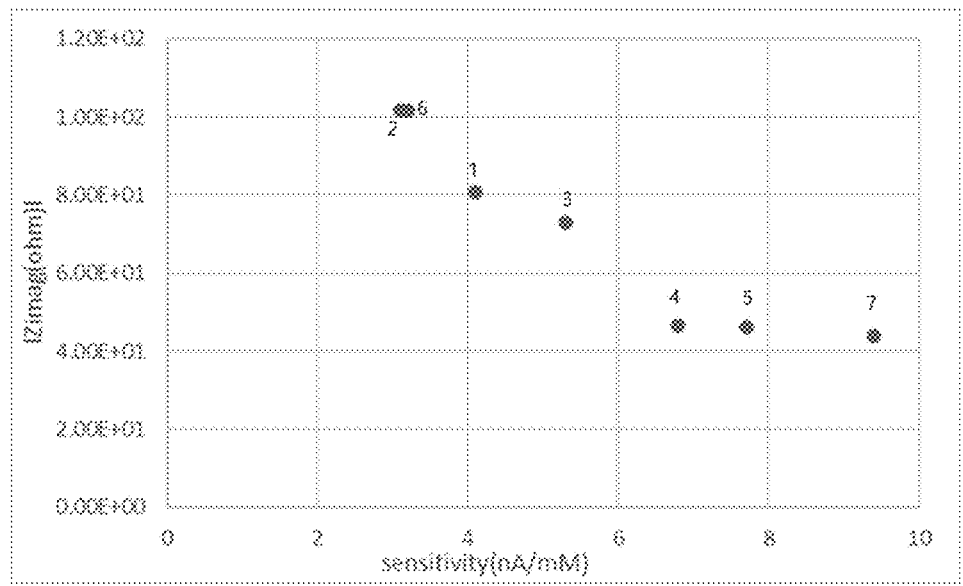
FIG. 17A is the plot of the imaginary impedance (ZIm) vs. the sensitivity of seven sensors in FIG. 10 at 1 k Hz.
Figure 17B:
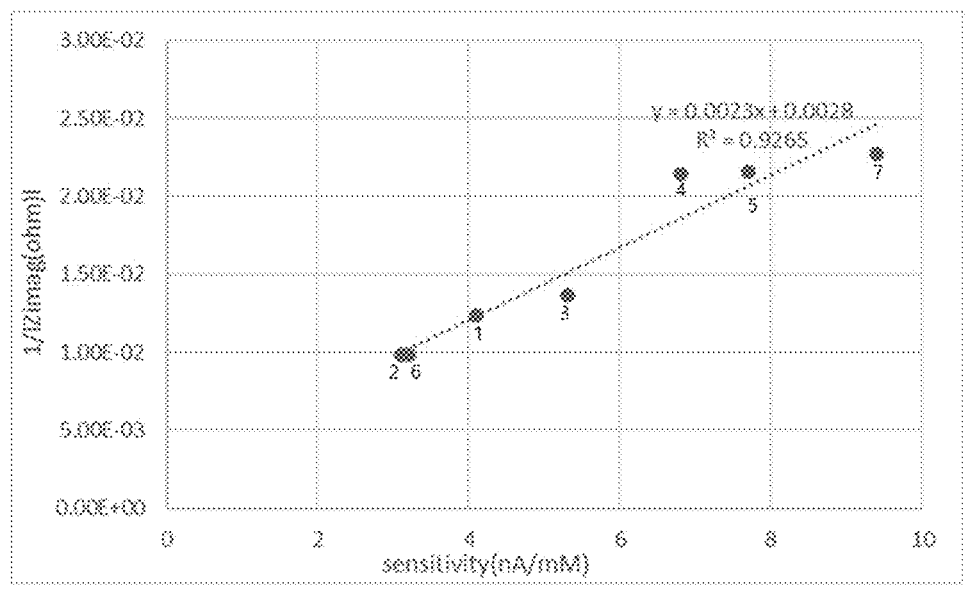
FIG. 17B is the plot of the reverse of imaginary impedance (1/ZIm) vs. the sensitivity of seven sensors in FIG. 10 at 1 k Hz.
Figure 18A:
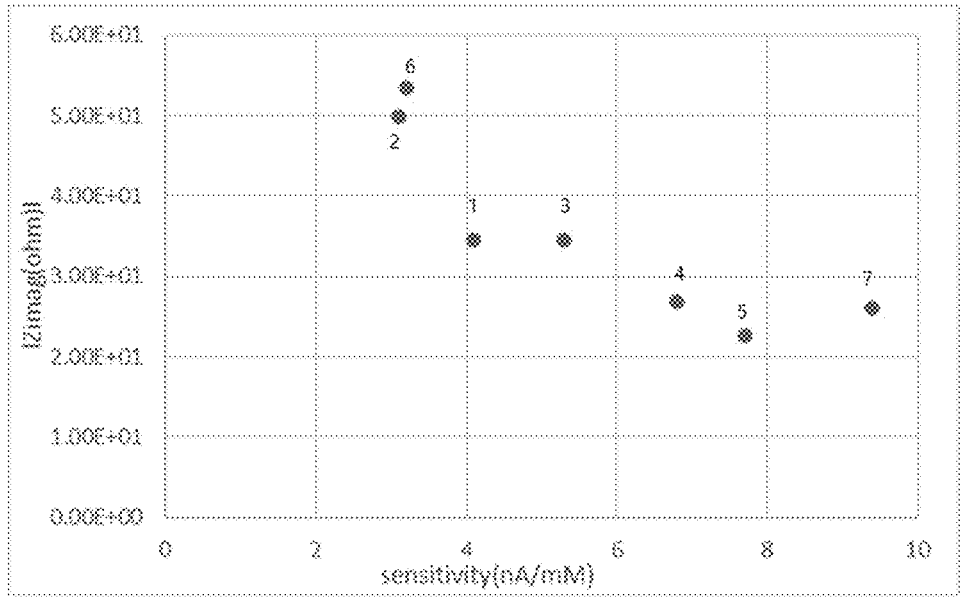
FIG. 18A is the plot of the imaginary impedance (ZIm) vs. the sensitivity of seven sensors in FIG. 10 at 10 k Hz.
Figure 18B:
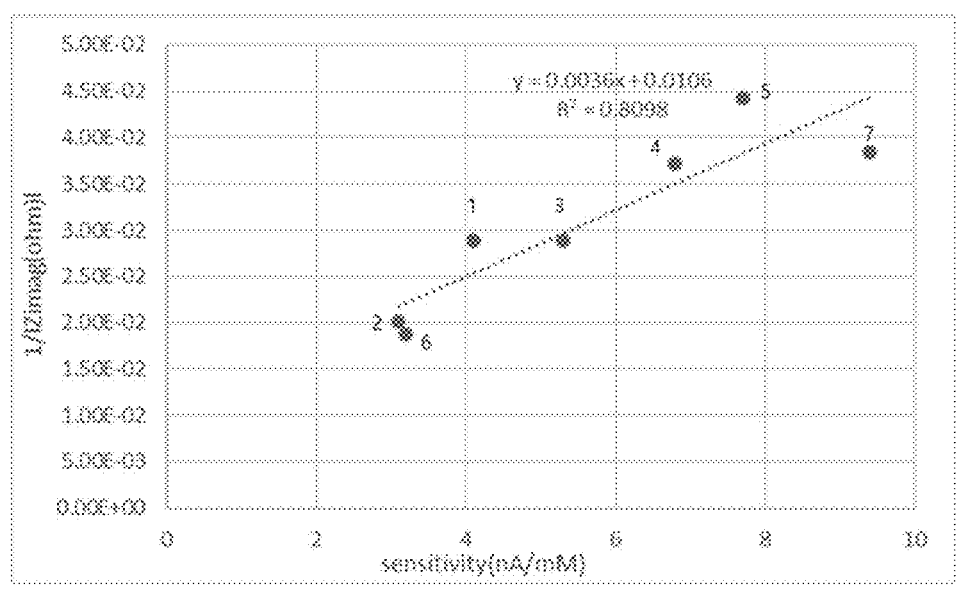
FIG. 18B is the plot of the inverse of imaginary impedance (1/ZIm) vs. the sensitivity of seven sensors in FIG. 10 at 10 k Hz.

Values of the absolute imaginary impedance, namely the Zim values, and the inverse of the absolute imaginary impedance, namely the 1/Zim values, of the impedance spectra of the glucose-sensing systems Nos. 1 to 7 at 1 Hz obtained in Example 4.8, from FIG. 12A were plotted against the glucose sensitivities of these systems obtained in Example 2.20, as shown in TABLE 4, in FIGS. 14A and 14B, respectively.

TABLE 4

| Sensor No. | $Z_{im}$ at 1 Hz | $1/Z_{im}$ at 1 Hz | S ($\Delta I/\Delta C$) (nA/mM) |
|---|---|---|---|
| 1 | 4.03 × 10$^3$ | 2.48 × 10$^{-4}$ | 4.1 |
| 2 | 4.74 × 10$^3$ | 2.11 × 10$^{-4}$ | 3.1 |
| 3 | 2.95 × 10$^3$ | 3.39 × 10$^{-4}$ | 5.3 |
| 4 | 2.39 × 10$^3$ | 4.18 × 10$^{-4}$ | 6.8 |
| 5 | 2.38 × 10$^3$ | 4.20 × 10$^{-4}$ | 7.7 |
| 6 | 5.38 × 10$^3$ | 1.86 × 10$^{-4}$ | 3.2 |
| 7 | 2.02 × 10$^3$ | 4.95 × 10$^{-4}$ | 9.4 |

Example 6.2: Linear Fitting

The linear fitting of FIG. 14B shows a linear relationship between 1/|Zimag| and glucose sensitivity of the sensors as represented by y=4.6155E-5 x+7.49897E-5 (Equation a).

Example 6.3: Calculated Glucose Sensitivity of Nanoporous Layer Electrode No. 1

Once the relationship between 1/|Zimag| and glucose sensitivity has been established, glucose sensitivity can be calculated using Equation a and the obtained 1/|Zimag| values. For the nanoporous layer electrode No. 1, as shown in TABLE 4, the 1/|Zimag| value at 1 Hz is 2.48E-04, which is y in Equation a. Thus, x is calculated as (2.48E-04-7.49897E-5)/4.6155E-5, which equals to 3.6 nA/mM. Thus, the "calculated" glucose sensitivity of the nanoporous layer electrode No. 1 is 3.6 nA/mM.

Example 6.4: Difference Between "Actual" and "Calculated" Sensitivities of Nanoporous Layer Electrode No. 1

As obtained in Example 2.20, the "actual" glucose sensitivity of the nanoporous layer electrode No. 1 is 4.1 nA/mM. The difference between the "actual" glucose sensitivity 4.1 nA/mM and the "calculated" glucose sensitivity is the "calculated" sensitivity minus the "actual" sensitivity, namely, 3.6 nA/mM-4.1 nA/mM, which is –0.5 nA/mM.

Example 6.5: Sensitivity Error Rate of Nanoporous Layer Electrode No. 1

The error rate of the nanoporous layer No. 1's glucose sensitivity is the difference obtained in Example 6.4 divided by the "actual" sensitivity, namely, –0.5 nA/mM/4.1 nA/mM, which is about –12%.

Example 6.6: Sensitivity Error Rate of Nanoporous Layer Electrode No. 2

Examples 6.3 to 6.5 are repeated for the nanoporous layer electrode No. 2 to obtain the calculated glucose sensitivity and the error rate of this electrode's sensitivity.

Example 6.7: Sensitivity Error Rate of Nanoporous Layer Electrode No. 3

Examples 6.3 to 6.5 are repeated for the nanoporous layer electrode No. 3 to obtain the calculated glucose sensitivity and the error rate of this electrode's sensitivity.

Example 6.8: Sensitivity Error Rate of Nanoporous Layer Electrode No. 4

Examples 6.3 to 6.5 are repeated for the nanoporous layer electrode No. 4 to obtain the calculated glucose sensitivity and the error rate of this electrode's sensitivity.

Example 6.9: Sensitivity Error Rate of Nanoporous Layer Electrode No. 5

Examples 6.3 to 6.5 are repeated for the nanoporous layer electrode No. 5 to obtain the calculated glucose sensitivity and the error rate of this electrode's sensitivity.

Example 6.10: Sensitivity Error Rate of Nanoporous Layer Electrode No. 6

Examples 6.3 to 6.5 are repeated for the nanoporous layer electrode No. 6 to obtain the calculated glucose sensitivity and the error rate of this e electrode's sensitivity.

Example 6.11: Sensitivity Error Rate of Nanoporous Layer Electrode No. 7

Examples 6.3 to 6.5 are repeated for the nanoporous layer electrode No. 7 to obtain the calculated glucose sensitivity and the error rate of this electrode's sensitivity.

The results from Examples 6.3 to 6.11 are provided in TABLE 5.

53

TABLE 5

| Sensor No. | S (nA/mM) | $1/Z_{im}$ at 1 Hz | $S_{cal}$ (nA/mM) | $\Delta S$ | Error Rate (%) |
|---|---|---|---|---|---|
| 1 | 4.1 | $2.48 \times 10^{-4}$ | 3.6 | −0.5 | −12 |
| 2 | 3.1 | $2.11 \times 10^{-4}$ | 2.8 | −0.3 | −10 |
| 3 | 5.3 | $3.39 \times 10^{-4}$ | 5.4 | 0.1 | 2 |
| 4 | 6.8 | $4.18 \times 10^{-4}$ | 7.0 | 0.2 | 3 |
| 5 | 7.7 | $4.20 \times 10^{-4}$ | 7.0 | −0.7 | −9 |
| 6 | 3.2 | $1.86 \times 10^{-4}$ | 3.0 | −0.2 | −6 |
| 7 | 9.4 | $4.95 \times 10^{-4}$ | 8.5 | −0.9 | −10 |

S: Actual sensor sensitivity for glucose $S_{cal}$: Calculated sensor sensitivity for glucose $\Delta S$: Difference between actual and calculated sensitivity, $S_{cal}-S$

Example 6.12: Correlation Between Imaginary Impedance and Glucose Sensitivity at Different Frequencies Examples 6.1 to 6.2 are repeated for the nanoporous layer electrodes Nos. 1 to 7 at 10 Hz, 100 Hz, 1 k Hz, and 10 k Hz, except that the real. The Zim values and the 1/Zim values of the glucose-sensing systems Nos. 1 to 7 at these frequencies obtained in Example 4.8, from FIG. 12B were plotted against the glucose sensitivities of these systems obtained in Example 2.20 in FIGS. 15A and 15B (10 Hz), 16A and 16B (100 Hz), 17A and 17B (1 k Hz), 18A and 18B (10 k Hz), respectively.

Figure 19A:
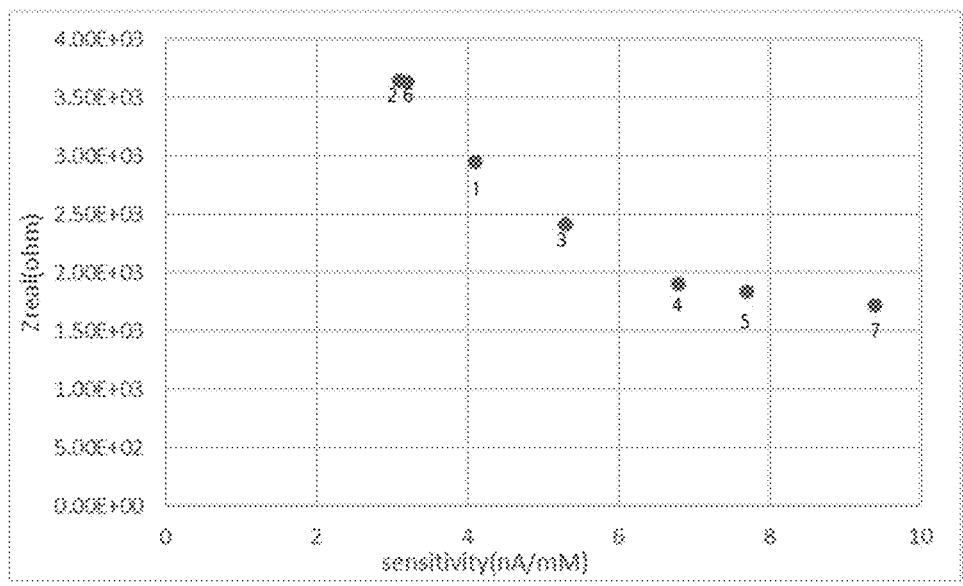
FIG. 19A shows the plot of the real impedance (ZRe) vs. the sensitivity of seven sensors in FIG. 10 at 1 Hz.
Figure 19B:
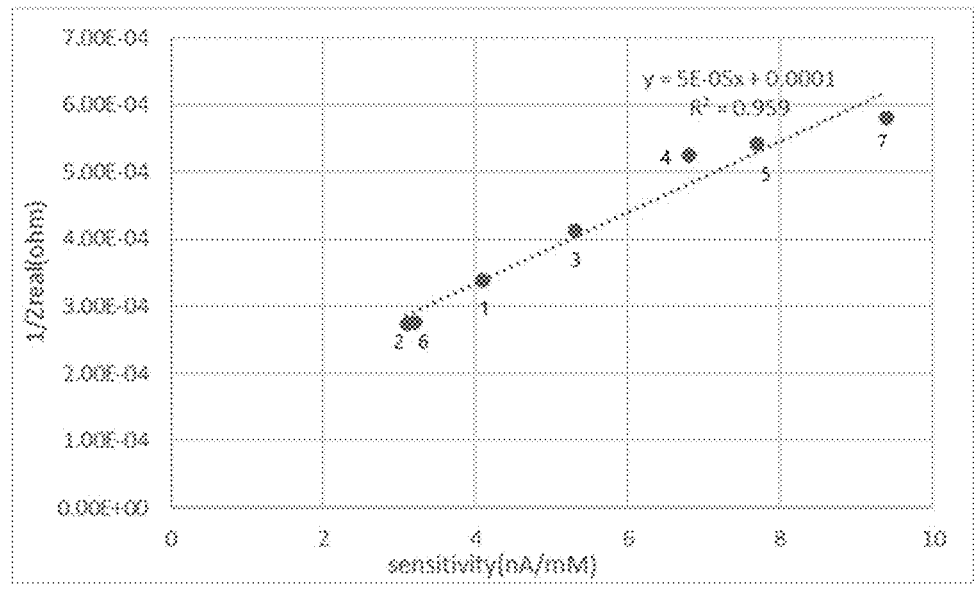
FIG. 19B shows the plot of the inverse of the real impedance (1/ZRe) vs. the sensitivity of seven sensors in FIG. 10 at 1 Hz.
Figure 20A:
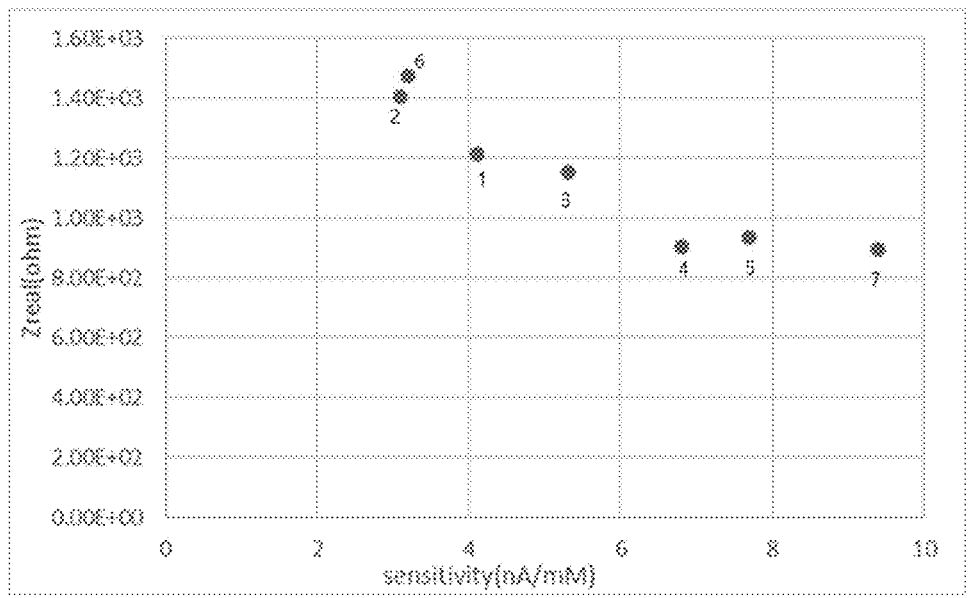
FIG. 20A shows the plot of the real impedance (ZRe) vs. the sensitivity of seven sensors in FIG. 10 at 10 Hz.
Figure 20B:
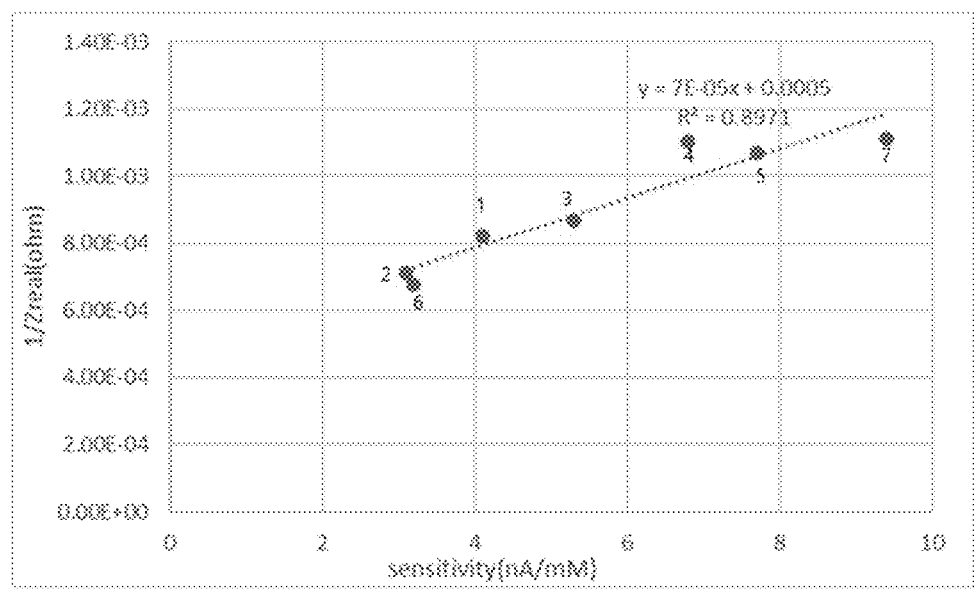
FIG. 20B shows the plot of the reverse of real impedance (1/ZRe) vs. the sensitivity of seven sensors in FIG. 10 at 10 Hz.
Figure 21A:
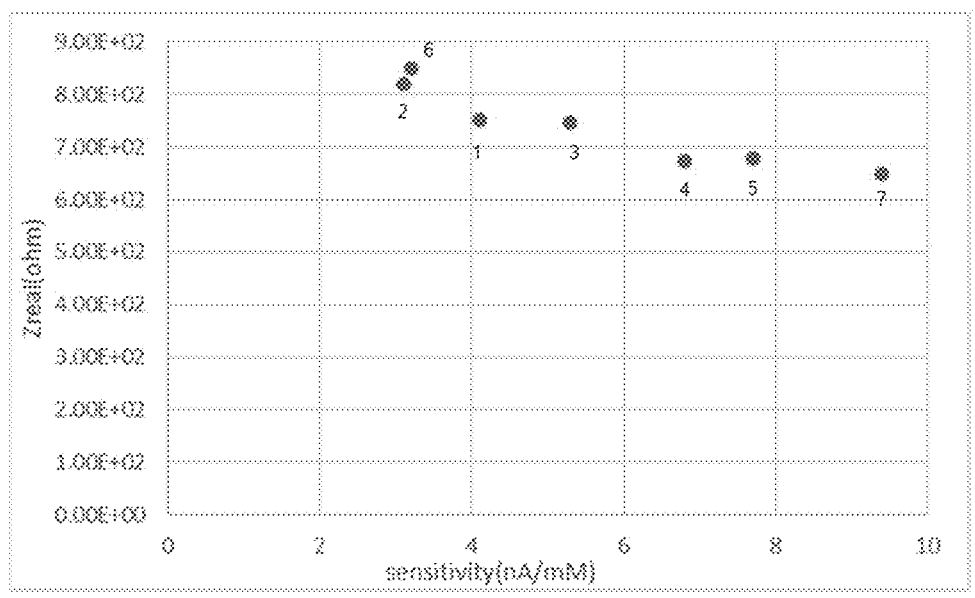
FIG. 21A shows the plot of the real impedance (ZRe) vs. the sensitivity of seven sensors in FIG. 10 at 100 Hz.
Figure 21B:
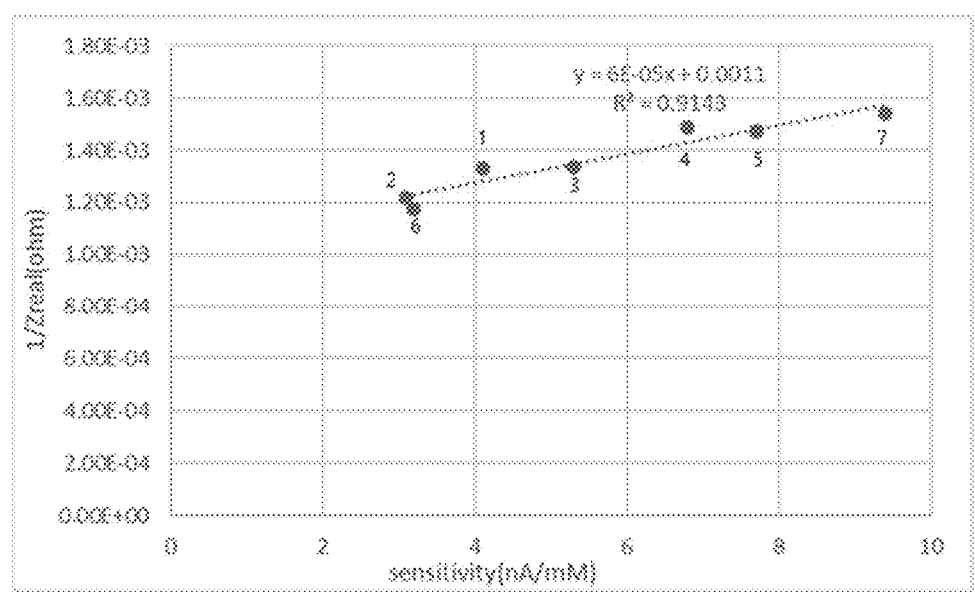
FIG. 21B shows the plot of the inverse of real impedance (1/ZRe) vs. the sensitivity of seven sensors in FIG. 10 at 100 Hz.
Figure 22A:
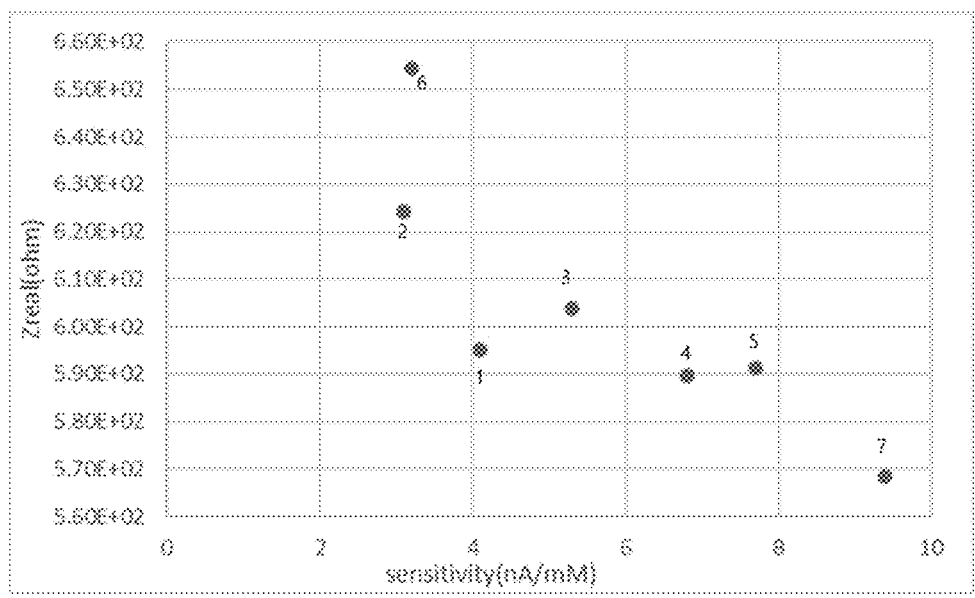
FIG. 22A shows the plot of the real impedance (ZRe) vs. the sensitivity of seven sensors in FIG. 10 at 1 k Hz.
Figure 22B:
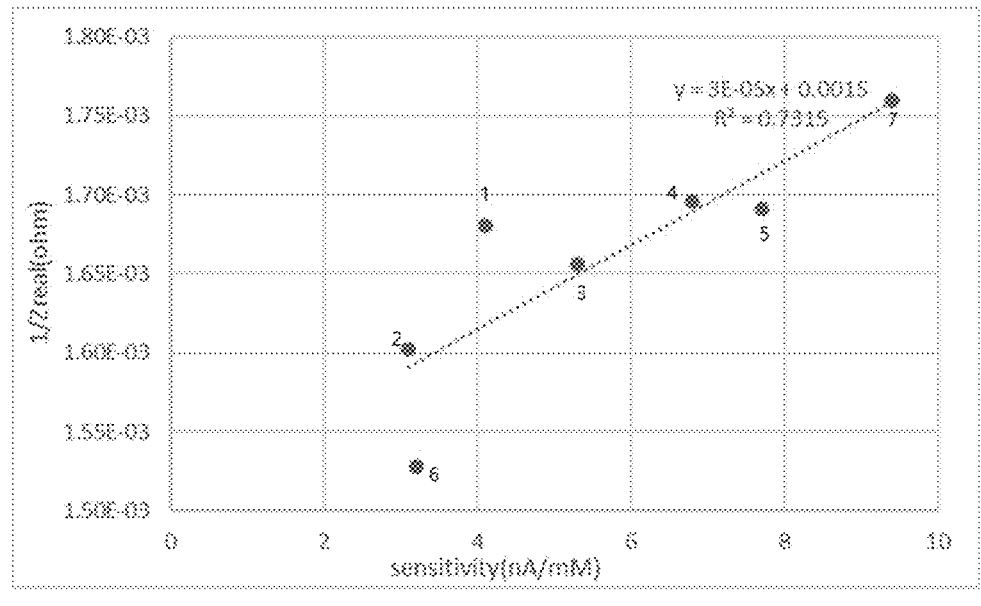
FIG. 22B shows the plot of the reverse of real impedance (1/ZRe) vs. the sensitivity of seven sensors in FIG. 10 at 1 k Hz.
Figure 23A:
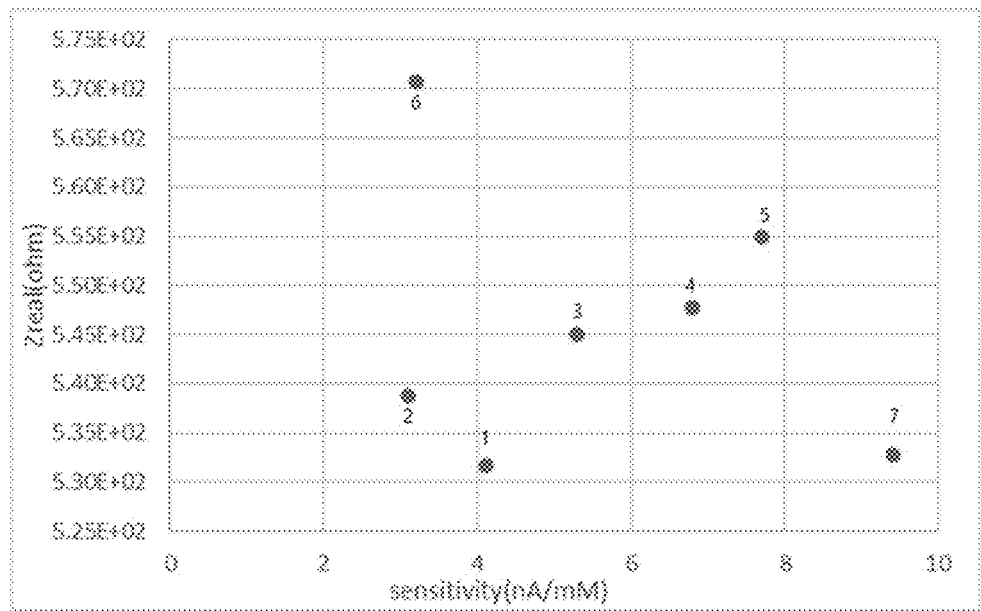
FIG. 23A shows the plot of the real impedance (ZRe) vs. the sensitivity of seven sensors in FIG. 10 at 10 k Hz.
Figure 23B:
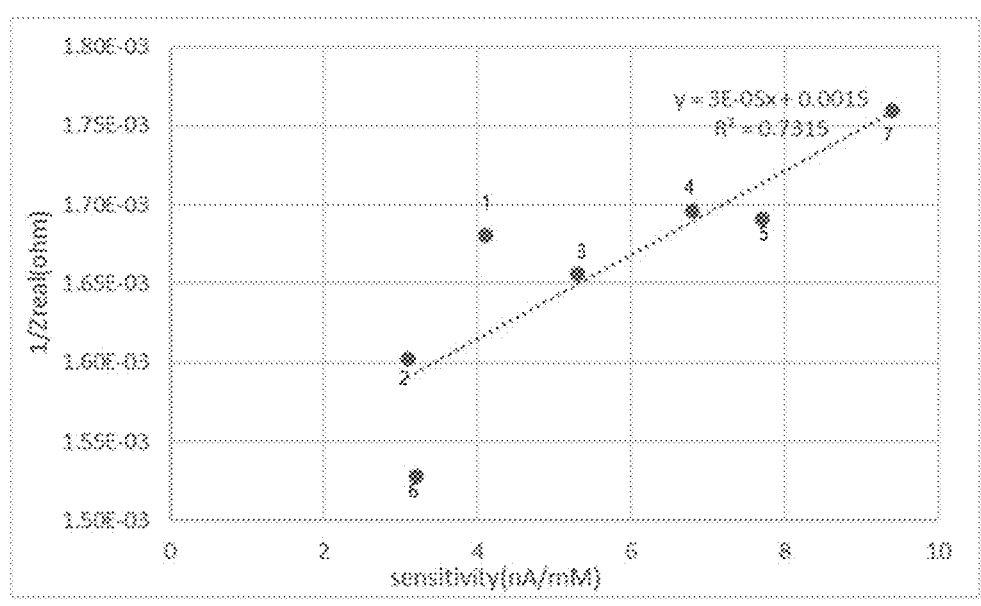
FIG. 23B shows the plot of the reverse of real impedance (1/ZRe) vs. the sensitivity of seven sensors in FIG. 10 at 10 k Hz.

Example 6.13: Correlation Between Real Impedance and Glucose Sensitivity at Different Frequencies Examples 6.1 to 6.2 are repeated for the glucose-sensing systems Nos. 1 to 7 at 1 Hz, 10 Hz, 100 Hz, 1 k Hz, and 10 k Hz, except that the Zreal values and the 1/Zreal values of the glucose-sensing systems Nos. 1 to 7 at these frequencies obtained in Example 4.8, from FIG. 12B were plotted against the glucose sensitivities of these systems obtained in Example 2.20 in FIGS. 19A and 19B (1 Hz), FIGS. 20A and 20B (10 Hz), 21A and 21B (100 Hz), 22A and 22B (1 k Hz), 23A and 23B (10 k Hz), respectively.

Example 7: Nanoporous Layers Electrode with Outer Membrane

Example 7.1: Nanoporous Layer Electrode with Outer Membrane No. 8

Figure 24:
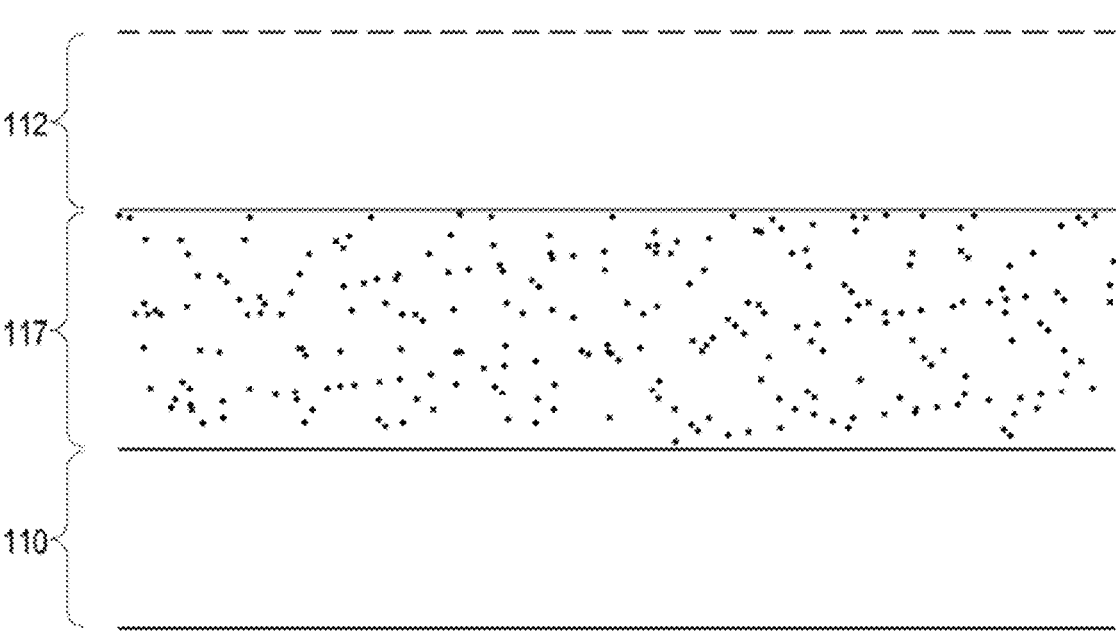
FIG. 24 illustrates layers of a working electrode including a nanoporous layer, a substrate, and a protective layer according to an embodiment.

Examples 1.1 to 1.3 were repeated, except that 20 nl of the nanoparticle suspension was used, and a biocompatible membrane was deposited on top of the nanoporous layer by spray coating (e.g., 350 times) before the curing step to form a nanoporous layer electrode with a nanoporous layer 117 between the gold-plated conductive layer 110 and the outer membrane 112 as illustrated in FIG. 24. The outer member thickness is dependent on the spray coating repeating times and the concentration of the biocompatible polymer dissolved in isopropyl alcohol and water-tetrahydrofuran mixed solvent.

Example 7.2: Nanoporous Layer Electrode with Outer Membrane No. 9

Example 7.2 was repeated, except that 20 nl of the nanoparticle suspension was used.

54

Example 7.3: Nanoporous Layer Electrode with Outer Membrane No. 10

Example 7.2 was repeated, except that 10 nl of the nanoparticle suspension was used.

Example 8: Glucose Sensitivity in Serum

Example 8.1: Glucose-Sensing System No. 8 in Serum

Human serum was purchased from Sigma-Aldrich. The glucose content in the serum was measured using YSI. It was determined that the serum contained 5.8 mM glucose therein, which corresponds to blood glucose level 104 mg/dl. 10 ml of the serum was placed in a beaker, in which the temperature of the serum was maintained at 37° C. Electrochemical cell No. 8 was prepared as in Example 2.3 except that the nanoporous layer electrode No. 8 prepared in Example 7.1 was used as the working electrode 103 and further except that the working, reference and counter electrodes were submerged into the serum.

Example 8.2: Glucose-Sensing System No. 9 in Serum

Example 8.1 was repeated except that the nanoporous layer electrode No. 9 prepared in Example 7.2 was used as the working electrode 103.

Example 8.3: Glucose-Sensing System No. 10 in Serum

Example 8.1 was repeated except that the nanoporous layer electrode No. 10 prepared in Example 7.3 was used as the working electrode 103.

Example 8.4: Electric Current by Glucose-Sensing System No. 8 in Serum

Example 2.10 was repeated for the glucose-sensing system No. 8 in serum from Example 8.1. The current value was taken for the glucose contained in the serum.

Example 8.5: Electric Current by Glucose-Sensing System No. 8 by Increment of Glucose Concentration in Serum Example 2.12 was repeated except 32 μl of the glucose stock solution prepared in Example 2.1 was added to 6.4 ml of serum to make 5 mM glucose concentration difference. The glucose concentration was increased twice in successive 5 mM increments. When the current became stable, the current value was taken for glucose in the serum whose concentration was higher than that of initial serum by 10 mM.

Example 8.6: Electric Currents by Glucose-Sensing System No. 9

Examples 8.4 to 8.5 were repeated for the glucose-sensing system No. 9.

Example 8.7: Electric Currents by Glucose-Sensing System No. 10

Examples 8.4 to 8.5 were repeated for the glucose-sensing system No. 10.

Example 8.8: Glucose Sensitivity of Glucose-Sensing System No. 8

The change in the electric currents measured in Examples 8.4 to 8.5 is divided by the change in the glucose concentration to obtain the glucose sensitivity of the glucose-sensing system No. 8.

Example 8.9: Glucose Sensitivity of Glucose-Sensing System No. 9

Example 8.8 was repeated for the glucose-sensing system No. 9 to obtain its glucose sensitivity.

Example 8.10: Glucose Sensitivity of Glucose-Sensing System No. 10

Example 8.8 was repeated for the glucose-sensing system No. 10 to obtain its glucose sensitivity. TABLE 6 shows the obtained sensitivity of the three glucose-sensing system Nos. 8 to 10.

TABLE 6

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 8 | −0.87 | 13 | 13.9 | 10 | 1.4 |
| 9 | −1.4 | 11 | 12.4 | 10 | 1.2 |
| 10 | −2.3 | 2.5 | 4.8 | 10 | 0.5 |

$I_1$: Current at initial glucose concentration in serum as supplied
$I_2$: Current when the glucose concentration increased by $\Delta C$ from initial concentration
$\Delta I/\Delta C$: Glucose sensor sensitivity

Example 8.11: Impedance of Glucose-Sensing System No. 8 at 1 Hz

Example 4.1 was repeated for the nanoporous layer electrode No. 8 to find the frequency ranges. The frequency of 1 Hz was selected, and the imaginary impedance absolute value |Z| at 1 Hz was obtained.

Example 8.12: Impedance of Glucose-Sensing System No. 9 at 1 Hz

Example 8.11 was repeated for the nanoporous layer electrode No. 9 to obtain its imaginary impedance absolute value |Z| at 1 Hz.

Example 8.13: Impedance of Glucose-Sensing System No. 10 at 1 Hz

Example 8.11 was repeated for the nanoporous layer electrode No. 10 to obtain its imaginary impedance absolute value |Z| at 1 Hz.

Example 8.14: Plotting Impedance Against Glucose Sensitivity

Figure 25A:
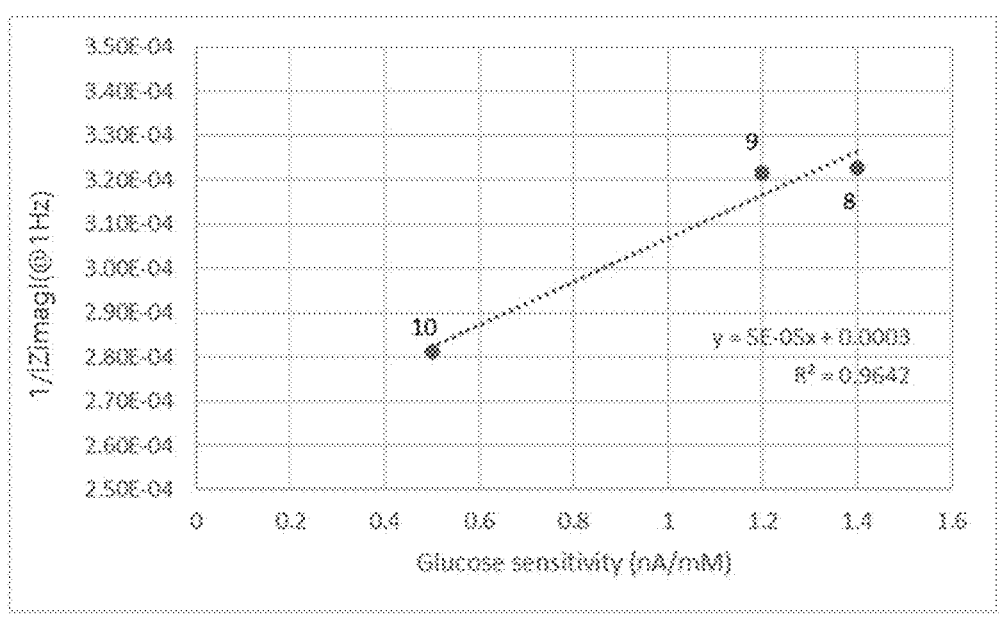
FIG. 25A shows the plots of the inverse of imaginary impedance (1/ZIm) vs. the sensitivity of sensors Nos. 8-10 at 1 Hz and the glucose sensitivities of these sensors.

The values of the inverse of the absolute imaginary impedance, namely the 1/Zim values, of the glucose-sensing systems Nos. 8 to 10 at 1 Hz obtained in Examples 8.11 to 8.13 were plotted against the glucose sensitivities of these sensors obtained in Examples 8.8 to 8.10, as shown in TABLE 7, in FIG. 25A.

Example 8.15: Glucose Sensitivity Error Rate of Nanoporous Layer Electrode No. 8

Examples 6.2 to 6.5 were repeated for the nanoporous layer electrode No. 6 to obtain the error rate of this electrode's sensitivity.

Example 8.16: Glucose Sensitivity Error Rate of Nanoporous Layer Electrode No. 9

Examples 6.2 to 6.5 were repeated for the nanoporous layer electrode No. 9 to obtain the error rate of this electrode's sensitivity.

Example 8.17: Glucose Sensitivity Error Rate of Nanoporous Layer Electrode No. 10

Examples 6.2 to 6.5 were repeated for the nanoporous layer electrode No. 10 to obtain the error rate of this electrode's sensitivity.

The sensitivity error rates of the nanoporous layer electrodes Nos. 8 to 10 at 1 Hz are shown in TABLE 7.

TABLE 7

| Sensor No. | S (nA/mM) | $1/Z_{im}$ at 1 Hz | $S_{cal}$ (nA/mM) | $\Delta S$ | Error Rate (%) |
|---|---|---|---|---|---|
| 8 | 1.4 | $3.23 \times 10^{-4}$ | 1.3 | −0.1 | 13 |
| 9 | 1.2 | $3.22 \times 10^{-4}$ | 1.2 | 0.0 | 9 |
| 10 | 0.5 | $2.81 \times 10^{-4}$ | 0.4 | −0.1 | −20 |

Figure 25B:
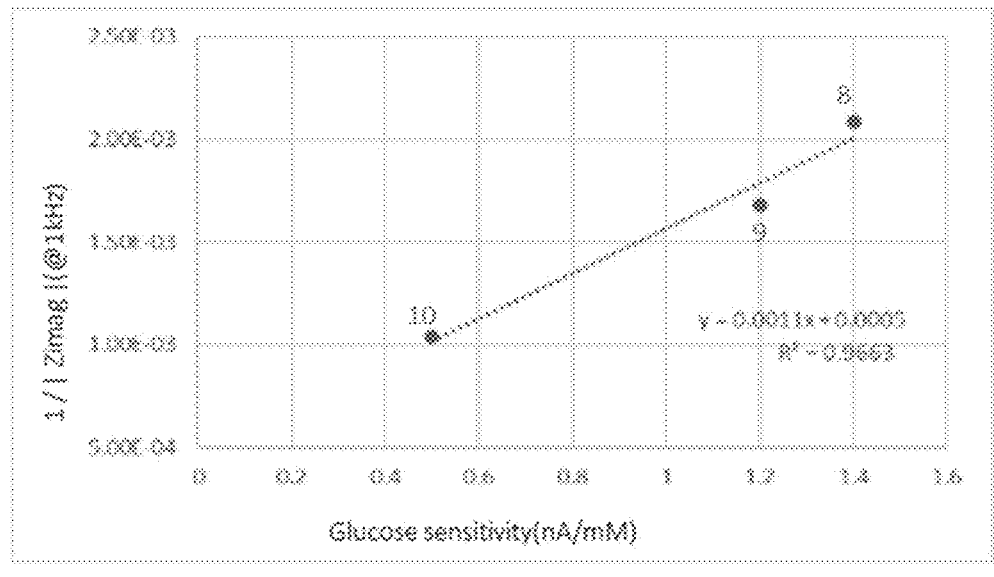
FIG. 25B shows the plots of the inverse of imaginary impedance (1/ZIm) vs. the sensitivity of sensors Nos. 8-10 at 1 KHz and the glucose sensitivities of these sensors.

Example 8.18: Sensitivity Error Rates of Nanoporous Layer Electrodes Nos. 8 to 10 at 1 khz Examples 8.11 to 8.17 were repeated to obtain the sensitivity error rates of the nanoporous layer electrodes Nos. 8 to 10 at 1 kHz, as shown in TABLE 8. The plot of 1/|Zimag| at 1 kHz against the glucose sensitivity is shown in FIG. 25B.

TABLE 8

| Sensor No. | S (nA/mM) | $1/Z_{im}$ at 1 kHz | $S_{cal}$ (nA/mM) | $\Delta S$ | Error Rate (%) |
|---|---|---|---|---|---|
| 8 | 1.4 | $2.09 \times 10^{-3}$ | 1.4 | 0.0 | 0.0 |
| 9 | 1.2 | $1.68 \times 10^{-3}$ | 1.1 | −0.1 | 8.3 |
| 10 | 0.5 | $1.04 \times 10^{-3}$ | 0.5 | 0.0 | 0.0 |

Figure 26A:
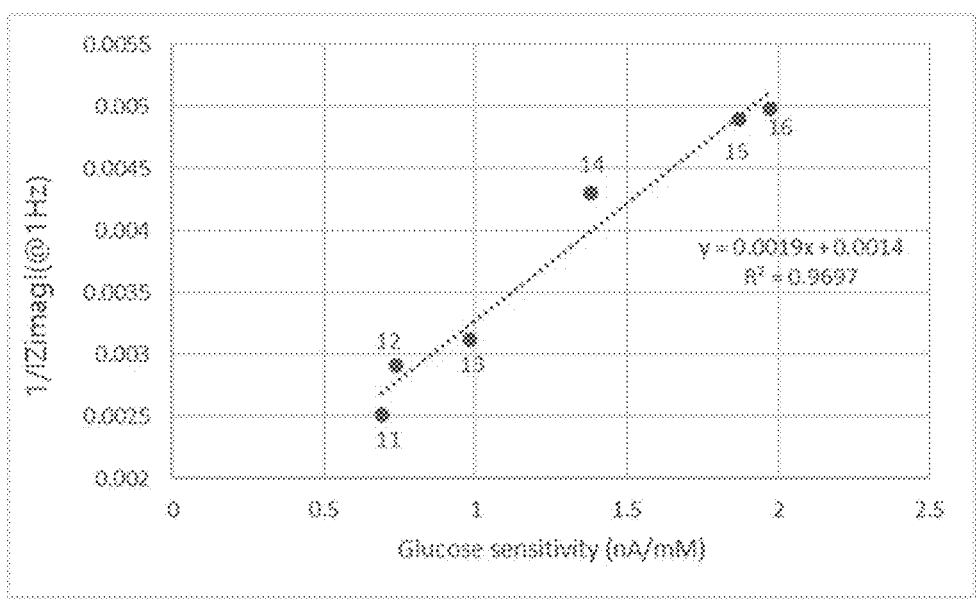
FIG. 26A shows the plots of the inverse of imaginary impedance (1/ZIm) vs. the sensitivity of sensors Nos. 11-16 at 1 Hz and the glucose sensitivities of these sensors.
Figure 26B:
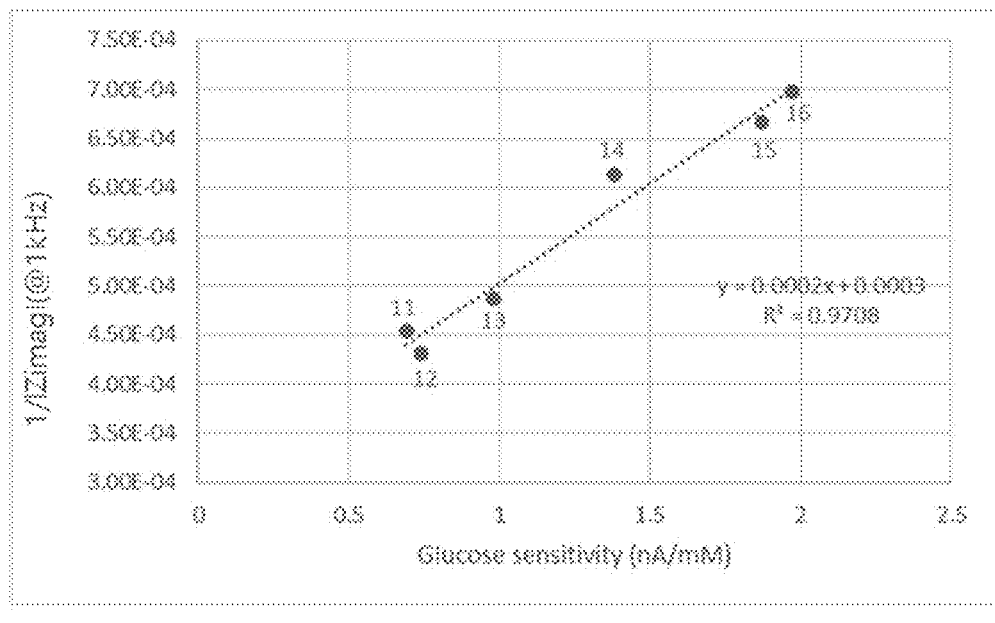
FIG. 26B shows the plots of the inverse of imaginary impedance (1/ZIm) vs. the sensitivity of sensors Nos. 11-16 at 1 KHz and the glucose sensitivities of these sensors.

Example 8.19: Glucose Sensitivities of Nanoporous Layer Electrodes No. 11 to 16 in Serum Examples 7.1, 8.1, 8.5, 8.8, 8.11, 8.14, 8.15, and 8.19 were repeated, except for the outer membrane thickness made by adjusting the number of spray coatings, as shown in TABLE 9, to prepare the nanoporous layer electrodes Nos. 11 to 16 and obtain their glucose sensitivities and error rates, at 1 kHz and 1 Hz, respectively, as shown in TABLES 10 and 11 and FIGS. 26A and 26B.

TABLE 9

| Nanoporous Layer Electrode No. | Volume of nanoparticle suspension | Outer Membrane Thickness (μm) | Number of Spray Coatings |
|---|---|---|---|
| 11 | 20 nl | ~15 um | 300 |
| 12 | 20 nl | ~15 um | 300 |
| 13 | 20 nl | ~15 um | 300 |
| 14 | 30 nl | ~15 um | 300 |
| 15 | 30 nl | ~15 um | 300 |
| 16 | 30 nl | ~15 um | 300 |

TABLE 10

| Sensor No. | S (nA/mM) | $1/Z_{im}$ at 1 kHz | $S_{cal}$ (nA/mM) | ΔS | Error Rate (%) |
|---|---|---|---|---|---|
| 11 | 0.7 | $2.51 \times 10^{-3}$ | 0.6 | −0.1 | 15.3 |
| 12 | 0.7 | $2.91 \times 10^{-3}$ | 0.8 | 0.1 | 7.4 |
| 13 | 1.0 | $3.11 \times 10^{-3}$ | 0.9 | −0.1 | 8.2 |
| 14 | 1.4 | $4.30 \times 10^{-3}$ | 1.5 | 0.1 | 10.6 |
| 15 | 1.9 | $4.90 \times 10^{-3}$ | 1.8 | 0.0 | 1.5 |
| 16 | 2.0 | $4.98 \times 10^{-3}$ | 1.9 | −0.1 | 4.4 |

TABLE 11

| Sensor No. | S (nA/mM) | $1/Z_{im}$ at 1 Hz | $S_{cal}$ (nA/mM) | ΔS | Error Rate (%) |
|---|---|---|---|---|---|
| 11 | 0.7 | $4.54 \times 10^{-4}$ | 0.8 | 0.1 | 11.4 |
| 12 | 0.7 | $4.31 \times 10^{-4}$ | 0.7 | −0.1 | 11.3 |
| 13 | 1.0 | $4.88 \times 10^{-4}$ | 0.9 | 0.0 | 4.3 |
| 14 | 1.4 | $6.13 \times 10^{-4}$ | 1.6 | 0.2 | 13.3 |
| 15 | 1.9 | $6.66 \times 10^{-4}$ | 1.8 | 0.0 | 2.1 |
| 16 | 2.0 | $6.97 \times 10^{-4}$ | 2.0 | 0.0 | 0.9 |

Figure 27A:
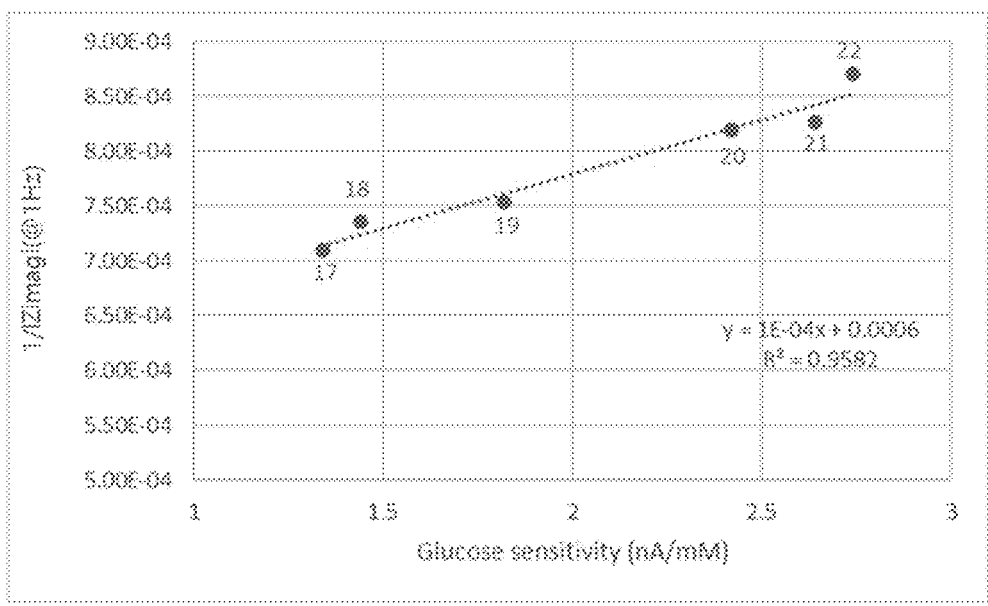
FIG. 27A shows the plots of the inverse of imaginary impedance (1/ZIm) vs. the sensitivity of sensors Nos. 17-22 at 1 Hz and the glucose sensitivities of these sensors.
Figure 27B:
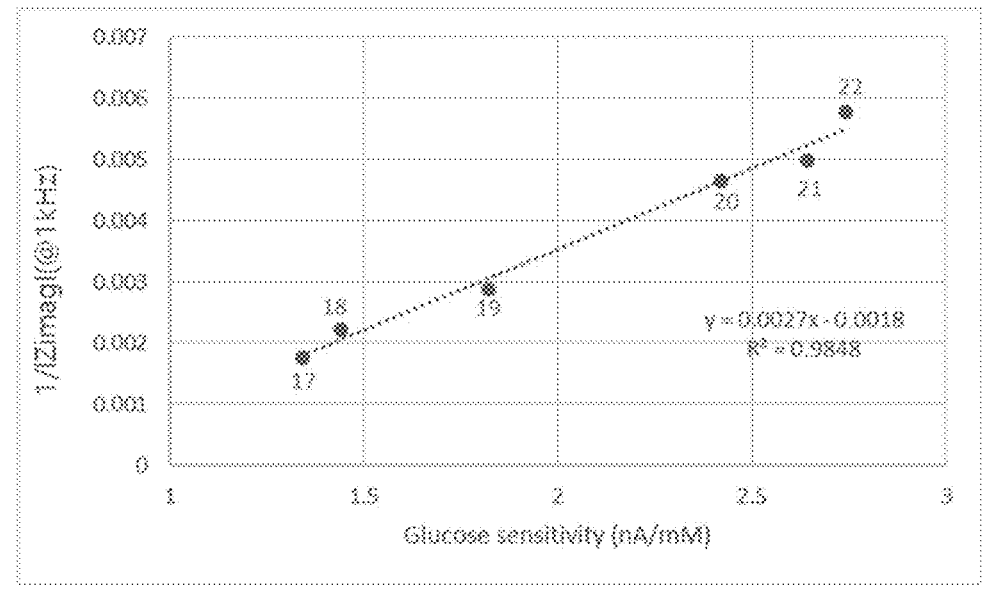
FIG. 27B shows the plots of the inverse of imaginary impedance (1/ZIm) vs. the sensitivity of sensors Nos. 17-22 at 1 KHz and the glucose sensitivities of these sensors.

Example 8.20: Glucose Sensitivities of Nanoporous Layer Electrodes No. 17 to 22 in Serum Examples 7.1, 8.1, 8.5, 8.8, 8.11, 8.14, 8.15, and 8.19 were repeated, except for the outer membrane thickness (made by adjusting the number of spray coatings, as shown in TABLE 12, to prepare the nanoporous layer electrodes Nos. 17 to 22 and obtain their glucose sensitivities and error rates, at 1 KHz and 1 Hz, respectively, as shown in TABLES 13 and 14 and FIGS. 27A and 27B.

TABLE 12

| Nanoporous Layer Electrode No. | Volume of nanoparticle suspension | Outer Membrane Thickness (μm) | Number of Spray Coatings |
|---|---|---|---|
| 17 | 30 nl | ~10 | 200 |
| 18 | 30 nl | ~10 | 200 |
| 19 | 30 nl | ~10 | 200 |
| 20 | 40 nl | ~10 | 200 |
| 21 | 40 nl | ~10 | 200 |
| 22 | 40 nl | ~10 | 200 |

TABLE 13

| Sensor No. | S (nA/mM) | $1/Z_{im}$ at 1 kHz | $S_{cal}$ (nA/mM) | ΔS | Error Rate (%) |
|---|---|---|---|---|---|
| 17 | 1.3 | $1.75 \times 10^{-3}$ | 1.2 | −0.1 | 9.6 |
| 18 | 1.4 | $2.22 \times 10^{-3}$ | 1.4 | 0.0 | 3.3 |
| 19 | 1.8 | $2.88 \times 10^{-3}$ | 1.6 | −0.2 | 9.6 |
| 20 | 2.4 | $4.65 \times 10^{-3}$ | 2.3 | −0.1 | 3.8 |

TABLE 13-continued

| Sensor No. | S (nA/mM) | $1/Z_{im}$ at 1 kHz | $S_{cal}$ (nA/mM) | ΔS | Error Rate (%) |
|---|---|---|---|---|---|
| 21 | 2.6 | $4.98 \times 10^{-3}$ | 2.5 | −0.2 | 7.1 |
| 22 | 2.7 | $5.78 \times 10^{-3}$ | 2.8 | 0.0 | 0.8 |

TABLE 14

| Sensor No. | S (nA/mM) | $1/Z_{im}$ at 1 Hz | $S_{cal}$ (nA/mM) | ΔS | Error Rate (%) |
|---|---|---|---|---|---|
| 17 | 1.3 | $7.10 \times 10^{-4}$ | 1.1 | −0.2 | 17.7 |
| 18 | 1.4 | $7.36 \times 10^{-4}$ | 1.4 | −0.1 | 5.3 |
| 19 | 1.8 | $7.54 \times 10^{-4}$ | 1.5 | −0.3 | 15.4 |
| 20 | 2.4 | $8.20 \times 10^{-4}$ | 2.2 | −0.2 | 9.2 |
| 21 | 2.6 | $8.27 \times 10^{-4}$ | 2.3 | −0.4 | 14.2 |
| 22 | 2.7 | $8.70 \times 10^{-4}$ | 2.7 | 0.0 | 1.3 |

The Mean Absolute Relative Difference (MARD) of FDA-approved continuous glucose monitoring systems (CGMS) products is around 10%, which is the average MARD value of all CGMS products used in clinical trials. The error rate of the samples used in the examples herein may be caused by deviation that occurs in the preparation of the samples, such as the uniformity of the material dispersion and the defect space of the nanoporous layers (gap between the nanoporous layers), among other, and can be sufficiently improved through process improvement.

Example 9: Cleaning of Nanoporous Layer Sensor

Example 9.1: Nanoporous Layer Sensor No. 23

Example 7.1 was repeated except that 20 nl of the nanoparticle suspension was used to prepare the nanoporous layer electrode No. 23.

Example 9.2: Contamination of Nanoporous Layer Sensor No. 23

Electrochemical cell No. 23 was prepared as in Example 8.1 except that the nanoporous layer electrode No. 23 prepared in Example 9.1 was used as the working electrode 103 and further except that the working, reference and counter electrode (that is, sensor) were submerged in the subcutaneous tissue of rat for 7 days.

Example 9.3: Pre-cleaning Glucose Sensitivity of Nanoporous Layer Sensor No. 23

Figure 28:
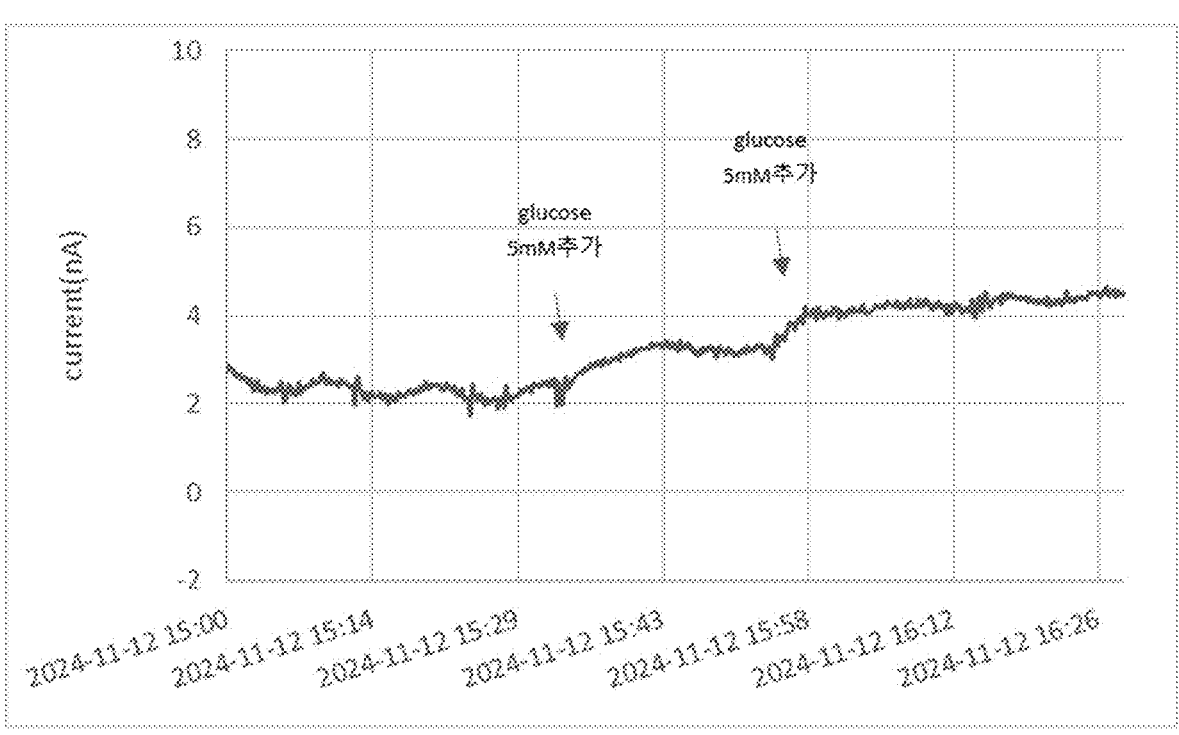
FIG. 28 is a graph of the current of Sensor No. 23 measured in the serum after the sensor was inserted into rat and retrieved.

The nanoporous layer sensor No. 23 was removed from the subcutaneous tissue of rat and submerged in serum. Examples 8.4 to 8.5 were then repeated. The glucose concentration in the serum was 5 mM initially and then increased twice in successive 5 mM increments to 15 mM, respectively. The electric currents were obtained, as shown in FIG. 28, and the glucose sensitivity was obtained by dividing the change in currents by the difference in the glucose concentrations, as shown in TABLE 15.

TABLE 15

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 23 | 2.41 | 4.39 | 1.98 | 10 | 0.20 |

Example 9.4: Cleaning 1 of Nanoporous Layer
Sensor No. 23

Figure 29A:
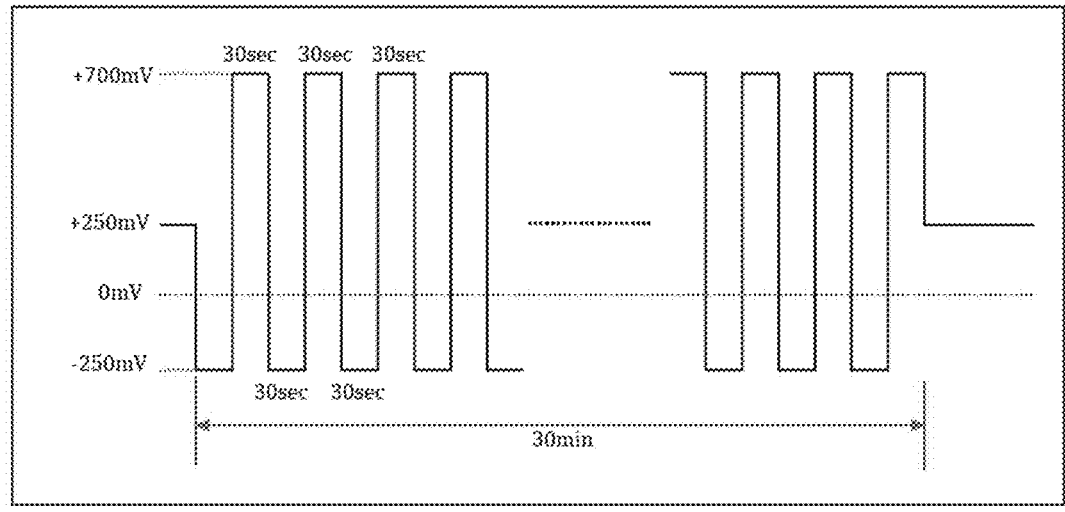
FIG. 29A shows the waveform of the pulse voltage used in Example 9.4.

The nanoporous layer sensor No. 23 was taken out of the serum with 15 mM glucose after measuring the pre-cleaning glucose sensitivity and submerged in fresh serum. A cleaning voltage was applied for 30 minutes. The cleaning voltage has a waveform as shown in FIG. 29A.

Example 9.5: Post-cleaning Glucose Sensitivity of
Nanoporous Layer Sensor No. 23

Figure 29B:
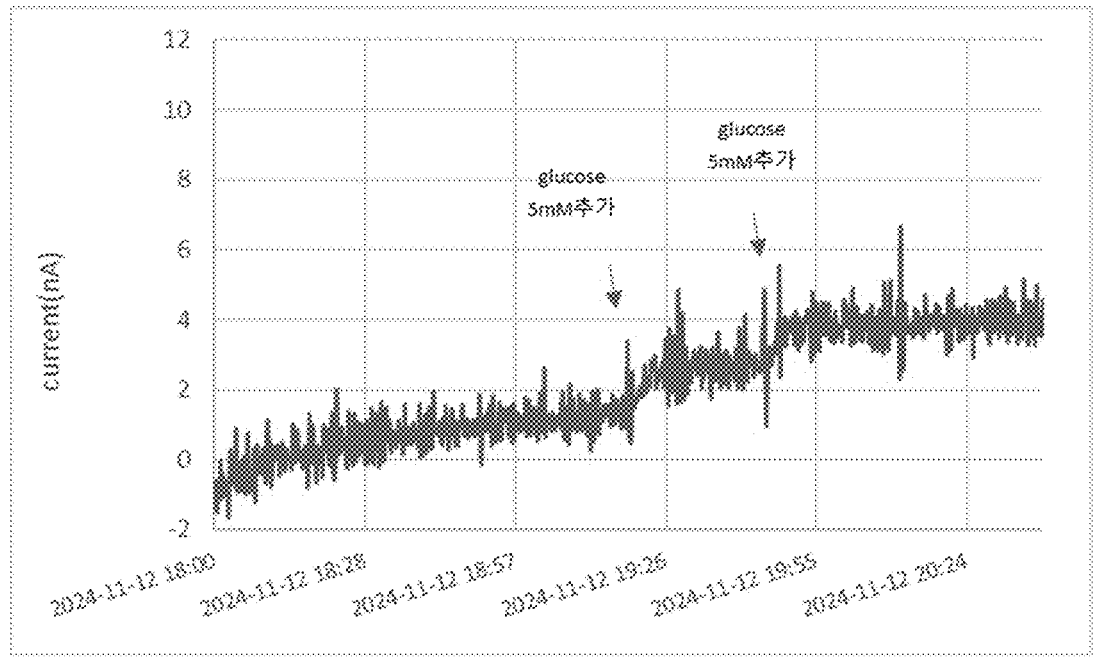
FIG. 29B is a graph of the current of Sensor No. 23 measured in the serum after cleaning 1.

Example 9.3 was repeated. The electric currents were obtained, as shown in FIG. 29B, and the glucose sensitivity was obtained by dividing the change in currents by the difference in the glucose concentrations, as shown in TABLE 16.

TABLE 16

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 23 | 1.37 | 3.99 | 2.62 | 10 | 0.26 |

$I_1$: Current at initial glucose concentration in serum as supplied
$I_2$: Current when the glucose concentration increased by AC from initial concentration
$\Delta I/\Delta C$: Glucose sensor sensitivity Example 9.6: Cleaning 2 of Nanoporous Layer
Sensor No. 23

Figure 30A:
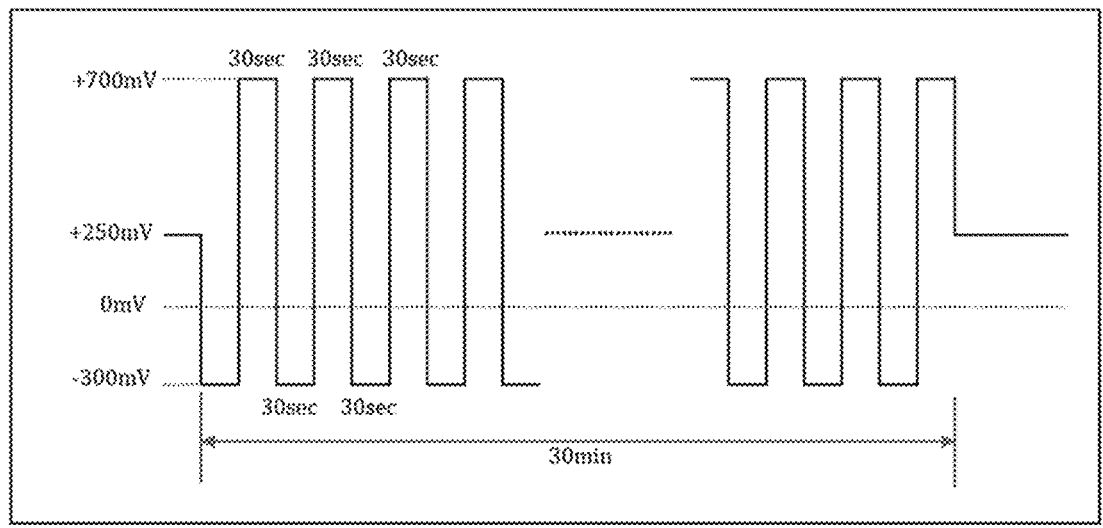
FIG. 30A shows the waveform of the pulse voltage used in Example 9.6.
Figure 30B:
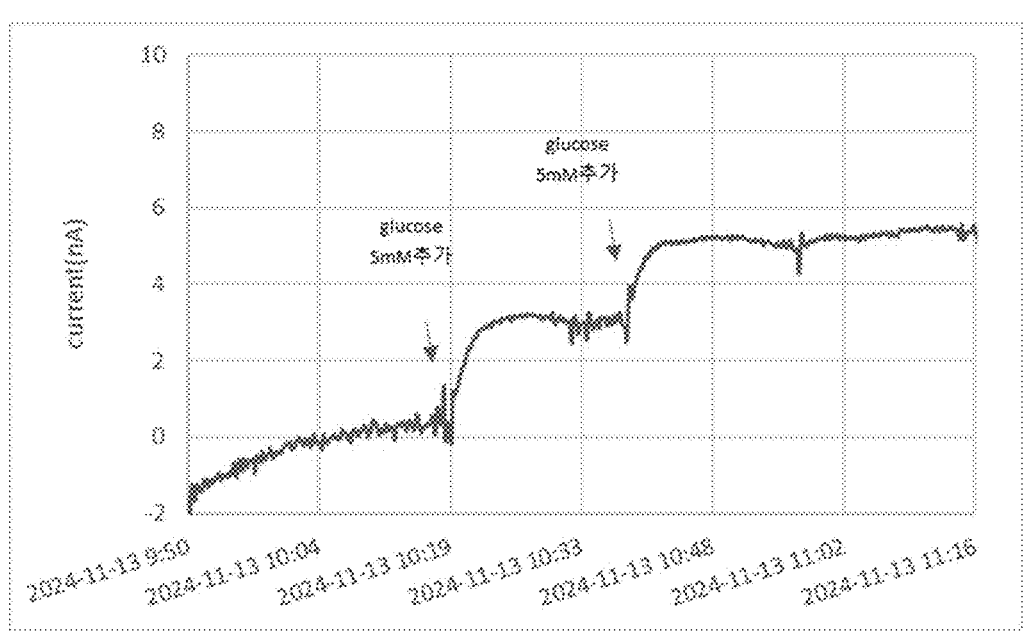
FIG. 30B is a graph of the current of Sensor No. 23 measured in the serum after the sensor was inserted into rat and retrieved, and then the sensor underwent cleaning 2.

Nanoporous layer sensor No. 23 was submerged again in the subcutaneous tissue of rat for 7 days. Then, Examples 9.4 to 9.5 were repeated, except a pulse voltage having a waveform shown in FIG. 30A was applied for 30 minutes. The current values were taken, as shown in FIG. 30B. The glucose sensitivity was obtained as shown in TABLE 17.

TABLE 17

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 23 | 0.79 | 5.10 | 4.31 | 10 | 0.43 |

$I_1$: Current at initial glucose concentration in serum as supplied
$I_2$: Current when the glucose concentration increased by AC from initial concentration
$\Delta I/\Delta C$: Glucose sensor sensitivity Example 9.7: Post-Cleaning Glucose Sensitivity of
Nanoporous Layer Sensor No. 24

Figure 31A:
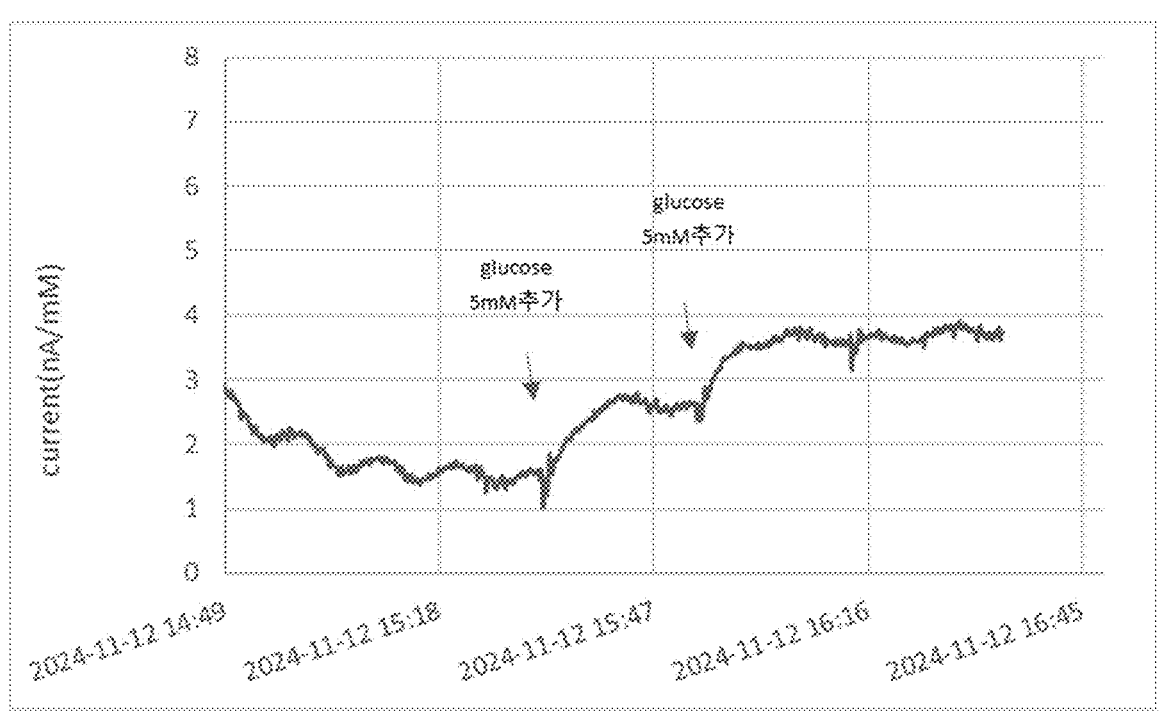
FIG. 31A is a graph of the current of Sensor No. 24 measured in the serum after the sensor was inserted into rat and retrieved.
Figure 31B:
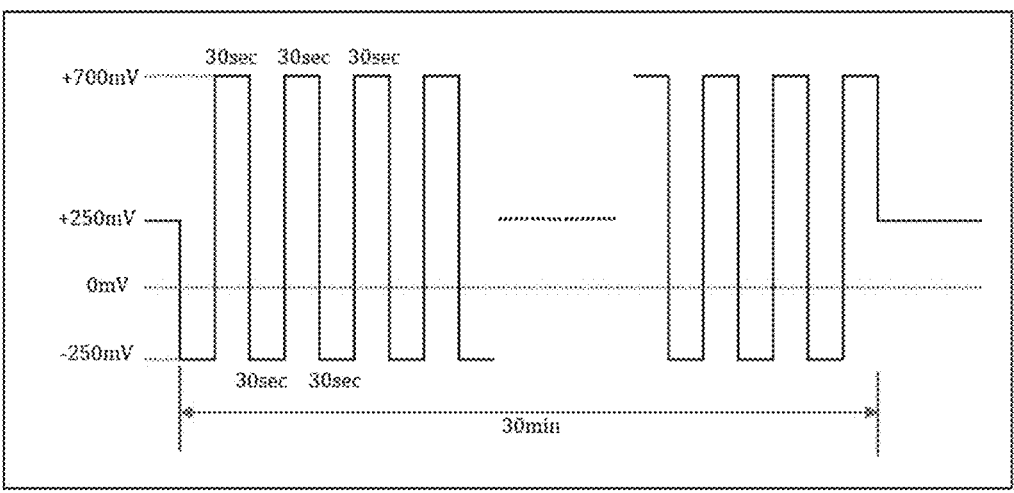
FIG. 31B shows the waveform of the pulse voltage used in Example 9.7.
Figure 31C:
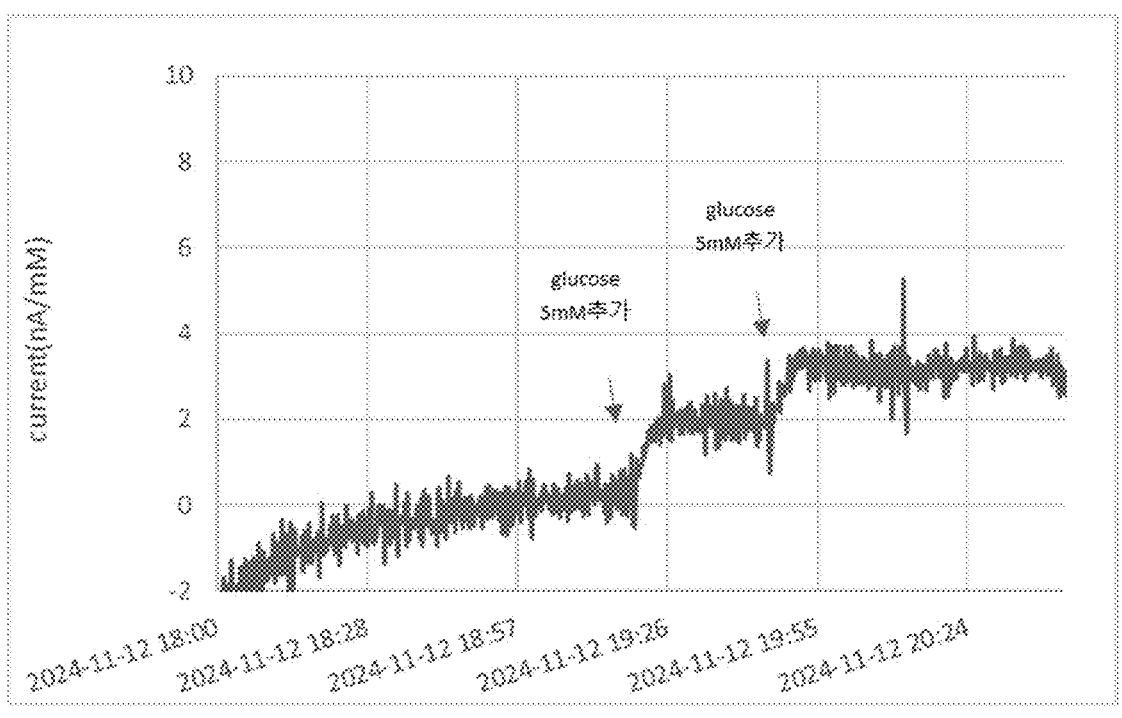
FIG. 31C is a graph of the current of Sensor No. 24 measured in the serum after cleaning 1.
Figure 31D:
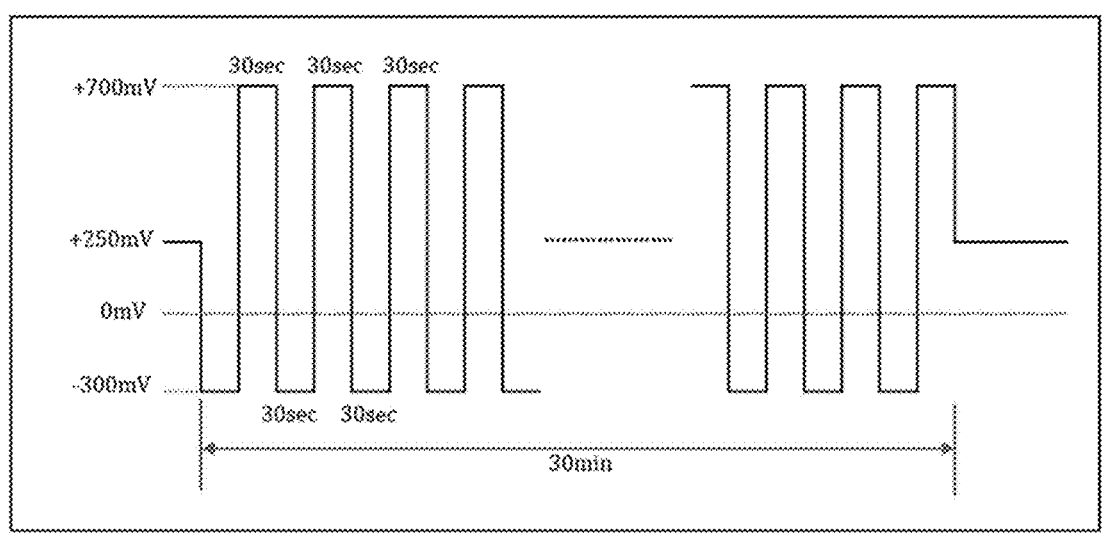
FIG. 31D shows the waveform of the pulse voltage used in Cleaning 2 in Example 9.7.
Figure 31E:
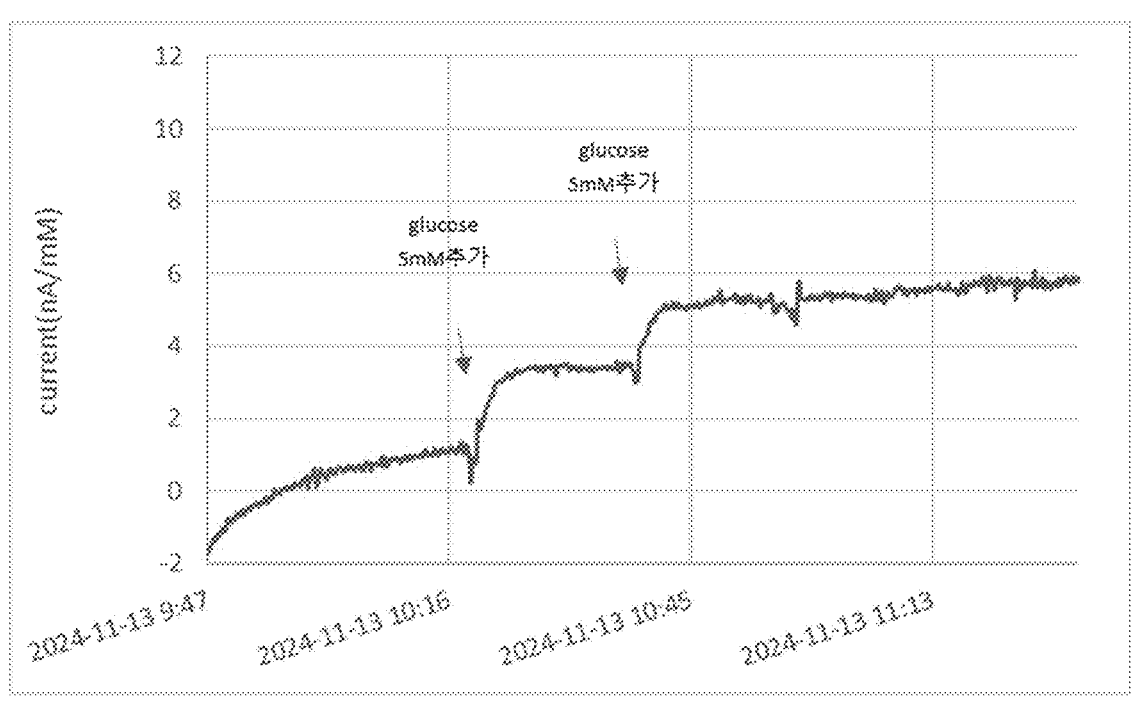
FIG. 31E is a graph of the current of Sensor No. 24 measured in the serum after the sensor was inserted into rat and retrieved, and then the sensor underwent cleaning 2.

Examples 9.1 to 9.6 were repeated, except that 20 nl of the nanoparticle suspension was used to prepare the nanoporous layer sensor No. 24, a pulse voltage with a waveform as shown in FIG. 31B was applied for 30 minutes in Cleaning 1, and a pulse voltage with a waveform as shown in FIG. 31D was applied for 30 minutes in Cleaning 2. The plots of currents against time were shown in FIGS. 31A (pre-cleaning), 31C (post-Cleaning 1), and 31E (post-Cleaning 2), respectively; and the glucose sensitivities were obtained as shown in TABLES 18 (pre-cleaning), 19 (post-Cleaning 1), and 20 (post-Cleaning 2), respectively.

TABLE 18

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 24 | 1.59 | 3.57 | 1.98 | 10 | 0.20 |

TABLE 19

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 24 | 0.42 | 3.54 | 3.12 | 10 | 0.31 |

TABLE 20

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 24 | 1.01 | 5.32 | 4.31 | 10 | 0.43 |

$I_1$: Current at initial glucose concentration in serum as supplied
$I_2$: Current when the glucose concentration increased by AC from initial concentration
$\Delta V/\Delta C$: Glucose sensor sensitivity Example 10: Cleaning Duration Example 10.1: Nanoporous Layer Sensor (with
Outer Membrane) No. 25

Example 7.1 was repeated except that 20 nl of the nanoparticle suspension was used to prepare the nanoporous layer sensor No. 25.

Example 10.2: Contamination of Nanoporous Layer
Sensor No. 25

Example 9.2 was repeated for the nanoporous layer sensor No. 25

Example 10.3: Pre-cleaning Glucose Sensitivity of
Nanoporous Layer Sensor No. 25

Figure 32A:
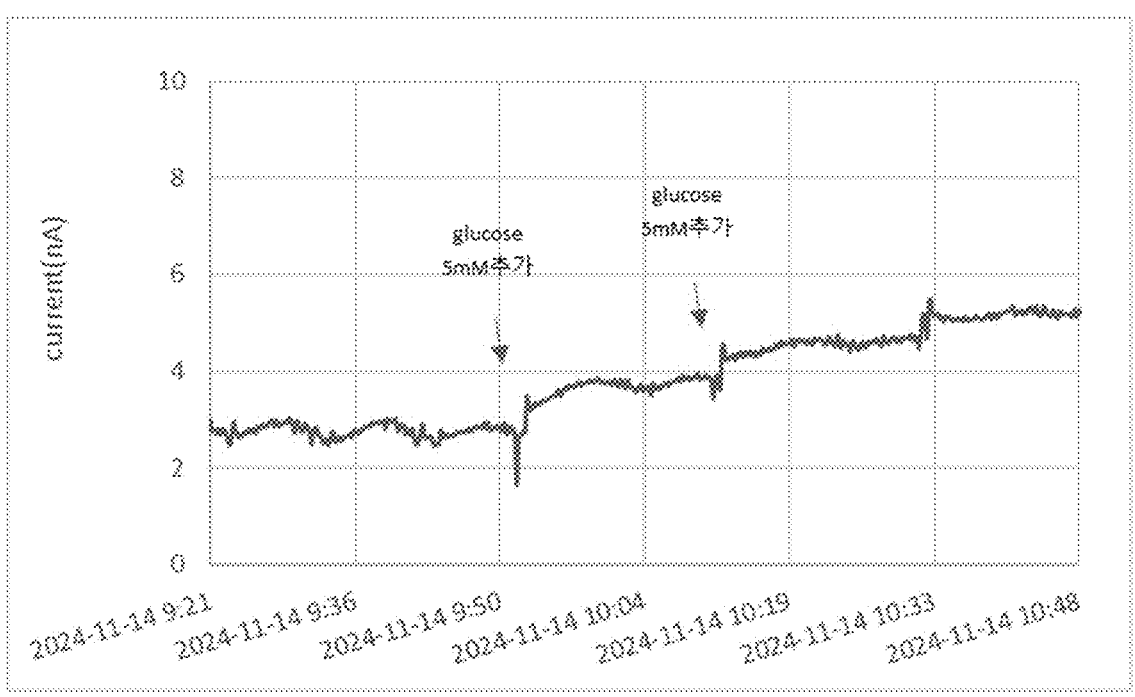
FIG. 32A is a graph of the current of Sensor No. 25 measured in the serum after the sensor was inserted into rat and retrieved.

Example 9.3 was repeated for the nanoporous layer sensor No. 25. The electric currents were obtained, as shown in FIG. 32A, and the pre-cleaning glucose sensitivity was obtained as shown in TABLE 21.

TABLE 21

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 25 | 2.94 | 4.57 | 1.63 | 10 | 0.16 |

$I_1$: Current at initial glucose concentration in serum as supplied $I_2$: Current when the glucose concentration increased by AC from initial concentration $\Delta I/\Delta C$: Glucose sensor sensitivity

Example 10.4: Post-cleaning 1 Glucose Sensitivity of Nanoporous Layer Sensor No. 25

Figure 32B:
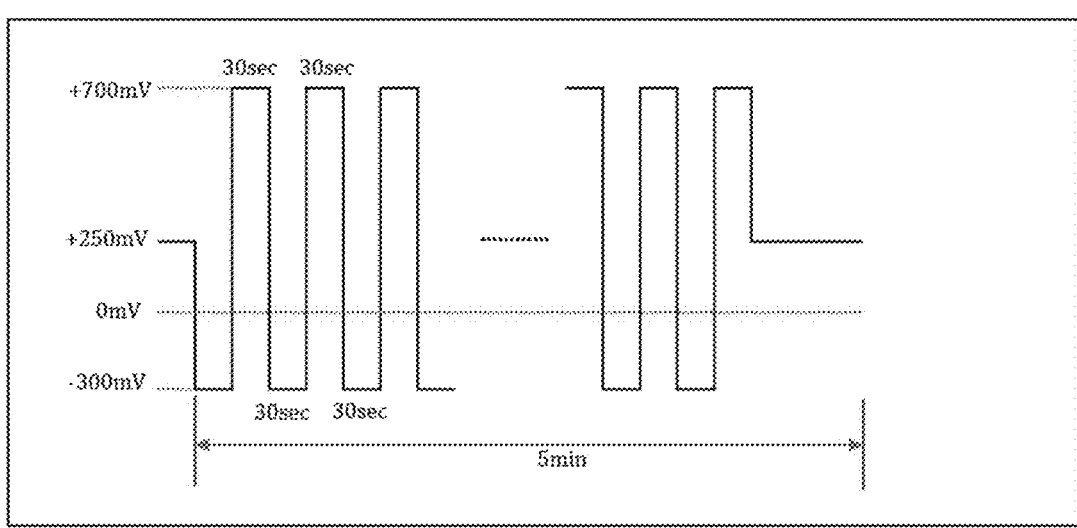
FIG. 32B shows the waveform of the pulse voltage used in Example 10.4.
Figure 32C:
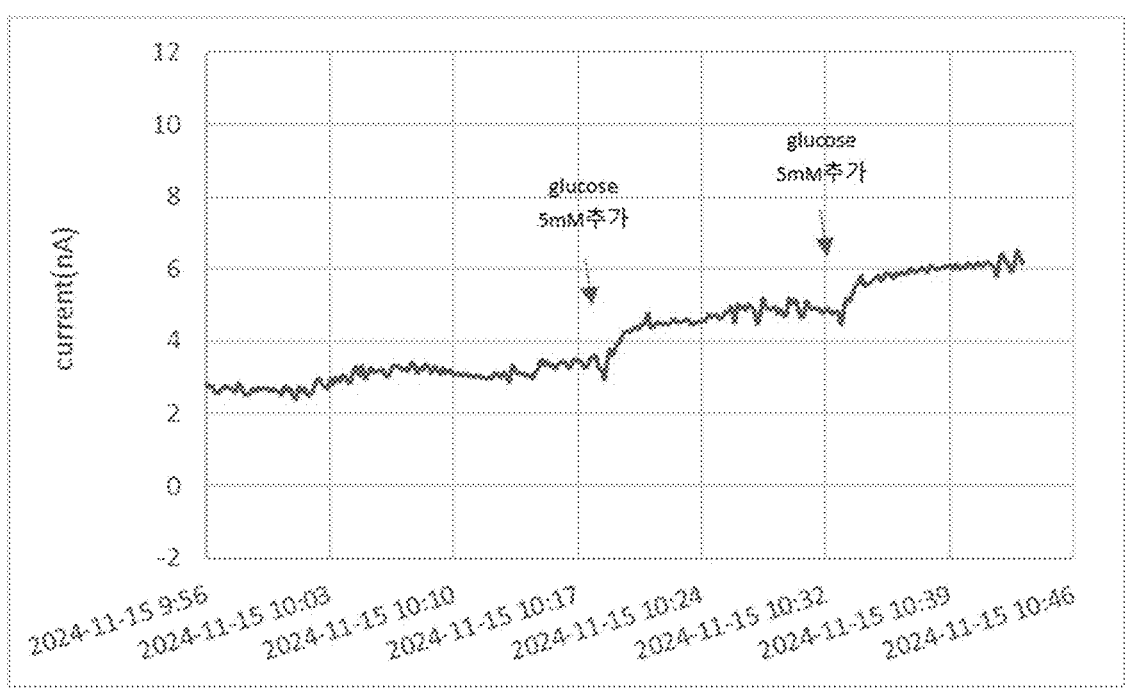
FIG. 32C is a graph of the current of Sensor No. 25 measured in the serum after cleaning 1 for 5 minutes.

Examples 9.4 to 9.5 were repeated, except a pulse voltage having a waveform shown in FIG. 32B was applied for 5 minutes. The current values were taken as shown in FIG. 32C. The glucose sensitivity was obtained as shown in TABLE 22.

TABLE 22

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 25 | 3.46 | 6.26 | 2.8 | 10 | 0.28 |

$I_1$: Current at initial glucose concentration in serum as supplied $I_2$: Current when the glucose concentration increased by AC from initial concentration $\Delta V/\Delta C$: Glucose sensor sensitivity

Example 10.5: Post-Cleaning 2 Glucose Sensitivity of Nanoporous Layer Sensor No. 25

Figure 32D:
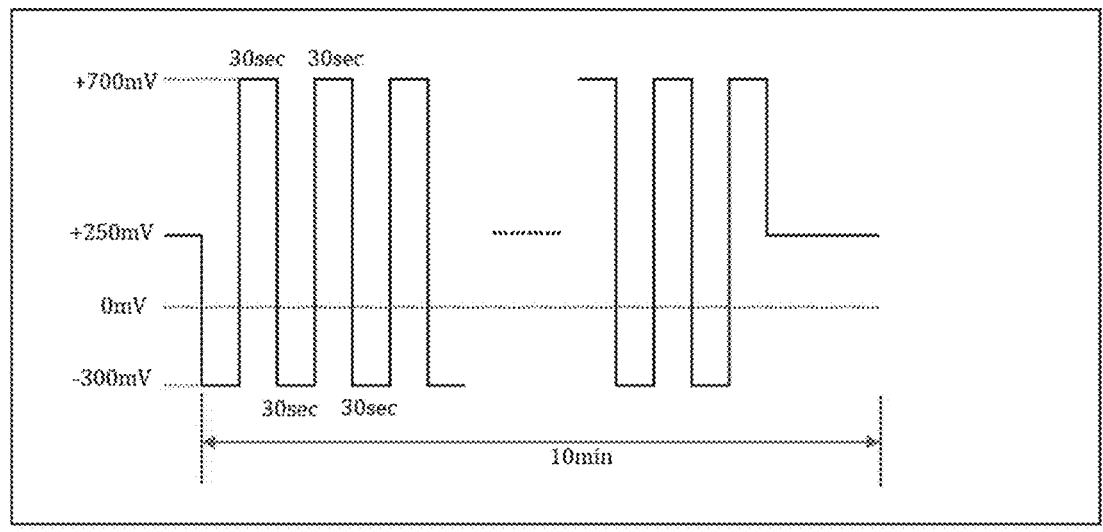
FIG. 32D shows the waveform of the pulse voltage used in Example 10.5.
Figure 32E:
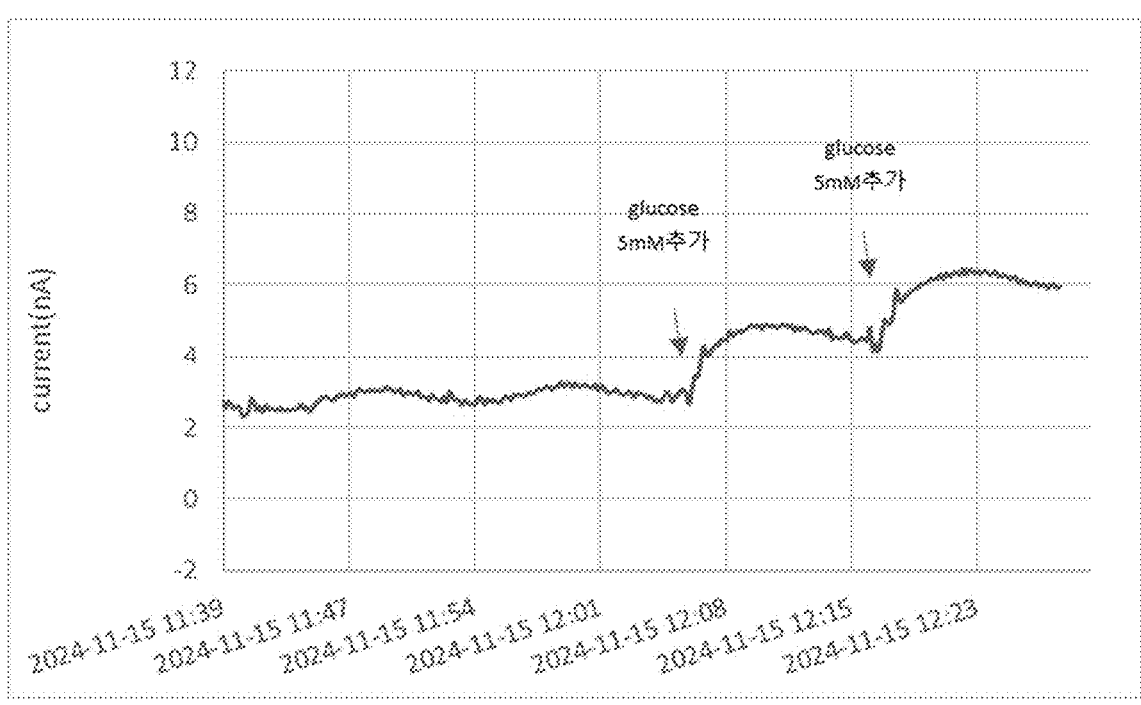
FIG. 32E is a graph of the current of Sensor No. 25 measured in the serum after cleaning 1 for 10 minutes.

Example 10.4 was repeated, except that the pulse voltage was applied for 10 minutes, as shown in FIG. 32D. The current values were taken as shown in FIG. 32E. The glucose sensitivity was obtained as shown in TABLE 23.

TABLE 23

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 25 | 2.83 | 6.04 | 3.23 | 10 | 0.32 |

$I_1$: Current at initial glucose concentration in serum as supplied $I_2$: Current when the glucose concentration increased by AC from initial concentration $\Delta I/\Delta C$: Glucose sensor sensitivity

Example 10.6: Post-cleaning 3 Glucose Sensitivity of Nanoporous Layer Sensor No. 25

Figure 32F:
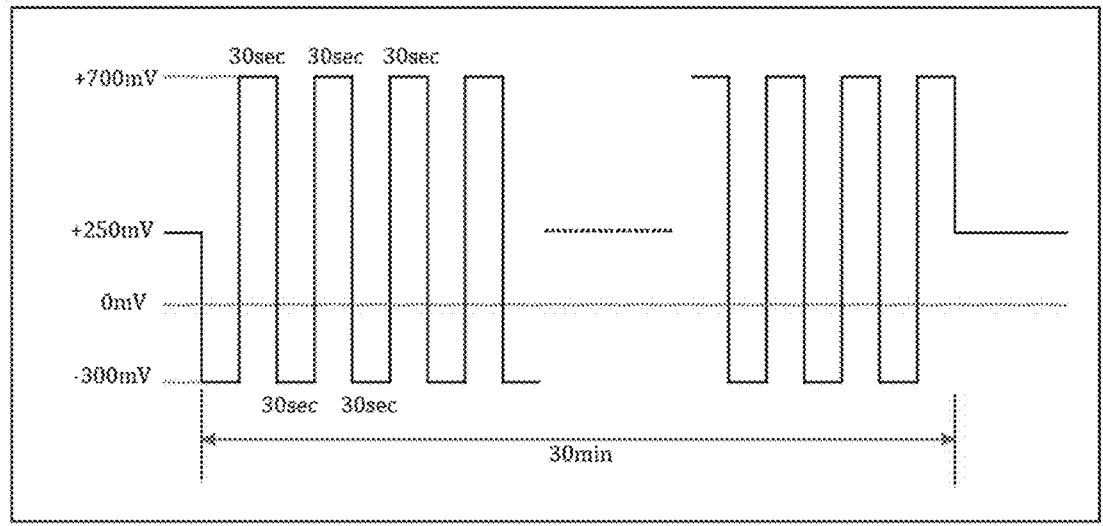
FIG. 32F shows the waveform of the pulse voltage used in Example 10.6.
Figure 32G:
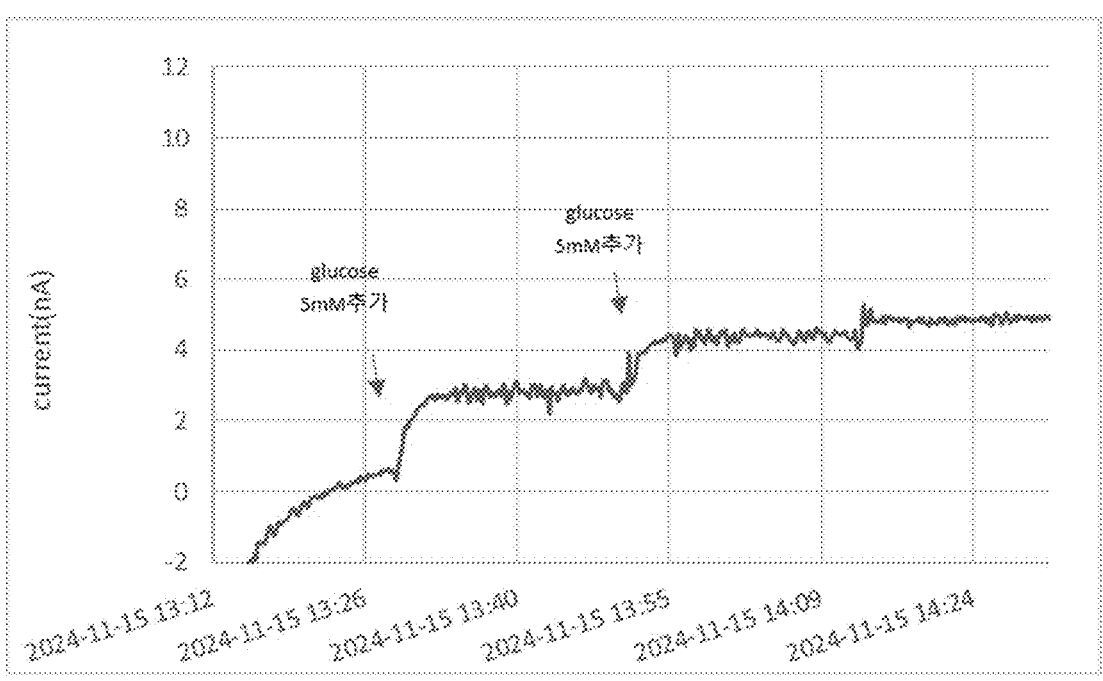
FIG. 32G is a graph of the current of Sensor No. 25 measured in the serum after cleaning 1 for 30 minutes.

Example 10.4 was repeated, except that the pulse voltage was applied for 30 minutes, as shown in FIG. 32F. The current values were taken as shown in FIG. 32G. The glucose sensitivity was obtained as shown in TABLE 24.

TABLE 24

| Sensor No. | $I_1$ (nA) | $I_2$ (nA) | $\Delta I = I_2 - I_1$ (nA) | $\Delta C$ (mM) | $\Delta I/\Delta C$ (nA/mM) |
|---|---|---|---|---|---|
| 25 | 0.65 | 4.47 | 3.82 | 10 | 0.38 |

$I_1$: Current at initial glucose concentration in serum as supplied $I_2$: Current when the glucose concentration increased by AC from initial concentration $\Delta I/\Delta C$: Glucose sensor sensitivity Combinations and Characteristics Included Various features and characteristics are described in this specification to provide an understanding of the composition, structure, production, function, and/or operation of the present disclosure, which includes the disclosed compositions, coatings, and methods. It is understood that the various features and characteristics of the present disclosure described in this specification can be combined in any suitable manner, regardless of whether such features and characteristics are expressly described in combination in this specification. The Inventors and the Applicant expressly intend such combinations of features and characteristics to be included within the scope of the present disclosure described in this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims and will comply with the written description, sufficiency of description, and added matter requirements.

Illustration of Various Aspects

While the present disclosure provides descriptions of various specific aspects for the purpose of illustrating various aspects of the present disclosure and/or its potential applications, it is understood that variations and modifications will occur to those skilled in the art. Accordingly, the present disclosure herein should be understood to be at least as broad as claimed and not as more narrowly defined by particular illustrative aspects provided herein.

The invention claimed is:

1. A method comprising:

providing a continuous glucose monitor (CGM) device comprising:

electrodes comprising a first electrode and a second electrode, wherein the first electrode comprises a nanoporous layer comprising metal nanoparticles;

at least one battery;

at least one wireless communication circuit configured for wirelessly sending data to an external device; and circuitry comprising at least one DC voltage circuit, at least one non-DC voltage input circuit, and an electrochemical impedance spectrometry (EIS) circuit configured to perform electrochemical impedance spectrometry, causing to insert at least part of the CGM device into a subject's body such that the first electrode and the second electrode are in contact with interstitial fluid of the subject, maintaining the at least part of the CGM device in the subject's body over time during which glucose sensitivity of the nanoporous layer for glucose sensitivity changes; and determining the glucose sensitivity of the nanoporous layer while the first electrode and the second electrode are in contact with interstitial fluid of the subject.

2. The method of claim 1, wherein the at least one DC voltage circuit is configured to apply a DC voltage input between the first electrode and second electrode, wherein the at least one non-DC voltage circuit is configured to apply at least one non-DC voltage input between the first electrode and second electrode, wherein the CGM device is configured to be inserted into a subject's body such that the first electrode and the second electrode are in contact with interstitial fluid of the subject, wherein in response to the at least one non-DC voltage input, the EIS circuit is configured to generate a signal indicative of an electrochemically active surface area of the metal nanoparticles in the nanoporous layer.

3. The method of claim 2, wherein the at least one non-DC voltage circuit comprises:

a first non-DC voltage circuit configured to apply a first non-DC voltage input between the first electrode and second electrode; and a second non-DC voltage circuit configured to apply a second non-DC voltage input that differs from the first non-DC voltage in terms of both amplitude and waveform.

4. The method of claim 2, wherein the at least one non-DC voltage circuit comprises:

an AC voltage circuit configured to apply an AC voltage input between the first electrode and second electrode; and a pulse voltage circuit configured to generate at least one pulse voltage input between the first electrode and second electrode.

5. The method of claim 2, wherein the at least one non-DC voltage circuit comprises an AC voltage circuit configured to apply an AC voltage input between the first electrode and second electrode, wherein the EIS circuit is configured to determine an impedance of the nanoporous layer in response to the AC voltage applied between the first electrode and second electrode.

6. The method of claim 2, wherein the at least one non-DC voltage circuit comprises an AC voltage circuit configured to apply an AC voltage input between the first electrode and second electrode.

7. The method of claim 2, further comprising at least one wireless charging circuit configured to wirelessly receive power for charging the at least one battery, wherein the CGM device further comprises a housing in a single body implantable in its entirety into the subject's body, wherein the housing houses the electrodes and allows interstitial fluid to enter the housing to contact the electrodes, wherein the housing further houses the at least one battery, the circuitry, and the at least one wireless communication circuit, and wherein no portion of the single body stays outside the subject's body.

8. The method of claim 7, wherein the housing comprises a liquid-tight compartment configured to inhibit the interstitial fluid from flowing thereinto and a liquid-contacting compartment configured to let the interstitial fluid flow thereinto, wherein the liquid-tight compartment encloses the at least one battery, the circuitry, and the at least one wireless communication circuit, wherein the liquid-contacting compartment encloses at least a portion of the first electrode and at least a portion of the second electrode such that the first electrode and the second electrode are in contact with the interstitial fluid.

9. The method of claim 2, wherein CGM device is:

configured to measure an electrical signal indicative of glucose oxidation occurring in the nanoporous layer while the first electrode and the second electrode are in contact with interstitial fluid of the subject, configured to apply a cleaning voltage input between the first and second electrodes to improve sensitivity of the nanoporous layer for glucose oxidation while the first electrode and the second electrode are in contact with interstitial fluid of the subject, and further configured to measure an impedance of the nanoporous layer for determining sensitivity of the nanoporous layer for glucose oxidation while the first electrode and the second electrode are in contact with the interstitial fluid of the subject.

10. The method of claim 2, wherein the CGM device is configured to apply the DC voltage input between the first electrode and second electrode for measuring an electrical signal indicative of glucose oxidation occurring in the nanoporous layer while the first electrode and the second electrode are in contact with the interstitial fluid of the subject.

11. The method of claim 2, wherein the CGM device is configured to apply the at least one non-DC voltage input between the first and second electrodes to renew surfaces of at least part of the metal nanoparticles while the first electrode and the second electrode are in contact with the interstitial fluid of the subject.

12. The method of claim 2, wherein the at least one non-DC voltage input is designed to cause at least part of materials in contact with surfaces of the metal nanoparticles to be removed therefrom.

13. The method of claim 2, wherein the EIS circuit is configured measure an impedance of the nanoporous layer when the at least one non-DC voltage is applied between the first electrode and the second electrode.

14. The method of claim 2, wherein the EIS circuit is configured to determine real time sensitivity of the nanoporous layer while the first electrode and the second electrode are in contact with the interstitial fluid of the subject based on the signal indicative of the electrochemically active surface area of the nanoparticles.

15. The method of claim 2, wherein the at least one non-DC voltage input is an AC voltage with an amplitude and a frequency designed to receive an impedance response of the nanoporous layer.

16. The method of claim 2, wherein the EIS circuit is configured to measure an impedance indicative of solid-liquid interface information of the nanoporous layer for determining real time sensitivity of the nanoporous layer for glucose oxidation while the first electrode and the second electrode are in contact with the interstitial fluid of the subject.

17. The method of claim 1, wherein determining the glucose sensitivity comprises:

applying an AC voltage input to the nanoporous layer while the CGM device is maintained in the subject's body; and measuring an impedance of the nanoporous layer in response to the AC voltage input, wherein the glucose sensitivity of the nanoporous layer is determined using the impedance.

18. The method of claim 1, wherein when the at least part of the CGM device is maintained in the subject's body over time, materials from the interstitial fluid contact or cover some surfaces of the metal nanoparticles; and the method further comprises applying a non-DC voltage input between the first electrode and the second electrode such that at least part of the materials contacting or covering surfaces of the metal nanoparticles are removed therefrom.

19. The method of claim 1, wherein when the at least part of the CGM device is maintained in the subject's body over time, materials from the interstitial fluid contact or cover some surfaces of the metal nanoparticles, which causes glucose sensitivity of the nanoporous layer to deteriorate;

the method further comprises:

while the first electrode and the second electrode are in contact with interstitial fluid of the subject, applying a first non-DC voltage input between the first electrode and the second electrode to remove at least part of the materials contacting the metal nanoparticles therefrom; and while the first electrode and the second electrode are in contact with interstitial fluid of the subject, applying a second non-DC voltage input between the first electrode and the second electrode to determine an impedance of the nanoporous layer.

20. A method comprising:

providing a continuous glucose monitor (CGM) device comprising:

electrodes comprising a first electrode and a second electrode, wherein the first electrode comprises a nanoporous layer comprising metal nanoparticles;

at least one battery;

at least one wireless communication circuit configured for wirelessly sending data to an external device; and circuitry comprising at least one DC voltage circuit, at least one non-DC voltage input circuit, and an EIS circuit configured to perform electrochemical impedance spectrometry, causing to insert at least part of the CGM device into a subject's body such that the first electrode and the second electrode are in contact with interstitial fluid of the subject, maintaining the at least part of the CGM device in the subject's body over time during which materials from the interstitial fluid contact or cover some surfaces of the metal nanoparticles, which causes glucose sensitivity of the nanoporous layer to deteriorate;

while the first electrode and the second electrode are in contact with interstitial fluid of the subject, applying a first non-DC voltage input between the first electrode and the second electrode to remove at least part of the materials contacting the metal nanoparticles therefrom; and while the first electrode and the second electrode are in contact with interstitial fluid of the subject, applying a second non-DC voltage input between the first electrode and the second electrode to determine an impedance of the nanoporous layer, wherein applying the first non-DC voltage input improves the glucose sensitivity substantially immediately, wherein the impedance of the nanoporous layer indicates or determines the glucose sensitivity of the nanoporous layer at the time of applying the second non-DC voltage, wherein the method further comprises measuring an electrical signal indicative of glucose oxidation for determining a glucose level of the subject subsequent to determining the glucose sensitivity.

\* \* \* \* \*